United States Patent
Yen et al.

(10) Patent No.: US 12,215,323 B2
(45) Date of Patent: Feb. 4, 2025

(54) EXOGENOUS CONTROL OF MAMMALIAN GENE EXPRESSION THROUGH APTAMER-MEDIATED MODULATION OF POLYADENYLATION

(71) Applicant: Baylor College of Medicine, Houston, TX (US)

(72) Inventors: Laising Yen, Pearland, TX (US); Liming Luo, Pearland, TX (US); Pei-Wen Chao, Sugar Land, TX (US)

(73) Assignee: Baylor College of Medicine, Houston, TX (US)

( * ) Notice: Subject to any disclaimer, the term of this patent is extended or adjusted under 35 U.S.C. 154(b) by 550 days.

(21) Appl. No.: 17/144,456

(22) Filed: Jan. 8, 2021

(65) Prior Publication Data
US 2021/0310003 A1  Oct. 7, 2021

Related U.S. Application Data

(63) Continuation of application No. 15/775,804, filed as application No. PCT/US2016/061665 on Nov. 11, 2016, now abandoned.

(60) Provisional application No. 62/254,435, filed on Nov. 12, 2015.

(51) Int. Cl.
| | | |
|---|---|---|
| C07H 21/04 | (2006.01) | |
| C12N 15/115 | (2010.01) | |
| C12N 15/67 | (2006.01) | |
| A61K 48/00 | (2006.01) | |

(52) U.S. Cl.
CPC ............ *C12N 15/115* (2013.01); *C12N 15/67* (2013.01); *A61K 48/00* (2013.01)

(58) Field of Classification Search
None
See application file for complete search history.

(56) References Cited

U.S. PATENT DOCUMENTS

| | | |
|---|---|---|
| 6,949,379 B2 | 9/2005 | Ramachandra |
| 8,680,017 B2 | 3/2014 | Lopreato |
| 2005/0158741 A1 | 7/2005 | Mulligan et al. |
| 2005/0260164 A1 | 11/2005 | Jolly et al. |
| 2011/0190386 A1 | 8/2011 | Kuo et al. |
| 2015/0056174 A1 | 2/2015 | Mulligan et al. |
| 2017/0253872 A1 | 9/2017 | Mulligan et al. |

FOREIGN PATENT DOCUMENTS

| | | |
|---|---|---|
| CN | 104651501 A | 5/2015 |
| EP | 1092777 A1 | 4/2001 |
| WO | WO-2004/027035 A2 | 4/2004 |
| WO | WO-2010/132665 A1 | 11/2010 |
| WO | WO-2014/193800 A2 | 12/2014 |
| WO | WO-2017/083747 A1 | 5/2017 |
| WO | WO-2017/136591 A1 | 8/2017 |
| WO | WO-2021/041924 A2 | 3/2021 |

OTHER PUBLICATIONS

Ashfield, R. et al., MAZ-dependent termination between closely spaced human complement genes, The EMBO Journal, 13(23):5656-5667 (1994).
Becskei, A. and Serrano, L., Engineering Stability in Gene Networks by Autoregulation, Nature, 405:590-593 (2000).
Becskei, A. et al., Positive Feedback in Eukaryotic Gene networks: Cell Differentiation by Graded to Binary Response Conversion, The EMBO Journal, 20(10):2528-2535 (2001).
Berens, C. et al., RNA aptamers as genetic control devices: The potential of riboswitches as synthetic elements for regulating gene expression, Biotechnology Journal, 10(2): 246-257 (2015).
Breaker, R. R. Engineering Allosteric Ribozymes as Biosensor Components, Analytical Biotechnology, 13:31-39 (2002).
Carrier, T. A. and Keasling, J. D., Investigating Autocatalytic Gene Expression Systems through Mechanistic Modeling, J. Theor. Biol. 201:25-36 (1999).
Cassiday, L. A. and Maher, L. J., Yeast genetic selections to optimize RNA decoys for transcription factor NF-kB, PNAS, 100(7):3930-3935 (2003).
Chen, F. et al., Cleavage Site Determinants in the Mammalian Polyadenylation Signal, Nucleic Acids Research, 23(14):2614-2620 (1995).
Ciesiolka, J. et al., Affinity selection-amplification from randomized ribooligonucleotide pools., Methods Enzymol., 267:315-335 (1996).
Contag, C. H. et al., Visualizing Gene Expression in Living Mammals Using a Bioluminescent Reporter, Photochemistry and Photobiology, 66(4):523-531 (1997).

(Continued)

*Primary Examiner* — Kimberly Chong
(74) *Attorney, Agent, or Firm* — Norton Rose Fulbright US LLP

(57) ABSTRACT

Embodiments of the disclosure concern the use of expression constructs in which at least one polyA signal is embedded upstream of an expressible transcript, such as within a 5' UTR for the transcript, for example. In certain embodiments, the polyA signal is comprised within a ligand-binding aptamer, and the binding of the ligand to the aptamer, or lack thereof, dictates the outcome for the expressible transcript. In specific embodiments, absence of the ligand causes the expressed transcript having a polyA in its 5' UTR to be expressed but then degraded, whereas presence of the ligand causes inhibition of degradation upon expression of the expressible transcript. More than one ligand-binding aptamer may be present on the same expression construct.

33 Claims, 48 Drawing Sheets
Specification includes a Sequence Listing.

(56) References Cited

OTHER PUBLICATIONS

Contag, P. R. et al., Bioluminescent indicators in living mammals, Nature Medicine, 4(2):245-247 (1998).
Demongeot, J. et al., Positive Feedback Circuits and Memory, Acad. Sci. Paris, 323:69-79 (2000).
Ellington, A. D. and Szostak, J. W., In Vitro Selection of RNA Molecules That Bind Specific Ligands, Nature, 346:818-822 (1990).
Famulok, M. et al., Functional Aptamers and Aptazymes in Biotechnology, Diagnostics, and Therapy, Chemical Reviews, 107(9):3716-3743 (2007).
Ferrel, J. E., Self-Perpetuating States in Signal Transduction: Positive Feedback, Double-Negative Feedback and Bistability, Current Opinion in Medical Biology, 6:140-148 (2002).
Fitzwater, T. and Polisky, B., A SELEX primer, Methods Enzymol., 267:275-301 (1996).
Gimmi, E. R., Alterations in the pre-mRNA topology of the bovine growth hormone polyadenylation region decrease poly(A) site efficiency, Nucleic Acids Research, 17:6983-6998 (1989).
Gossen, M. and Bujard, H., Tight control of gene expression in mammalian cells by tetracycline-responsive promoters, Proc. Natl. Acad. Sci. USA, 89:5547-5551 (1992).
Gromak, N. et al., Pause Sites Promote Transcriptional Termination of Mammalian RNA Polymerase II, Molecular and Cellular Biology, 26(10):3986-3996 (2006).
Hesselberth, J. R. et al., Simultaneous Detection of Diverse Analytes with an Aptazyme Ligase Array, Analytical Biochemistry 312:106-112 (2003).
Hung, S-C. et al., Mesenchymal Stem Cell Targeting of Microscopic Tumors and Tumor Stroma Development Monitored by Noninvasive In vivo Positron Emission Tomography Imaging, Clin. Cancer Res., 11(21):7749-7756 (2005).
International Search Report for PCT/US2016/061665 (Exogenous Control of Mammalian Gene Expression Through Aptamer-Mediated Modulation of Polyadenylation, filed Nov. 11, 2016), issued by ISA/US, 4 pages (Apr. 25, 2017).
Isaacs, F. J. et al., Prediction and Measurement of an Autoregulatory Genetic Module, PNAS, 100(13):7714-7719 (2003).
Jenison, R. D. et al., B. High-resolution molecular discrimination by RNA, Science, 263:1425-1429 (1994).
Kelzer, P. et al., Artificial riboswitches for gene expression and replication control of DNA and RNA viruses, Proceedings of the National Academy of Sciences of the United States of America, vol. 11(5): E554-E562 (2014).
Klasens, B. I. F et al., The Ability of the HIV-1 AAUAAA Signal to Bind Polyadenylation Factors Is Controlled by Local RNA Structure, Nucleic Acids Research, 27(2):446-454 (1999).
Lee, J. F. et al., Aptamer Database, Nucleic Acids Research, 32:D95-D100 (2004).
Levitt, N. et al., Definition of an efficient synthetic poly(A) site, Genes & Development, 3:1019-1025 (1989).
Long, S. B. et al., Crystal Structure of an RNA Aptamer Bound to Thrombin, RNA, 14:2504-2512 (2008).
Mandal, M. and Breaker, R. R., Gene Regulation by Riboswitches, Department of Molecular, Molecular Cell Biology, 5:451-468 (2004).
Mi, Z. et al., RNA Aptamer Blockade of Osteopontin Inhibits Growth and Metastasis of MDA-MB231 Breast Cancer Cells, Molecular Therapy, 17(1):153-161 (2009).
Navani, N. K. and Li, Y., Nucleic Acid Aptamers and Enzymes as Sensors, Science Direct, 10:272-281 (2006).
Ng, E. W. M. et al., Pegaptanib, a targeted anti-VEGF aptamer for ocular vascular disease, Nature, 5:124-132 (2006).
Nimjee, S. M. et al., Aptamers: An Emerging Class of Therapeutics, Annu. Rev. Med., 56:555-83 (2005).
Ory, D. S. et al., A stable human-derived packaging cell line for production of high titer retrovirus/vesicular stomatitis virus G pseudotypes, Proc. Natl. Acad. Sci. USA, 93:11400-11406 (1996).
Perez-Torres, C. J. et al., In Vitro and In Vivo Magnetic Resonance Imaging (MRI) Detection of GFP through Magnetization Transfer Contrast (MTC), Neuroimage, 50(2):375-382 (2010).

Proudfoot, N. et al., New Perspectives on Connecting Messenger RNA 3' End Formation to Transcription, Current Opinion in Cell Biology, 16:272-278 (2004).
Proudfoot, N. J., Integrating mRNA Processing with Transcription, Cell, 108:501-512 (2002).
Reiter, N. J. et al., DNA mimicry by a high-affinity anti-NF-kB RNA aptamer, Nucleic Acids Research, 36(4):1227-1236 (2008).
Rivera, V. M. et al., A humanized system for pharmacologic control of gene expression, Nature Medicine, 2(9):1028-1032 (1996).
Roth, A. et al., The Structural and Functional Diversity of Metabolite-Binding Riboswitches, Annual Review of Biochemistry, 78(1): 305-334 (2009).
Sheets, M. D. et al., Point mutations in AAUAAA and the poly (A) addition site: effects on the accuracy and efficiency of cleavage and polyadenylation in vitro, Nucleic Acids Research, 18(19):5799-5805 (1990).
Shu, X. et al., Mammalian Expression of Infrared Fluorescent Proteins Engineered from a Bacterial Phytochrome, Science, 324:804-807 (2009).
Suhr, S. T. et al., High level transactivation by a modified Bombyx ecdysone receptor in mammalian cells without exogenous retinoid X receptor, Proc. Natl. Acad. Sci. USA, 95:7999-8004 (1998).
Tang, J. and Breaker, R. R., Rational Design of Allosteric Ribozymes, Chemistry & Biology, 4(6):453-459 (1997).
Tuerk, C. and Gold, L., Systematic Evolution of Ligands by Exponential Enrichment: RNA Ligands toBacteriophage T4 DNA Polymerase, Science, 249(4968):505-510 (1990).
Vaish, N. K. et al., Monitoring post-translational modification of proteins with allosteric ribozymes, Nature Biotechnology, 20:810-815 (2002).
Warnock, D. E. et al., Identification of Protein Associations in Organelles, Using Mass Spectrometry-Based Proteomics, Mass Spectrometry Reviews, 23:259-280 (2004).
Win, M. N. and Smolke, C. D., A Modular and Extensible RNA-Based Gene-Regulatory Platform for Engineering Cellular Function, PNAS, 104(36): 14283-14288 (2007).
Win, M. N. and Smolke, C. D., Higher-Order Cellular Information Processing with Synthesis RNA Devices, Science, 322:456-460 (2008).
Winkler, W. C. and Breaker, R. R., Regulation of Bacterial Gene Expression by Riboswitches, Annu. Rev. Microbiol., 59:487-517 (2005).
Winkler, W. C. et al., Control of Gene Expression by a Nature Metabolite-Responsive Ribozyme, Nature, 428:281-286 (2004).
Written Opinion for PCT/US2016/061665 (Exogenous Control of Mammalian Gene Expression Through Aptamer-Mediated Modulation of Polyadenylation, filed Nov. 11, 2016), issued by ISA/US, 5 pages (Apr. 25, 2017).
Yaghoubi, S. S. et al., Non-Invasive Detection of Therapeutic Cytolytic T Cells with [18F]FHBG Positron Emission Tomography in a Glioma Patient, Nat. Clin. Pract. Oncol., 6(1):53-58 (2009).
Yaghoubi, S. S. et al., PET imaging of herpes simplex virus type 1 thymidine kinase (HSV1-tk) or mutant HSV1-sr39tk reporter gene expression in mice and humans using [18F]FHBG, Nature Protocols, 1(6):3069-3079 (2006).
Yamamoto, R. and Kumar, P. K. R., Molecular Beacon Aptamer Fluoresces in the Presence of Tat Protein of HIV-1, Genes to Cells, 5:389-396 (2000).
Yamamoto, R. et al., A Novel RNA Motif That Binds Efficiently and Specifically to the Tat Protein of HIV and Inhibits the Trans-Activation by Tat of Transcription In Vitro and In Vivo, Genes to Cells, 5:371-388 (2000).
Yen, L. et al., Exogenous control of mammalian gene expression through modulation of RNA self-cleavage, Nature, 431:471-476 (2004).
Yen, L. et al., Identification of inhibitors of ribozyme self-cleavage in mammalian cells via high-throughput screening of chemical libraries, RNA, 12:797-806 (2006).
Yonaha, M. and Proudfoot, N. J., Specific Transcriptional Pausing Activates Polyadenylation in a Coupled In Vitro System, Molecular Cell, 3:593-600 (1999).

(56) References Cited

OTHER PUBLICATIONS

Zarudnaya, M. I. et al., Downstream Elements of Mammalian Pre-Mrna Polyadenylation Signals: Primary, Secondary and Higher-Order Structures, Nucleic Acids Research, 31(5):1375-1386 (2003).
Zarudnaya, M.I. et, Polyadenylation of pre-mRNA 1. The formation of 3-ends of vertebrate mRNAs, Biopolymers Cell, 17(2): 93-108 (2001). [English Abstract, Russian].
Zhang, L. et al., Targeting Ku protein for sensitizing of breast cancer cells to DNA-damage, Int. J. Mol. Med. 14:153-159 (2004).
Wittmann, A. and Suess, B., Engineered riboswitches: Expanding researchers' toolbox with synthetic RNA regulators, FEBS Letters, 586:2076-2083 (2012).

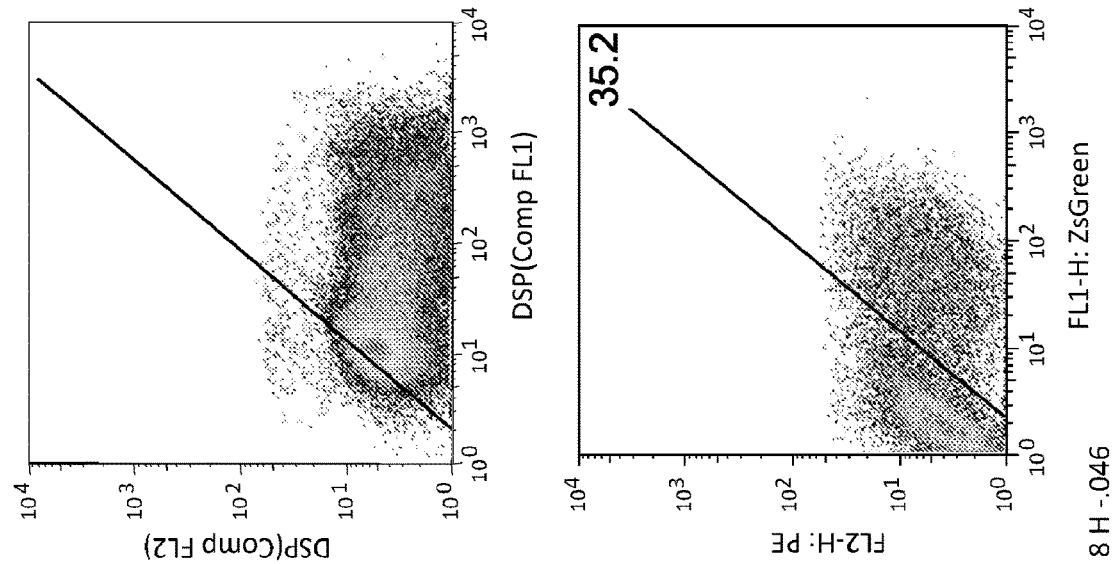
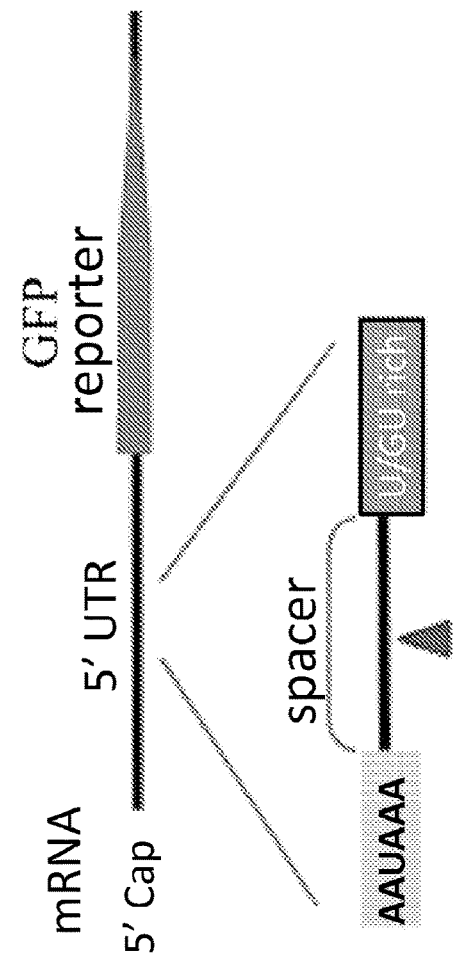
FIG. 5A

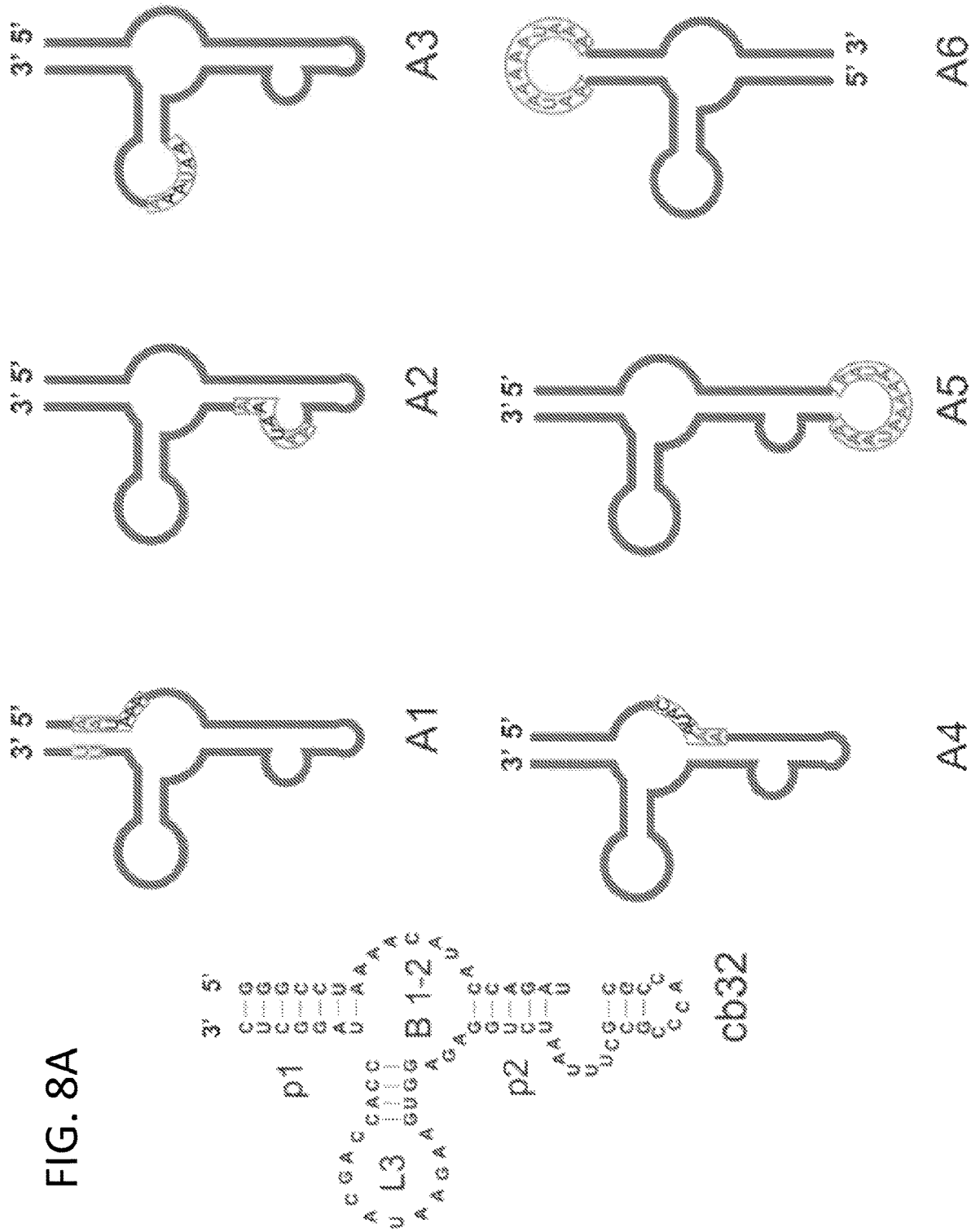

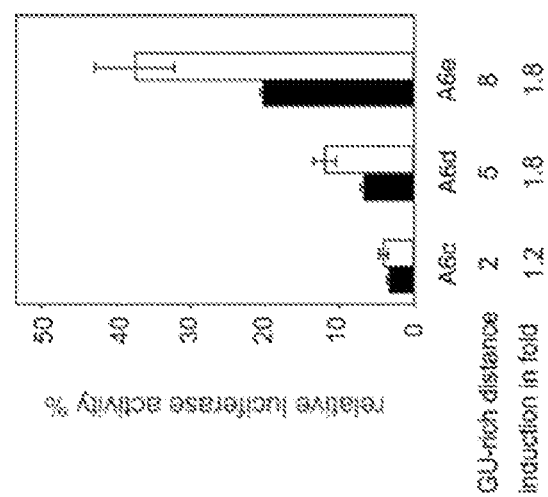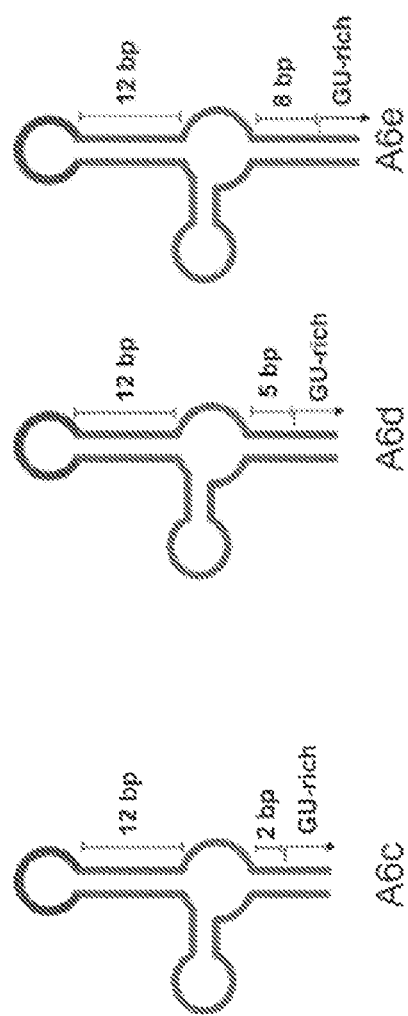
FIG. 9B

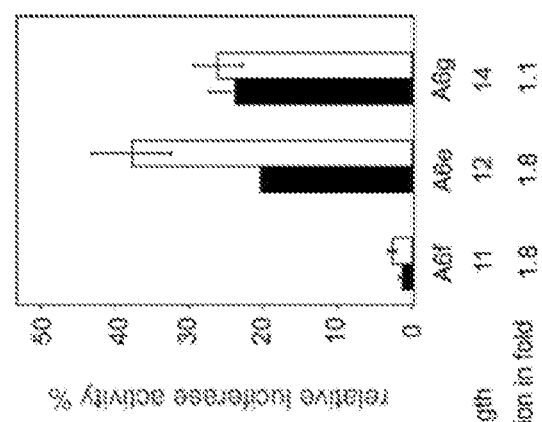
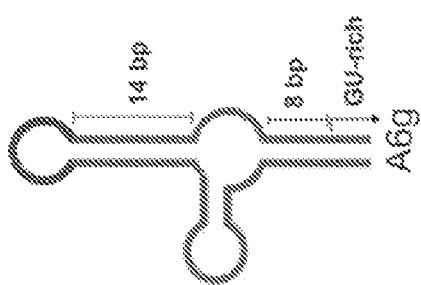
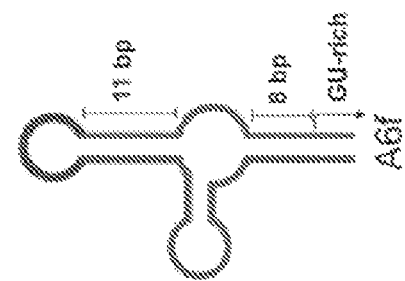
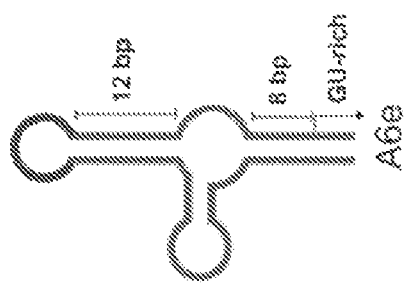
FIG. 9C

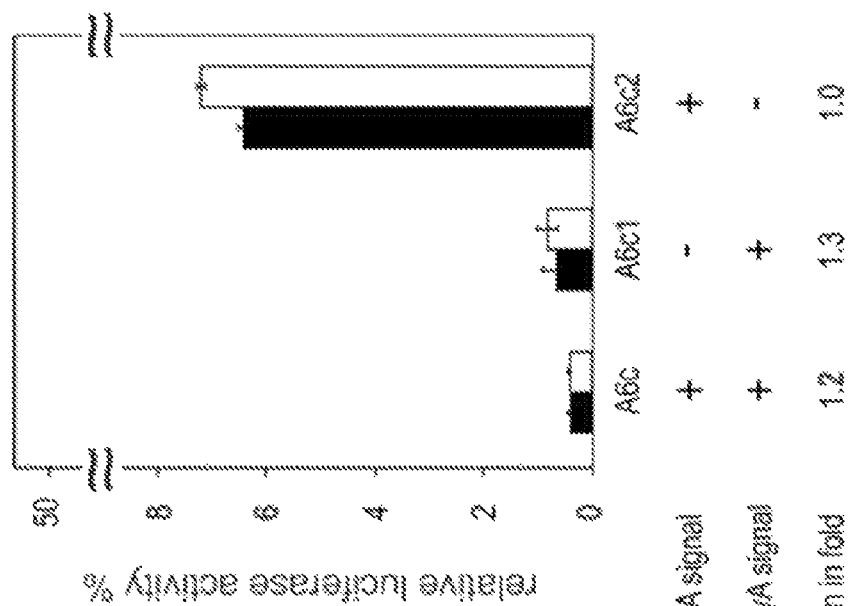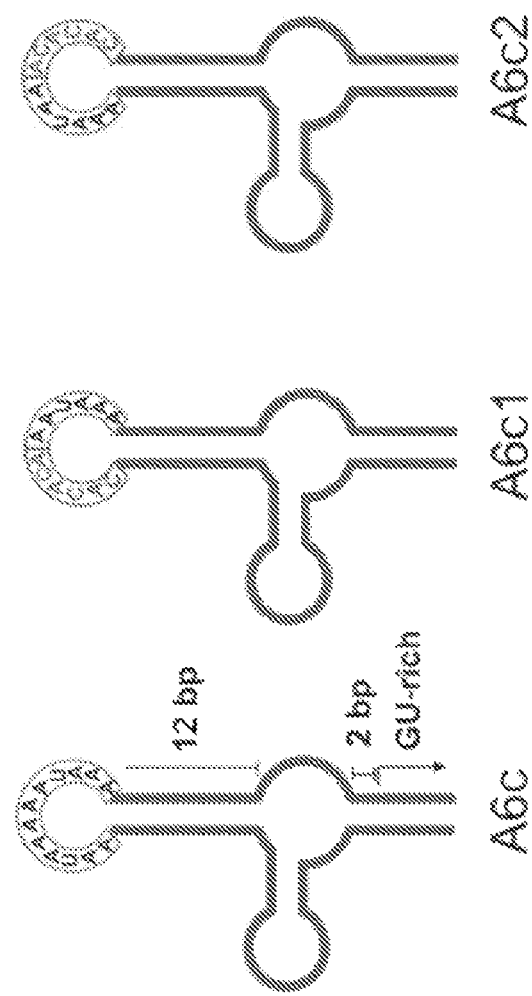
FIG. 10A

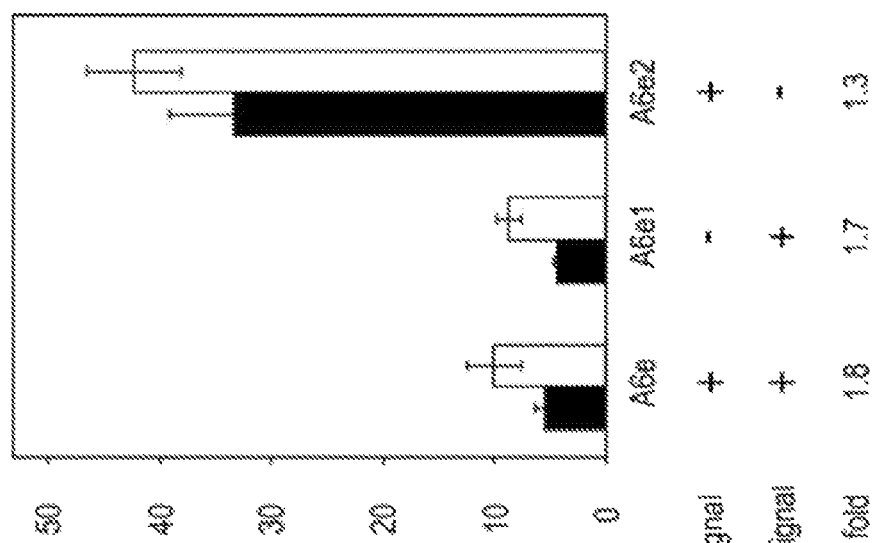
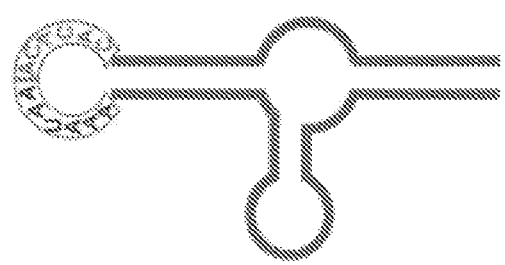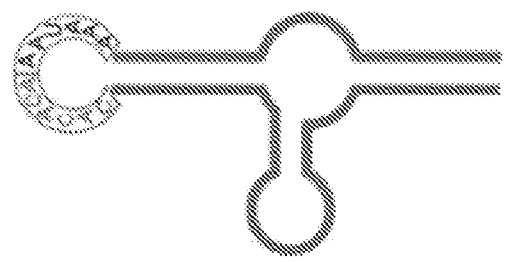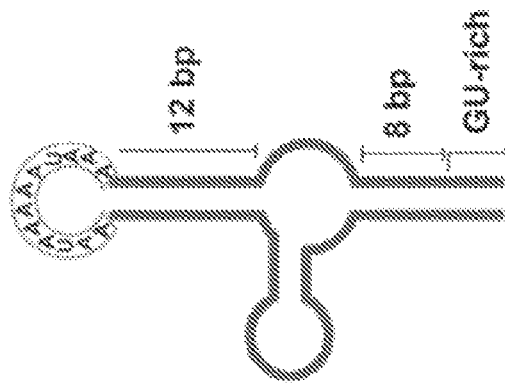
FIG. 10B

Induction in fold

| | Induction (15 ug/mL tc) | |
|---|---|---|
| | w/o helper | w/ helper |
| 103G | 4 | n/a |
| 103GP2 | 10 | 30 |
| 103GS3 | 5.5 | 10 |

Expression of reporter gene (luciferase activity)

| | Active polyA (AAUAAA) | Inactive polyA (ACACAC) | Dynamic range |
|---|---|---|---|
| 103GP2 | ~1266 | ~538868 | 423 |
| 103GS3 | ~4975 | ~507825 | 112 |

Variation in p2 w/o helpers

| Sequence | Induction in fold |
|---|---|
| CACAGAU (103G) | 4 |
| CACAAAU (103GP2) | 10 |
| CACAGGU | 8 |
| CACAUAU | 10 |
| CACUGAU | 9 |
| CACAGGU | 6 |

FIG. 25

GP2 sequence is shown Seq ID NO. 28

Modifications of GP2 in the boxed area

| name | sequence | Induction in fold | |
|---|---|---|---|
| MIN10P2 | AGAAAU | 5.4 | |
| EP2 | CGAAAG | 9.7 | |
| FP2 | ACGAAAGU | 11 | |
| GP2 | AUCGAAAGAU | 12.6 | Seq ID NO. 29 |
| HP2 | AUUGAAAGAU | 11 | Seq ID NO. 30 |

Tc concentration: 5 μg/mL

Tc concentration: 5 μg/mL

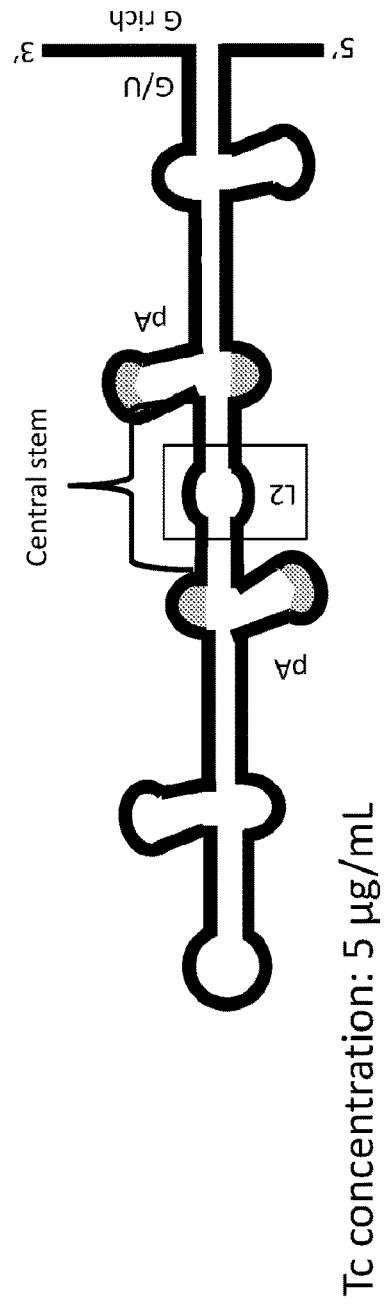

| | Stem/Loop-II of helper aptamer | | Stem/Loop-II of center aptamer | | Induction in fold |
|---|---|---|---|---|---|
| GP2SLGP2 | ACCAGATCGAAAGATCTGGGG | SEQ ID NO. 31 | ACCAGATCGAAAGATCTGGGG | SEQ ID NO. 45 | 70 |
| C2 | ACCAGATCGATCGATCTGGGG | SEQ ID NO. 32 | ACCAGATCGATCGATCTGGGG | SEQ ID NO. 46 | 64 |
| C7 | ACCAGATCGCGATCTGGGG | SEQ ID NO. 33 | ACCAGATCGCGATCTGGGG | SEQ ID NO. 47 | 38 |
| C9 | ACCAGATCGATCTGGGG | SEQ ID NO. 34 | ACCAGATCGATCTGGGG | SEQ ID NO. 48 | 22 |
| C10 | ACCAGATCGATTCGATCTGGGG | SEQ ID NO. 35 | ACCAGATCGAATCGATCTGGGG | SEQ ID NO. 49 | 61 |
| C11 | ACCAGATATCTGGGG | SEQ ID NO. 36 | ACCAGATATCTGGGG | SEQ ID NO. 50 | 58 |
| C12 | ACCAGATCGAATTCGATCTGGGG | SEQ ID NO. 37 | ACCAGATCGAATTCGATCTGGGG | SEQ ID NO. 51 | 94 |
| C14 | ACCAGATCGAATTTCGATCTGGGG | SEQ ID NO. 38 | ACCAGATCGAAATTCGATCTGGGG | SEQ ID NO. 52 | 58 |
| C15 | ACCAGATCGAATATTCGATCTGGGG | SEQ ID NO. 39 | ACCAGATCGAATATTCGATCTGGGG | SEQ ID NO. 53 | 60 |
| C16 | ACCAGATCGAATCATTCGATCTGGGG | SEQ ID NO. 40 | ACCAGATCGAATGATTCGATCTGGGG | SEQ ID NO. 54 | 62 |
| C17 | ACCAGATCGAATGATTCGATCTGGGG | SEQ ID NO. 41 | ACCAGATCGAATCGATTCGATCTGGGG | SEQ ID NO. 55 | 65 |
| C18 | ACCAGATTACCCTTGGGTGATCTGGGG | SEQ ID NO. 42 | ACCAGATTACCCGAGGGTGATCTGGGG | SEQ ID NO. 56 | 84 |
| C19 | ACCAGATCGAATCTGATTCGATCTGGGG | SEQ ID NO. 43 | ACCAGATCGAATCAGATTCGATCTGGGG | SEQ ID NO. 57 | 45 |
| D11A | ACCATCCTAAGCCTAAGGCAAACGCTATGTATGGTATGGATGGGG | | ACCAGATCGAAAGATCTGGGG | SEQ ID NO. 58 | 82 |
| | SEQ ID NO. 44 | | | | |

FIG. 27

GP2SLGP2 (370 bases):

GCTAGCCACACACAAATCTGGGGAGGTGAAGAATACGACCACCTGCGTTTTATACTTTGTTAAAACATACCAGATCGAA
AGATCTGGGGAGGTGAAGAAGAATACGACCACCTAATAAAGTGCAAAACATACCAGATCTGTGTTGGTTTTTGT
GTGGAATTCCACACACACAAATCTGGGGAGGTGAAGAATACGACCACCTGCGTTTTATACTTTGTTAAAACATACCAGATC
GAAAGATCGGGGAGGTGAAGAATACGACCACCTAATAAAGTATAAAGTGCAAAACATACCAGATCTGTGTGTTGGTTTT
TGTGTGAACGGGGAGGGGAGGAAAGGGGGAGGGGAGCGGGCCGC  SEQ ID NO. 59

C12 (374 bases):

CTGCAGCACACACACAAATCTGGGAGGTGAAGAATACGACCACCTGCGTTTTATACTTTGTTAAAACATACCAGATCGA
ATTCGATCGGGAGGTGAAGAATACGACCACCTAATAAAGTGCAAAACATACCAGATCTGTGTTGGTTTT
TTGTGTGGCTAGCCACACACACAAATCTGGGAGGTGAAGAATACGACCACCTGCGTTTTATACTTTGTTAAAACATACC
AGATCGAATTCGATCTGGGAGGTGAAGAATACGACCACCTAATAAAGTATAAAGTGCAAAACATACCAGATCTGTGTG
TTGGTTTTTTGTGAACGGGGAGGGGAGGAAAGGGGGAGGGGAGCGGGCCGC  SEQ ID NO. 60

D11A (396 bases):

GCTAGCGAATTGCACACACACAAATCTGGGGAGGTGAAGAATACGACCACCTGCGTTTTATACTTTGTTAAAACATACCAt
cctaagcctaaggcaaacgctatggaTGGGGAGGTGAAGAATACGACCACCTAATAAAGTGCAAAACATACCAG
ATCTGTGTGTTGGTTTTTTGTGTGAATTCCACACACACAAATCTGGGGAGGTGAAGAATACGACCACCTGCGTTTTATAC
TTTGTTAAAACATACCAGATCGAAGATCGAAGATCGAAGATCGGGGAGGTGAAGAATACGACCACTAATAAAGTGCAAAACATA
CCAGATCTGTCTGTGTTGGTTTTTTGTGTGAACGGGGAGGGGAGGAAAGGGGGAGGGGAGCGGGCCGC  SEQ ID NO. 61

FIG. 28

EXOGENOUS CONTROL OF MAMMALIAN GENE EXPRESSION THROUGH APTAMER-MEDIATED MODULATION OF POLYADENYLATION

This application is a continuation application of U.S. non-provisional application Ser. No. 15/775,804, filed May 11, 2018, which is the national phase application under 35 U.S.C. § 371 of International Application No. PCT/US2016/061665 filed Nov. 11, 2016, which claims priority to U.S. Provisional Patent Application Ser. No. 62/254,435, filed Nov. 12, 2015, which is incorporated by reference herein in its entirety.

STATEMENT REGARDING FEDERALLY SPONSORED RESEARCH OR DEVELOPMENT

This invention was made with government support under 1RO1EB013584-02 awarded by National Institutes of Health. The government has certain rights in the invention.

SEQUENCE LISTING

This applications contains a Sequence Listing which has been submitted electronically in the form of a text file (entitled "2011256-0555_SL_ST25.txt" created on Jun. 22, 2021 and is 14,638 bytes in size) the entire contents of which are incorporated herein by reference in their entirety.

TECHNICAL FIELD

Embodiments of the disclosure concern at least cell biology, molecular biology, gene modulation, gene therapy, stem cell therapy, medicine, molecular imaging, biosensors, and diagnostics.

BACKGROUND OF THE INVENTION

The ability to control the expression of a transgene with precision has always been indispensable in order to elucidate the function of a specific gene product, or to generate therapeutic proteins within a safe range. Currently several gene regulation systems are available[1-3] and they have proved to be extremely powerful experimental tools. However, despite their utility, these systems possess some practical limitations because of their reliance on hybrid transcriptional transactivators, and specialized promoters. These limitations include: (i) The need to have two transcriptional units, one for expressing the transactivator, the other for expressing the transgene to be regulated. As a result, using these systems require co-introducing two expression constructs. (ii) The potential toxicities from expression of a hybrid transactivator (e.g. induction of host immune responses directed towards the transactivators which are foreign proteins, effects of the transactivators on endogenous transcription, etc). (iii) Difficulties in application of such systems to the regulation in a tissue-specific manner because of the requirement of a specialized promotor. (iv) The limited number of small inducer molecules available for experimental and therapeutic application (because of the limited number of available systems). These limitations may be overcome by a gene regulation system that comprises, consists essentially of, or consists of only RNA, which does not involve any transactivator proteins and specialized promoters. The existence of entirely RNA-based mechanisms for controlling gene expression has been reported. In particular, a system based on the modulation of self-catalytic ribozyme has been described[4], providing a compelling rational for the development of a RNA-only system that has much wider applications in gene therapy and biological studies.

In contrast to gene regulation systems based on the control of transcription using transactivators, the polyA-based system provided herein does not require the expression of any protein transactivator products and is not dependent upon the use of any specialized promoter elements, and therefore, in theory, represents a 'portable' regulation system that could be 'embedded' into any endogenous gene or engineered vector transcription unit. As such, the system requires only one transcriptional unit (one expression construct), and is promoter flexible so that it can be used to regulate transgenes in a tissue-specific (spatial) and temporal manner. Because polyadenylation is a universal process occurs in all mammalian cells, the system described is widely applicable.

Another important area of application of gene regulation that has not been fully exploited, because of limitations of existing technology, is the ability to use gene regulation systems to function as biosensors for detecting the expression of specific cellular proteins or pathological events in vivo. Such biosensor platforms could provide in vivo temporal and spatial information regarding fluctuations in biomolecule levels, and the input information can be used to regulate cellular behavior or generate reporter signals for imaging or detection. For example, a gene regulation system that binds to a cancer-causing protein as its ligand, and in response, switches on or off a specific set of genes. These genes can generate reporter signals for quantitative detection or imaging, influence the course of metabolic pathways, or express therapeutic proteins. Molecular sensing of specific cellular proteins would allow the display of the biochemical abnormalities underlying disease in live cells. Such a technology would be useful to monitor the progress of clinical treatments by monitoring the expression of specific marker proteins, and in specific embodiments, forms an important platform to enable the testing and development of new therapeutic paradigms. Furthermore, such a technology would be useful in understanding the role of specific gene products in biological processes as well as disease development.

Modern proteomic technologies have offered several useful methods for visualizing or identifying endogenous cellular proteins. Methods such as Mass Spectrometry[5] allow the identification of hundreds of protein molecules present in mammalian cells or tissues. However, these methods destroy the cells and tissues in the process, and are incompatible with goals aimed at detecting specific cellular proteins in live animals or human. Methods that employ antibodies with conjugated signal-generating motifs, although powerful for visualizing specific proteins outside cell membrane, are unsuitable for detecting or imaging intracellular proteins that constitute most of the expressed proteins inside living cells. The lack of useful methods for detecting specific native proteins in vivo points to the need for new strategies for biosensing, as they will have a major impact in understanding fundamental biological processes and disease states.

The present disclosure satisfies a long-felt need in the art to provide methods and systems and compositions for using an RNA switch-based approach to detect the expression of native proteins and also to regulate genes of interest in live cells.

BRIEF SUMMARY OF THE INVENTION

Embodiments of the disclosure concern the exogenous control of gene regulation using aptamer-mediated modulation of polyadenylation. Embodiments of the disclosure concern the control of mammalian gene expression via regulation of polyA cleavage governed by the gatekeeper action of the binding of a ligand to an aptamer that encompasses the polyA signal.

Embodiments of the disclosure concern a molecular switch that controls the expression of a particular polynucleotide using aptamer-mediated modulation of polyadenylation. In specific embodiments, the molecular switch is a 5' UTR polyA signal-based RNA switch (which may be referred to herein as polyA switch or polyA sensor).

In specific embodiments, a system of the disclosure is utilized as a biosensor system that detects one or more intracellular "signatures" in live cells, tissues, or organisms. The "signature" may reflect the expression of one or more genes in question; the presence or absence of one or more endogenously-produced compounds, such as proteins or metabolites; the presence or absence of a molecule(s) that is indicative of a disease state or of a normal state or of efficacy of a therapy, or a combination thereof; and so forth. The system may be indicative of a metabolic or physiological state of one or more cells or tissues or of an organism.

In particular embodiments, the system comprises a polynucleotide that comprises in a 5' to 3' direction one or more ligand-binding aptamers comprising at least one polyA cleavage signal therein; and an expressible polynucleotide; the system is exposed to suitable conditions such that when the ligand is not present in the system or its environment, or the ligand does not bind the ligand-binding aptamer, mRNA from the expressible polynucleotide is degraded. In some embodiments, the system is subjected to suitable conditions, such that when the ligand binds the aptamer, mRNA from the expressible polynucleotide is not degraded, and a gene product is expressible from the expressible polynucleotide.

In certain embodiments, a system of the disclosure concerns the ability to modulate expression of one or more specific genes in question. The system allows manipulation of expression of the gene(s) by employing a particular ligand that can inhibit the 5' UTR polyA signal-based RNA switch, thereby leading to expression of the gene(s). The system allows tailor-made gene expression using ligands, such as small molecules, to control the expression, including, for example, in a tissue-specific and/or temporal-specific manner. In particular embodiments, the system acts as a biosensor system for using a tailor-made aptamer/expressible polynucleotide combination to provide information about endogenous ligands in a certain environment.

In one embodiment, there is a system for modulating gene expression, comprising a polynucleotide that comprises in a 5' to 3' direction: a) at least one ligand-binding aptamer each comprising at least one polyA cleavage signal therein (although in alternative embodiments not all aptamers have a polyA cleavage signal); and b) an expressible polynucleotide. In specific embodiments, the ligand binding aptamer comprising the polyA cleavage signal resides within the 5' untranslated region of the expressible polynucleotide. In specific embodiments, the system comprises a polynucleotide that expresses the ligand. In some aspects, the polynucleotide that expresses the ligand is the same polynucleotide that comprises the aptamer and expressible polynucleotide. In other cases, the polynucleotide that expresses the ligand is a different polynucleotide than the one that comprises the aptamer and expressible polynucleotide.

In certain embodiments, polynucleotides encompassed by the disclosure comprise two, three, or more polyA signals in the 5' UTR of the expressible polynucleotide. In a specific embodiment, the polynucleotide comprises: a) at least one polyA signal; b) the ligand-binding aptamer; and c) at least one U/UG rich region, at least one G rich region, or both of at least one U/UG rich region and at least one G rich region. In some embodiments of the system, the ligand-binding aptamer comprises one, two, three, or more U/UG rich regions. In certain aspects, in a 5' to 3' direction of the polynucleotide at least one polyA signal resides upstream of at least one U/UG rich region. In other aspects, in a 5' to 3' direction of the polynucleotide the ligand-binding aptamer resides upstream of one, two, or more U/UG rich regions. In particular aspects, in a 5' to 3' direction of the polynucleotide at least one polyA signal resides upstream of at least one G rich region. In some aspects, in a 5' to 3' direction of the polynucleotide the ligand-binding aptamer resides upstream of one, two, or more G rich regions. In particular embodiments, in a 5' to 3' direction of the polynucleotide the aptamer comprises two polyA signals and two U/UG rich regions. In cases wherein a polynucleotide comprises two or more aptamers, the polynucleotide may comprise only one G rich region, in certain aspects. In such cases, the G-rich region may be located on the 3'-most aptamer of the polynucleotide or may be located in the second aptamer in a 5' to 3' direction of the polynucleotide.

In some embodiments of the disclosure, the ligand is a polypeptide, peptide, nucleic acid, small molecule, drug, metabolite, or a combination thereof. In specific aspects, the aptamer is between 14 and 250 nucleotides in length. In particular embodiments, the expressible polynucleotide is a reporter gene, a therapeutic gene, or a gene whose product alters the metabolic state of the cells. In some cases, the polynucleotide is at least part of a vector. The polynucleotide that expresses the ligand may be at least part of a vector, such as a plasmid, a viral vector, or linear DNA. In particular embodiments, the expressible polynucleotide encodes the ligand. Expression of the expressible polynucleotide may be regulated by a tissue-specific promoter, in some aspects.

In certain embodiments, there is a method of modulating gene expression, comprising the steps of: a) providing a system, said system comprising a polynucleotide that comprises in a 5' to 3' direction: 1) at least one ligand-binding aptamer each comprising at least one polyA cleavage signal therein; 2) an expressible polynucleotide; and 3) optionally a ligand-expressing construct; and b) subjecting the system to suitable conditions, wherein when mRNA from the expressible polynucleotide is not desired, the ligand does not bind the ligand-binding aptamer or is not present in the system or its environment, and mRNA from the expressible polynucleotide is degraded; or c) subjecting the system that comprises the ligand-expressing construct to suitable conditions, wherein when expression of the expression polynucleotide is desired, the ligand binds the aptamer and/or is present in the system or its environment, and mRNA from the expressible polynucleotide is not degraded.

In one embodiment, there is a method of modulating gene expression, comprising the steps of: a) providing a system, said system comprising a polynucleotide that comprises in a 5' to 3' direction: 1) at least one ligand-binding aptamer each comprising at least one polyA cleavage signal therein; 2) an expressible polynucleotide; and 3) optionally a ligand-expressing construct; and b) subjecting the system to suitable conditions, wherein when the ligand is not present in the system or its environment or does not bind the ligand-binding aptamer, mRNA from the expressible polynucleotide is degraded; or c) subjecting the system that comprises the ligand-expressing construct to suitable conditions, wherein when the ligand binds the aptamer, mRNA from the expressible polynucleotide is not degraded, and a gene product is expressible from the expressible polynucleotide. In specific embodiments, the method occurs in a cell, such as a stem cell, a cancer cell, or a diseased or defective cell in need of gene therapy of a gene (such as dystrophin, albumin, or factor IX). In particular aspects, the ligand is endogenous to the cell. In particular aspects, the method occurs in vivo, such as in a mammal, including a human. In other aspects, the method occurs in vitro. In some embodiments, the method occurs in one or more cells of an individual, the ligand is glucose, the individual has diabetes, pre-diabetes, or complications from diabetes, and/or the expressible polynucleotide is insulin. In some aspects, the method occurs in one or more cells of an individual, the ligand is the gene product of a cancer biomarker, and the expressible polynucleotide is a suicide gene. In particular aspects, the method occurs in an individual, the expressible polynucleotide is a reporter gene, and the location and/or intensity of the expression of the reporter gene provides information about spatial distribution, temporal fluctuation, or both, of a ligand in one or more cells of the individual. In some embodiments, the method further comprises the step of designing the aptamer to suitably bind the ligand. In specific embodiments, the method occurs in an individual, tissue, or cell, wherein the expressible polynucleotide encodes a detectable gene product, and wherein the respective individual, tissue, or cell is imaged.

In certain embodiments, there is a method of monitoring the therapy for an individual, comprising the step of providing to the individual: a) a vector comprising a polynucleotide that comprises in a 5' to 3' direction: 1) at least one ligand-binding aptamer each comprising at least one polyA cleavage signal therein; and 2) an expressible polynucleotide; and/or b) one or more cells harboring the vector of a), wherein the ligand is a specific gene product of a protein that is indicative of the efficacy of the therapy. In specific embodiments, the vector of a) and/or the cells of b) are provided to the individual before the therapy, during the therapy, and/or after the therapy.

In one embodiment, there is a method of assaying for the presence, risk, or susceptibility for a medical condition in an individual, comprising the steps of providing to the individual: a) a vector comprising a polynucleotide that comprises in a 5' to 3' direction: 1) at least one ligand-binding aptamer each comprising at least one polyA cleavage signal therein; and 2) an expressible polynucleotide; and/or b) one or more cells harboring the vector of a), wherein the expression of the expressible polynucleotide, or absence of expression of the expressible polynucleotide, identifies whether or not the ligand is present to bind the aptamer, wherein the respective presence or absence of the ligand in the individual or cells thereof is indicative of the presence, susceptibility or risk for the medical condition.

In a certain embodiment, there is a polynucleotide, wherein said polynucleotide comprises in a 5' to 3' direction: a) at least one ligand-binding aptamer each of which comprises at least one polyA cleavage signal therein; and b) an expressible polynucleotide. In specific embodiments, the ligand-binding aptamer is located in the 5' UTR of the expressible polynucleotide. In some aspects, the polynucleotide further comprises at least one U/UG rich region, at least one G rich region, or both of at least one U/UG rich region and at least one G rich region. In other aspects, in a 5' to 3' direction of the polynucleotide at least one polyA signal resides upstream of at least one U/UG rich region. In specific cases, in a 5' to 3' direction of the polynucleotide the ligand-binding aptamer resides upstream of one, two, or more U/UG rich regions. In particular cases, in a 5' to 3' direction of the polynucleotide at least one polyA signal resides upstream of at least one G rich region. In particular aspects, in a 5' to 3' direction of the polynucleotide the ligand-binding aptamer resides upstream of one, two, or more G rich regions.

Other embodiments concern cells that comprise any polynucleotide encompassed by the disclosure. In specific embodiments, the cell is a mammalian cell, such as a human cell, and the cell may reside in a human. In some embodiments, the cell comprises any system encompassed by the disclosure. In specific embodiments, the cell is a mammalian cell, such as a human cell, and the cell may reside in a human. In particular embodiments, there is a vector encompassed by the disclosure and comprising any polynucleotide encompassed by the disclosure. In specific cases, the vector is a viral vector, such as an adenoviral vector, an adeno-associated viral vector, a retroviral vector, or a lentiviral vector. In specific embodiments, the vector is a plasmid.

BRIEF DESCRIPTION OF THE DRAWINGS

FIGS. 5A-5C illustrate that polyA signal can be cleaved efficiently at 5' UTR. FIG. 5A illustrates the structure of a reporter gene having insertion of a polyA signal into the 5'UTR of the reporter gene green fluorescent protein GFP together with the required U/GU rich region. FIG. 5B illustrates utilization of one or two copies of G-rich element was added after the U/GU rich region. FIG. 5C shows inclusion of two copies of polyA signal to enhance polyA cleavage. Cleavage efficiency with different polyA motifs was indirectly measured by flow cytometry analysis. X-axis indicates GFP expression levels. Red diagonal line separates GFP-positive from GFP-negative cells. The bottom configuration resulted in fewest green cells due to two copies of polyA signal leading to greatly reduced GFP levels [SEQ ID NO: 3];

(FIG. 7A) Reporter expression level visualized by IVIS200 bioluminescence imager at different ligand construct dosage in terms of the amount of plasmid transfected. Each well contained roughly 10 thousand cells. The expression level of inactive polyA vector is the reference 100% induction. (FIG. 7B) Induction in 'fold' calculated as a ratio of reporter signal (luciferase) in the presence vs. absence of the transfected ligand construct at different dosage. The reporter signal is measured using luminometer. Three different polyA sensors are shown (sensor with active pA, sensor with inactive pA, or no pA control plasmid) at different ligand dosage in terms of the amount of plasmid transfected. (FIG. 7C) Northern analysis of luciferase mRNA expression visualized by a probe against the 5' UTR shared by all plasmid vectors. Tat mRNA was visualized by a probe against the mRNA. A probe against GAPDH is used as internal control. pA: polyA signal. The results confirmed that the presence of ligand (tat) leads to intact full-length transgene mRNA (land 5, upper band);

FIGS. 8A-8B show efficiency of PolyA cleavage is dependent on the position of polyA signal in the example of a tetracycline-binding aptamer (cb32 tc-aptamer). (FIG. 8A) (SEQ ID NO: 4). The tc-aptamer used as the template (left panel), and the positions where polyA signal (AAUAAA) were placed are shown. Mutations made within the tc-aptamer for the purpose of creating a polyA signal are shown with blue letters. (FIG. 8B) The plots display the relative luciferase activity measured without tetracycline (tc) thus reflect the efficiency of polyA cleavage. The activity of the parental plasmid with no polyA switch is set to 100%. In this series, the A6 configuration exhibits the highest polyA cleavage efficiency. The open bar for A6 is the inactive polyA (CACACA) control;

FIGS. 9A-9C show the effects of P1 stem length and position of GU-rich region on regulating the efficiency based on construct A6. The red line indicates two polyA signals. The P1 length, and the distance between GU-rich region and B1-2 is given in bp. The induction of gene expression is shown by the relative luciferase activity of constructs in the absence (black bars) and presence (white bars) of 15 µg/ml tc. Regulation efficiency determined as the ratio of relative luciferase activity with and without tc is given by the numbers under the plot. (FIG. 9A) Constructs with different P1 length with 2 bp GU distance. The results show that P1 length of 12 bp leads to the induced gene expression by tc. (FIG. 9B) constructs with P1 length of 12 bp but different GU-rich distance. A GU-rich distance of 5 bp or 8 bp leads to the best induced gene expression by tc. (FIG. 9C) Constructs with different P1 length but fixed 8 bp GU distance. P1 length of 11 bp or 12 bp leads to the best induced gene expression by tc when GU distance is fixed at 8 bp;

FIGS. 10A-10B show that the second polyA signal in the loop played a more important role in polyA cleavage. (FIG. 10A) (SEQ ID NO: 5; SEQ ID NO: 6; SEQ ID NO: 7) Constructs with P1 length of 12 bp with 2 bp GU distance. (FIG. 10B) (SEQ ID NO: 5; SEQ ID NO: 6; SEQ ID NO: 7) Constructs with P1 length of 12 bp with 8 bp GU distance. Left side: Schematic view of various constructs. The active polyA signals are indicated by red line, the inactive polyA signals are indicated by blue line, and the mutations that convert active to inactive polyA signal (CACACA) in blue letters. Right side: Relative luciferase activity in the absence (black bars) and presence (white bars) of 15 µg/ml tc. Regulation efficiency determined as the ratio of relative luciferase activity with and without tc is given by the numbers under the plot. In both cases, the second polyA signal in the loop played a more important role in polyA cleavage;

(FIG. 11A) (SEQ ID NO: 8; SEQ ID NO: 9) Schematic view of constructs tested. Construct A8 and A8* differ in one A-U pair as indicated by the blue box. (FIG. 11B) Relative luciferase activity in the absence (closed) and presence (open bars) of 15 µg/ml tc. Regulation efficiency determined as the ratio of relative luciferase activity with and without tc is given by the numbers under the plot;

(FIG. 12A) Schematic view of constructs. A8g construct utilizes two tc aptamers flanking the polyA signal. A8h construct utilize one tc aptamer and one neomycin aptamer flanking the polyA signal. (FIG. 12B) Relative luciferase activity in the absence (closed) and presence (open bars) of 15 µg/ml tc. Note that inserting additional G-C base pairs immediately 5' to the polyA signal, which stabilizes the P1 stem, leads to the loss of polyA activity (construct A8f). This confirms that the polyA signal can be efficiently inactivated by stabilizing the P1 stem. In addition, flanking the polyA signal by two tc aptamers further improves regulation efficiency (construct A8g). In all cases 15 µg/ml tc are used, with the exception of A8h in which 15 µg/ml tc and 15 ug/ml of neomycin were used;

(FIG. 13A; [SEQ ID NO: 10; SEQ ID NO: 11; SEQ ID NO: 12]) Sanger sequencing results of the 5' UTR polyadenylated mRNA fragments. The vertical black line indicates the position where polyA tail is added to the 5' UTR fragment. (FIG. 13B; SEQ ID NO: 13) The identified polyA cleavage sites are marked with black arrows around the B1-2 bulge of the tc binding core;

(FIG. 14A; SEQ ID NO:14) Schematic view of daughter constructs derived from A8 with different lengths of P1 (A8a, A8b, A8c, A8d). Arrows point to the predicted major polyA cleavage sites for each construct based on the data shown in FIG. 13. (FIG. 14B) Relative luciferase activity of constructs with different lengths of P1 in the absence (closed) and presence (open bars) of 15 µg/ml tc. This result shows that A8 remains the most efficient configuration.

FIG. 20 provides the corresponding luciferase expression levels and induction of the exemplary 103G, 103GP2 and 103GS3 aptamers. The construct 103GP2 shows the highest theoretical dynamic range of 423 fold, and the highest induction of 30 fold by tc.

FIG. 21 demonstrates variation in modification of the P2 region of 103GP2 and the corresponding impact on induction of gene expression [SEQ ID NO: 19].

FIG. 25 provides an example of a polyA sensor construct, GP2, with polyA signal flanked by 2 aptamers in different orientation [SEQ ID NO: 28, 29, 30].

FIG. 27 demonstrates variation in the length and sequence of the stem/loop-II region (the boxed region) of the Helper GP2 and the Center GP2, and the corresponding impact on induction of gene expression is shown. Sequence variation between different constructs are shown [SEQ ID NO: 31-58].

FIG. 28 provides complete sequence of the exemplary polyA sensors of GP2SLGP2 [SEQ ID NO: 59], C12 [SEQ ID NO: 60], and D11A [SEQ ID NO: 61].

DETAILED DESCRIPTION OF THE INVENTION

Figure 1A:
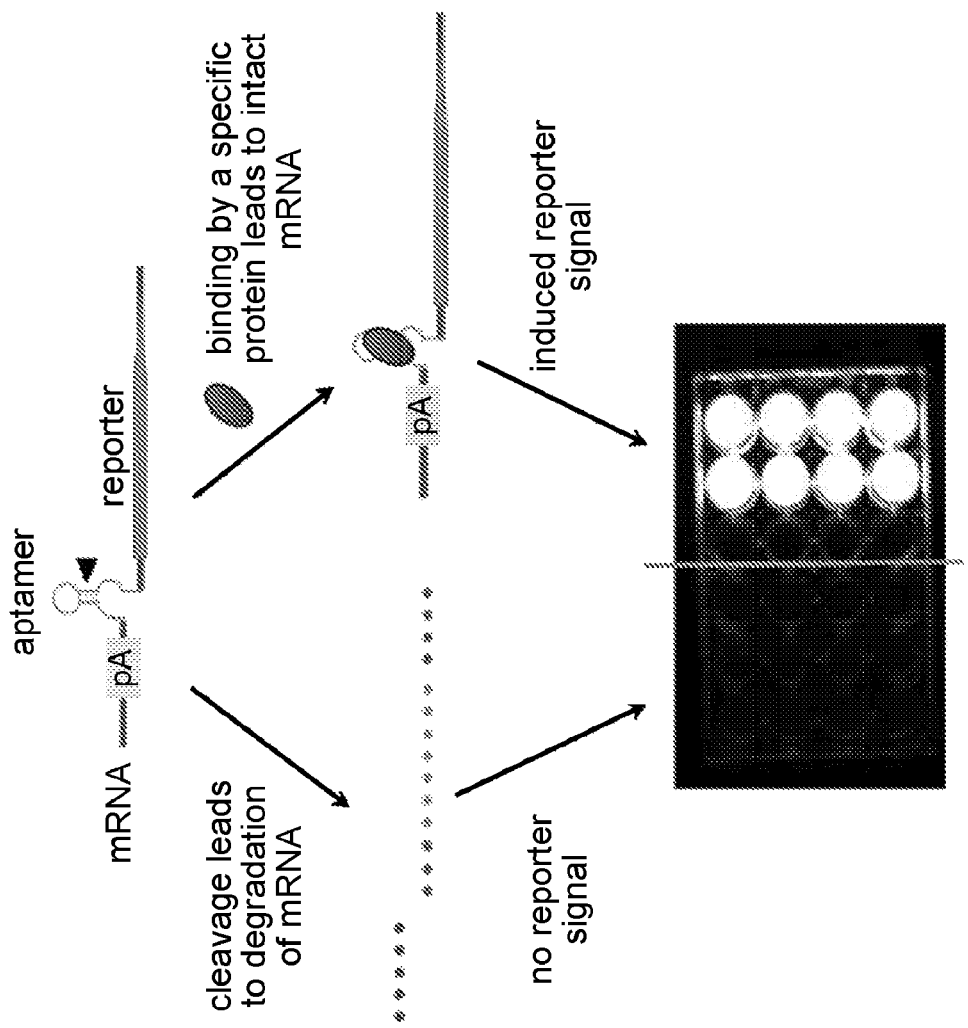
FIG. 1A depicts an exemplary strategy for imaging a specific intracellular protein via the modulation of polyA signal cleavage. Efficient cleavage of the polyA signal (pA) engineered within the 5'UTR leads to the destruction of the mRNA and loss of expression of reporter signal. Binding of a ligand protein to the aptamer coupled to the polyA site blocks the cleavage, resulting in preservation of the intact mRNA, and enabling expression of reporter signal. Triangle indicates the pA cleavage site. The pA normally present in the 3' UTR is omitted for clarity. The bottom image was obtained by co-transfection of a DNA plasmid coding the polyA switch with (right) or without (left) the plasmid coding the ligand protein (tat) in human 293T cells. The presence of ligand protein clearly induced the expression of a bioluminescent reporter signal that was readily detectable by imaging.

Aptamers are short RNA sequences that fold like receptors and bind to specific ligands[19-21]. Efficient 'in vitro evolution'[8,12] methods for generating aptamers with high affinity to specific ligands are well established[7,9,22]. The binding affinity of aptamers can often reach nanomolar range, comparable to that of antibodies. In this regard, aptamers can be viewed as antibodies made of RNA. What distinguishes an aptamer from an antibody are its small size (often smaller than 50 bases) and its modular nature. These features enable aptamers to integrate with and control other RNA structures without losing its binding function. It has been demonstrated that aptamers can transform the self-cleaving RNA ribozymes to operate in a ligand-dependent manner, and function like a molecular switch in test tubes[23,24].

Nature has successfully exploited the aptamer mechanism in the form of 'riboswitches'[25] to regulate gene expression. Many naturally occurring aptamers are found in bacteria, wherein binding of input ligands to aptamers modulate gene expression via the mechanisms of transcriptional attenuation, translational inhibition, and alternative splicing, in addition to RNA cleavage[25,26]. An estimated 2-3% of all bacterial genes and an unknown number of yeast genes are believed to be controlled in this fashion[27]. Through an aptamer-mediated mechanism, the location and intensity of reporter gene expression over time would reflect the spatial distribution and temporal fluctuation of the specific intracellular ligand in vivo. The reporter gene products, such as luciferase, thymidine kinase, near-infrared or infrared fluorescence protein (for example), can be monitored by modern imaging instruments such as bioluminescence imager or Positron Emission Tomography (PET), for example. Near-infrared or infrared fluorescence protein are useful for in vivo whole-body imaging techniques. This approach requires no a priori labeling or manipulation of native protein under study, hence addressing a class of measurements that has been difficult to address previously in vivo.

RNA aptamers recognize specific ligands with high affinity, but powerful methods that amplify the signal generated by aptamer binding have been lacking. Although a few studies reported the use of aptamer to control ribozyme cleavage and enabled it to function as molecular switches that respond to specific ligands in mammalian cells, the poor dynamic ranges (often less than a 5-fold inducible range), and high leakage expression[28,29] exhibited by these sensors severely limited their uses.

One can consider that an impediment to utilizing aptamers as a sensing device in mammalian cells is the absence of a powerful switching/amplifying mechanism that couples the binding of ligand/aptamer to reporter gene expression. The present disclosure provides such a switching/amplifying mechanism, so that aptamers and reporter genes (or transgenes, for example) could be efficiently coupled to detect specific molecular signatures in live cells or to control the expression of a transgene. As described herein, one embodiment involves the modulation of polyA signal cleavage via ligand-aptamer interaction.

The words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein embodiments which are disclosed and still obtain a like or similar result without departing from the spirit and scope of the disclosure.

Figure 1B:
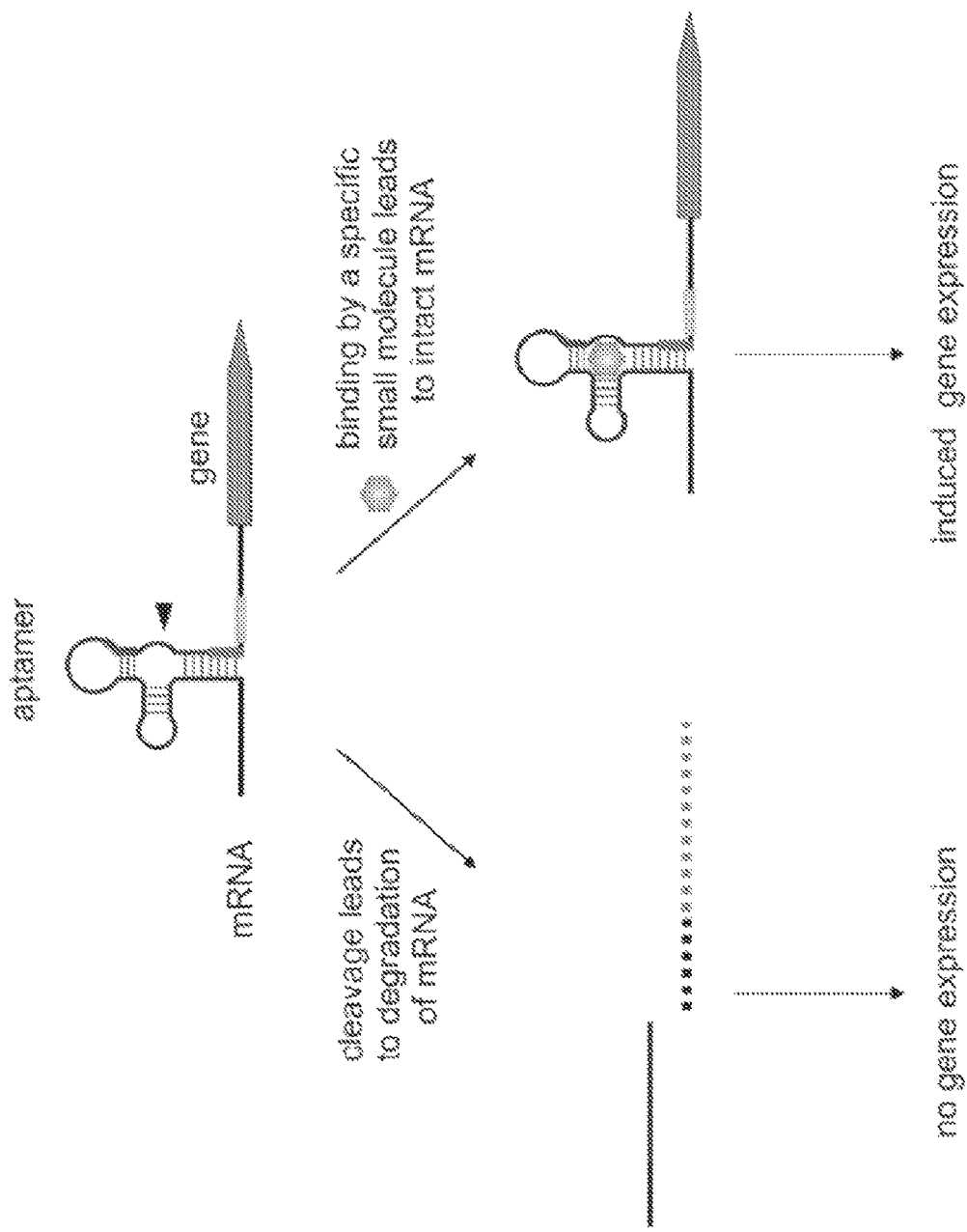
FIG. 1B shows small molecule-aptamer interaction regulates polyA cleavage. An aptamer with engineered pA that binds a small molecule is inserted in the 5' UTR of a gene. The 5'UTR polyA cleavage leads to the destruction of the 3' part of mRNA and therefore the absence of gene expression. However, binding of an administrated small molecule to the aptamer blocks the 5'UTR polyA and leads to generation of intact mRNA and therefore protein expression. The 5' UTR of mRNA is shown as black line, and a gene of interest as boxes. The small molecular ligand is shown as pink hexagon, and the cleavage site as black triangular.

This disclosure concerns the harnessing of the power of polyA cleavage to generate an efficient molecular switch that will enable sensitive detection of specific molecular signatures or states in mammalian cells or that will control the expression of a transgene in mammalian cells using small molecules, such as drugs or drug-like molecules, for example. The engineered molecular switch can control the expression of a reporter gene or a transgene (for example) by aptamer-mediated modulation of polyadenylation (FIGS. 1A and 1B). Polyadenylation is an essential mRNA processing mechanism that is universally present in all mammalian cells. Mammalian polyA signals are usually located at the 3'-untranslated region (UTR). When a new polyA site is artificially created at 5' UTR, where they are never localized in normal transcriptional units, efficient cleavage of that polyA signal leads to destruction of the mRNA and therefore loss of gene expression. However, binding of a ligand molecule to the engineered polyA signal efficiently blocks the cleavage, resulting in preservation of the intact mRNA, thus enabling induced gene expression.

General Embodiments of PolyA-Based Switches

The disclosure concerns systems that generally and intentionally employ a polyA signal present in an expression construct at a location other than at the 3' untranslated region (UTR) of an expressible polynucleotide, such as a gene. In particular embodiments, the ectopic location of the polyA signal allows exploitation of the system of the present disclosure to modulate an expressible polynucleotide of interest. In specific embodiments, the polyA signal is present upstream of the translation start site of expressed polynucleotide (mRNA), and in specific embodiments the polyA signal is located in the 5' UTR of the mRNA. In particular embodiments, the expressible polynucleotide is able to be transcribed by RNA polymerase II. In specific embodiments, the design of the expression construct intentionally locates the polyA signal to the 5'UTR of the expressible polynucleotide.

In certain embodiments, the presence of the polyA signal in the 5' UTR targets the mRNA for degradation, and this ability is exploited in the systems of the disclosure. In particular embodiments, the polyA signal is associated with an aptamer to which one or more ligands can bind, and the binding of the ligand to the aptamer dictates whether or not the mRNA is degraded. In specific embodiments, when an mRNA is desired to be expressed, the ligand that binds the aptamer is provided. In some cases, the question of whether or not a ligand is present in a particular environment (cell, tissue, or organism, for example) is answered by whether or not a particular expressible polynucleotide is expressed upon regulation by the particular polyA/aptamer that can be bound by that ligand. In embodiments wherein the ligand binds the aptamer and the mRNA is expressed, the system allows amplification of a signal, because multiple gene products can be produced from a single mRNA.

As shown in FIGS. 1A and 1B, binding of a particular ligand to the aptamer blocks the polyA cleavage, resulting in preservation of the intact mRNA and therefore expression of a reporter signal (such as in biosensor systems of the disclosure) or of a particular gene, such as a therapeutic gene (such as in gene regulation systems of the disclosure); the ligand can be of any kind, including a protein or small molecule, for example. In particular embodiments, the ligand of the system for the biosensor embodiments is endogenous to a particular cell, tissue, or organism, whereas the ligand of the system for gene regulation systems is not necessarily an endogenous ligand.

Figure 11A:
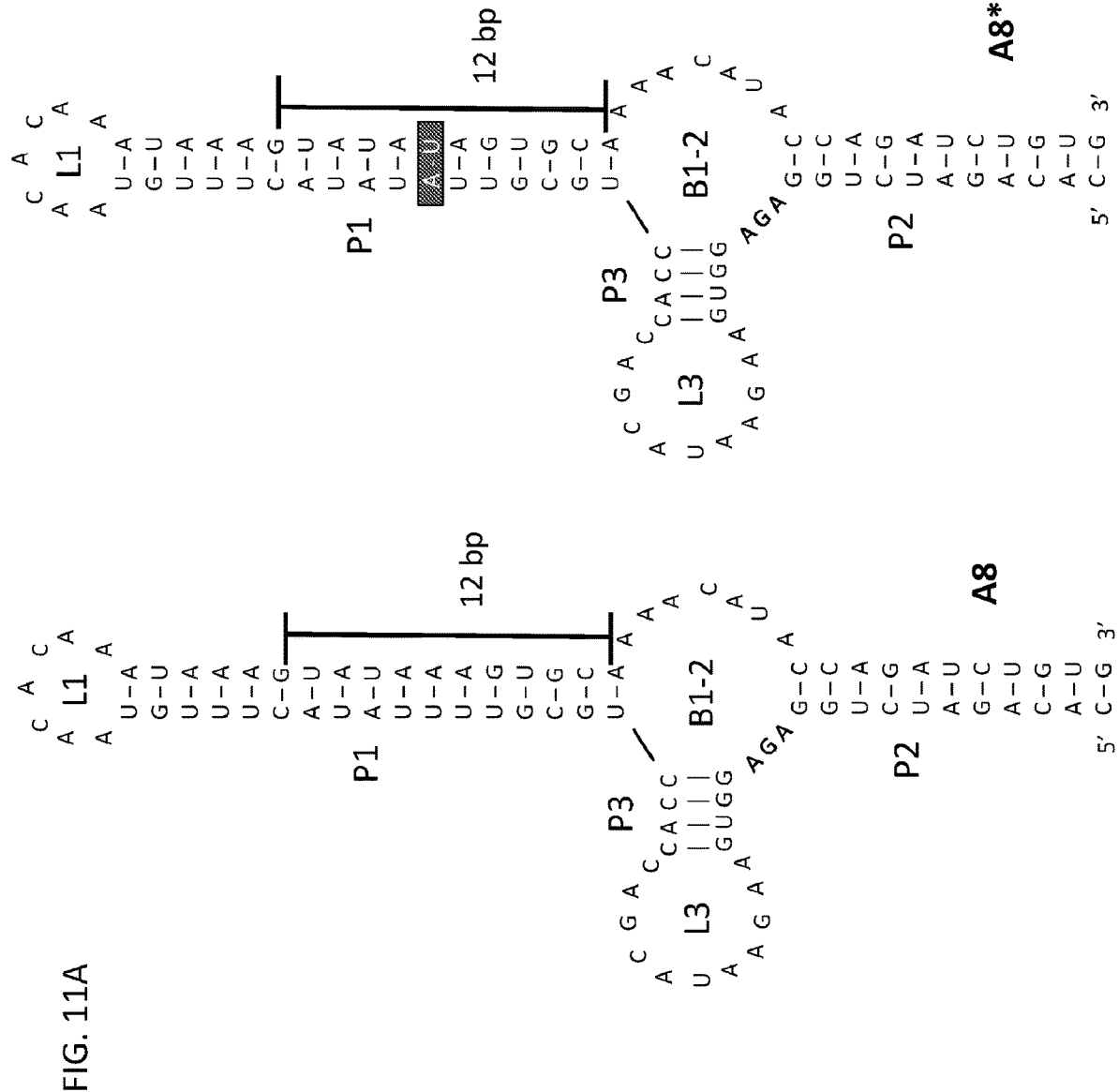
FIGS. 11A-11B show polyA signal partially embedded in a new P1 stem and this leads to improved regulation efficiency.
Figure 11B:
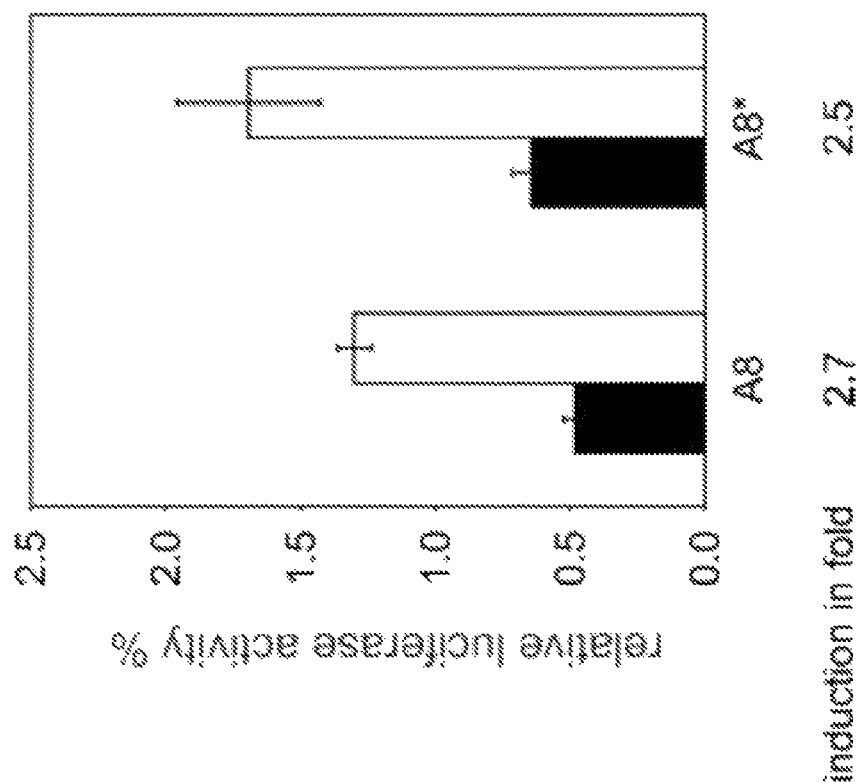

In specific embodiments, in a construct comprising the polyA signal, the aptamer comprises the polyA signal within it. In some embodiments, the aptamer comprises one or more polyA signals, such as one, two, three, or more polyA signals (see FIG. 11). CACACA replacing AAUAAA largely inactivates the polyA signal, thus resembling a theoretical upper limit of gene expression level when polyA signal is blocked. The ratio of expression level of CACACA vs. AAUAAA is used to estimate the theoretical dynamic range of gene induction in fold. In some cases, the polyA signal has a modification, such as having one, two, or more alterations in sequence compared to the standard AAUAAA sequence. For example, instead of AAUAAA, one may use another sequence, including at least AUUAAA, AGUAAA, UAUAAA, CAUAAA, GAUAAA, AAUAUA, AAUACA, AAUAGA, AAAAAG, or ACUAAA. In embodiments wherein two or more polyA signals are utilized in the construct, the polyA signals may be the same or may be different.

Figure 12A:
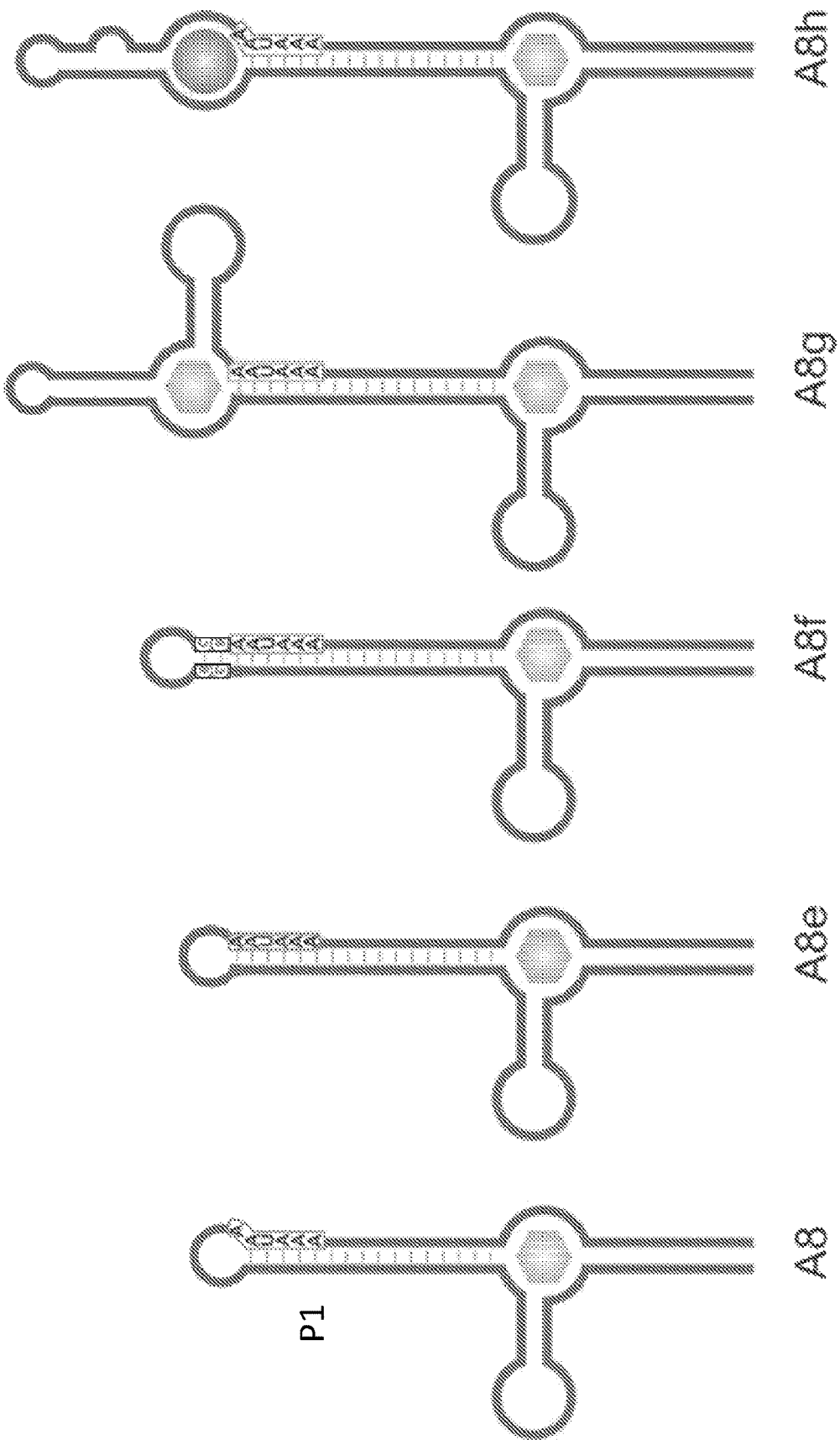
FIGS. 12A-12B show examples of modification of the P1 region based on the A8 construct.
Figure 12B:
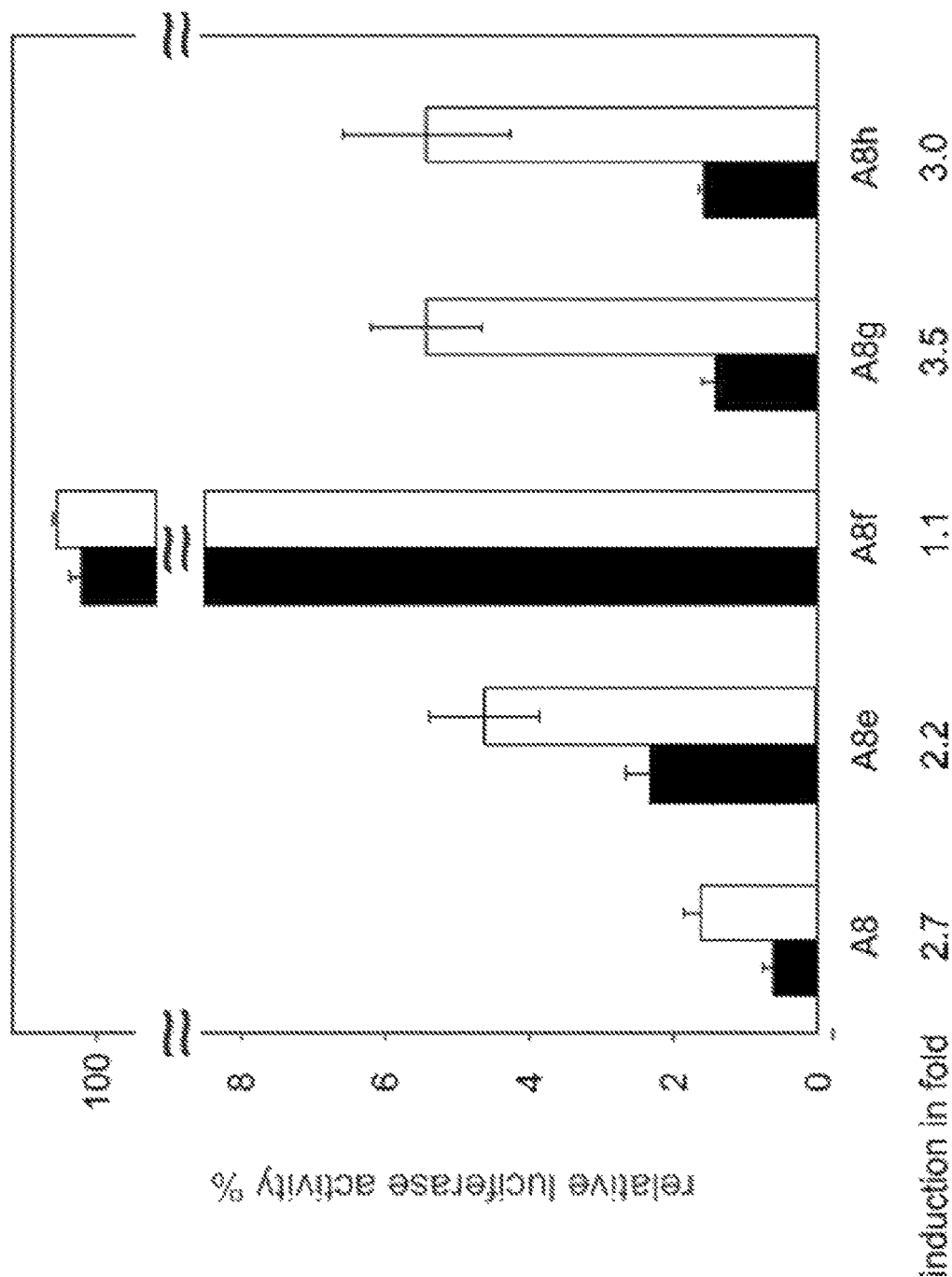
Figure 13A:
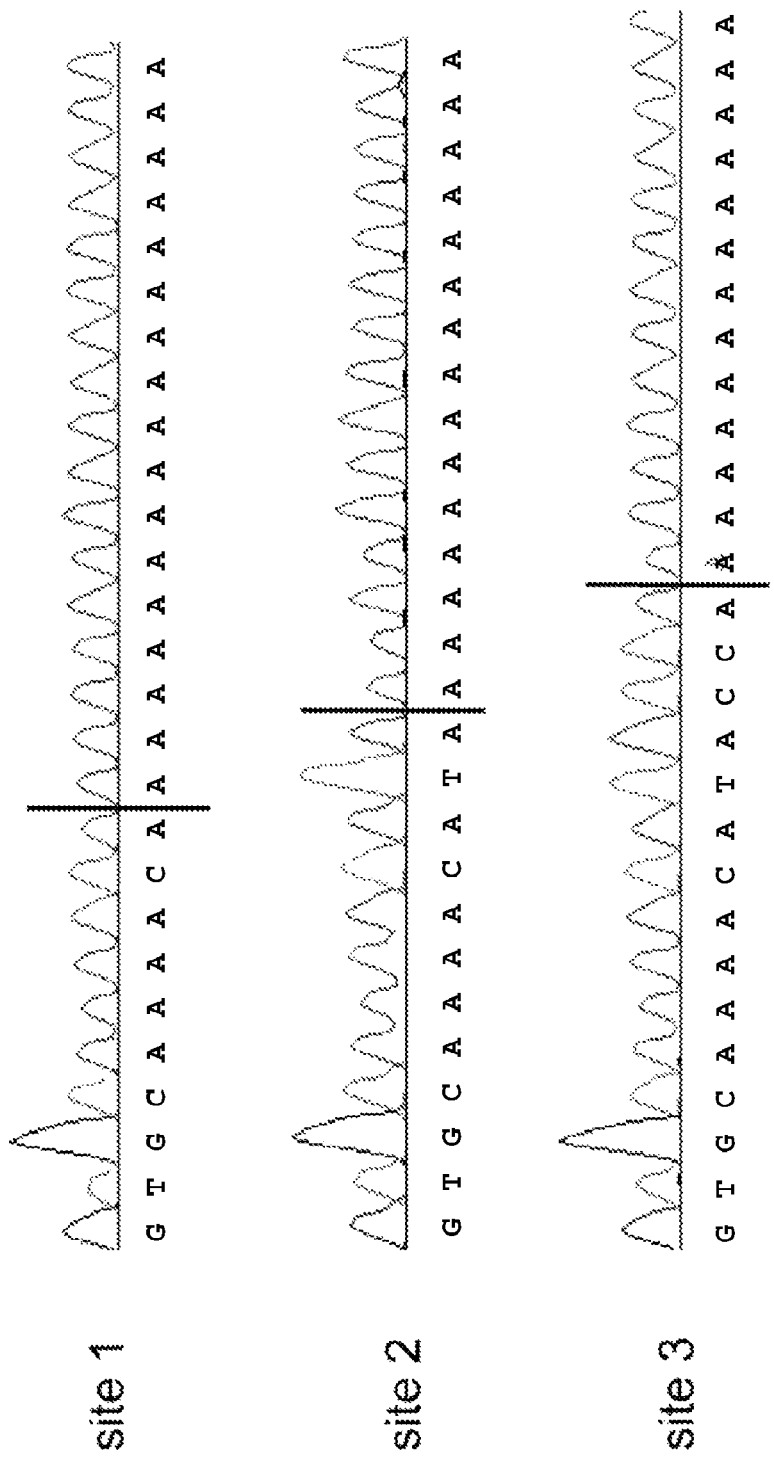
FIGS. 13A-13B show that the polyA cleavage occurs around B1-2 bulge of the tc binding core.
Figure 13B:
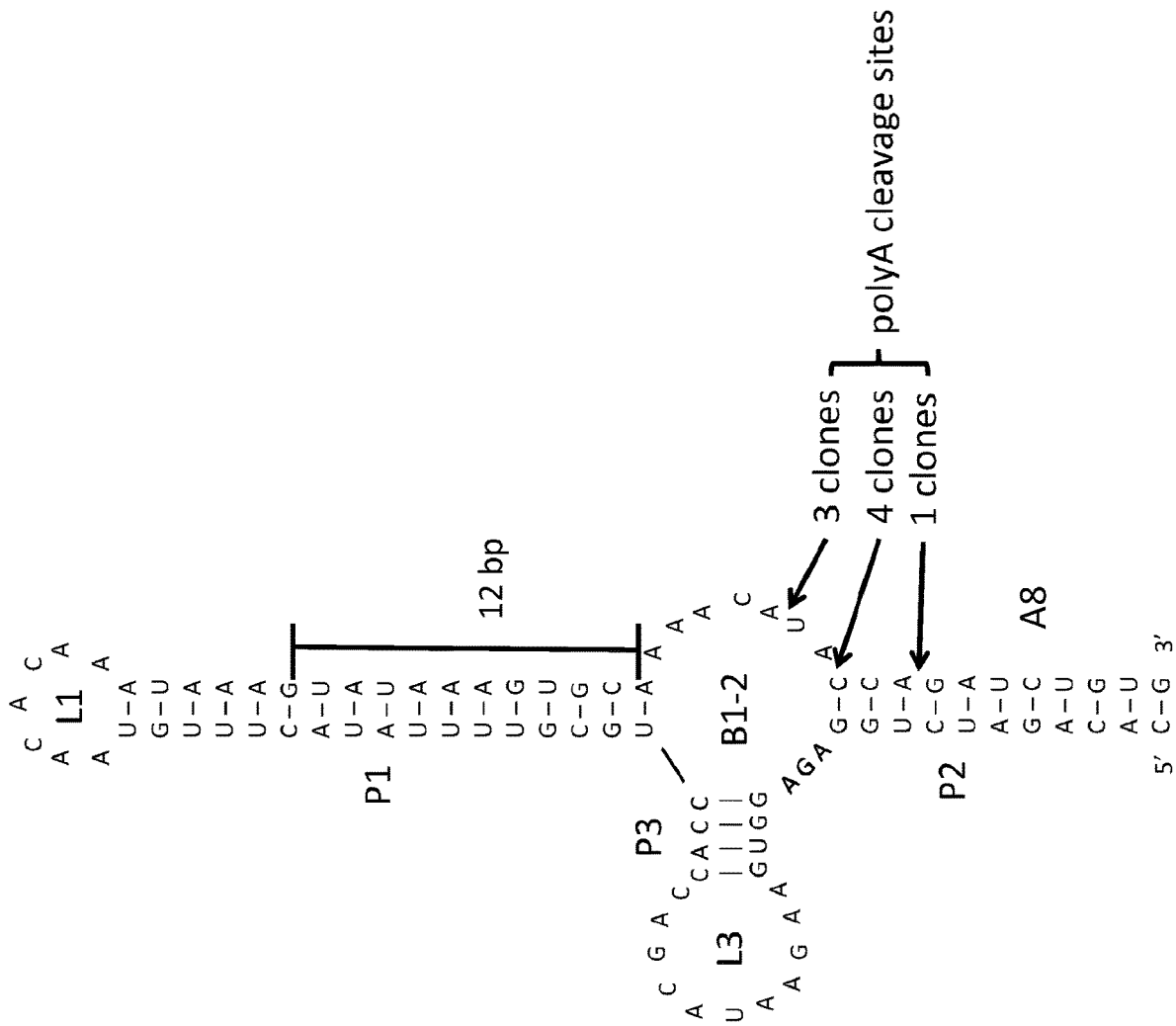
Figure 14A:
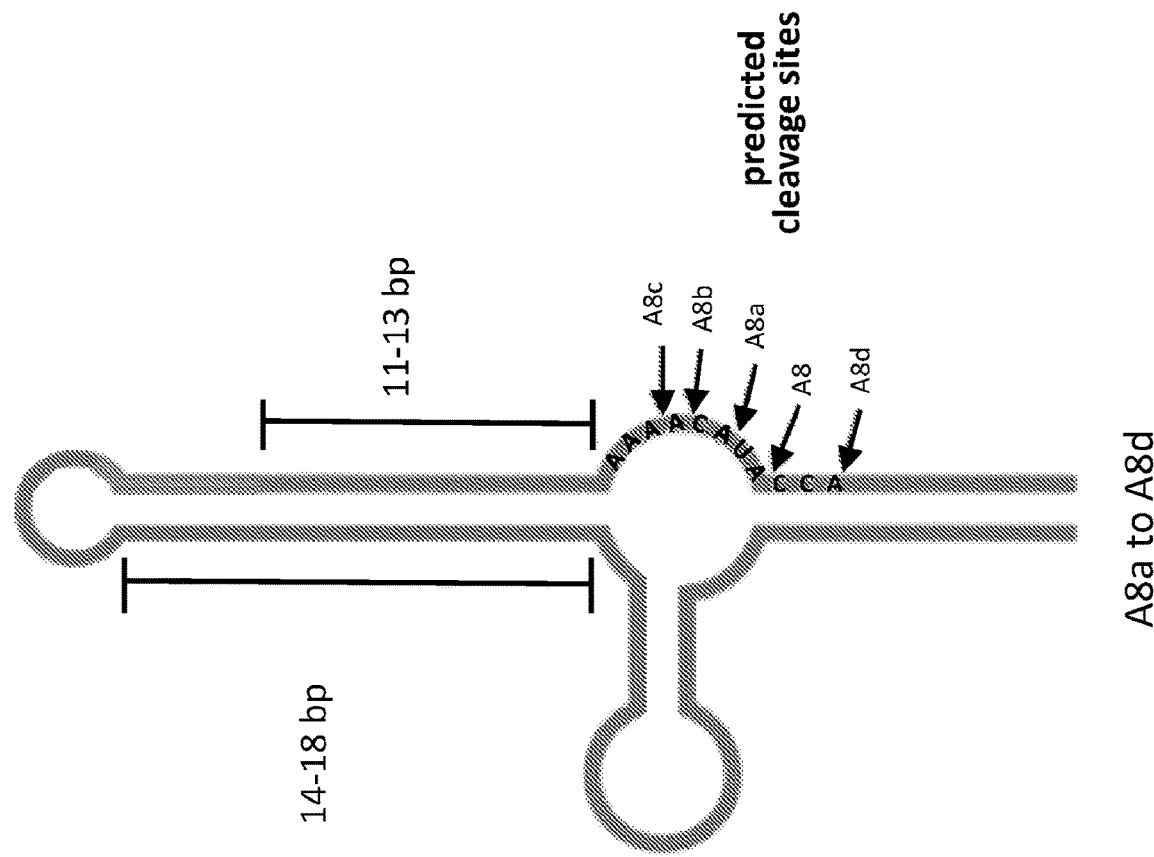
FIGS. 14A-14B show the modifications of polyA-GU distance, predacated cleavage sites, and their effect on regulation efficiency.
Figure 14B:
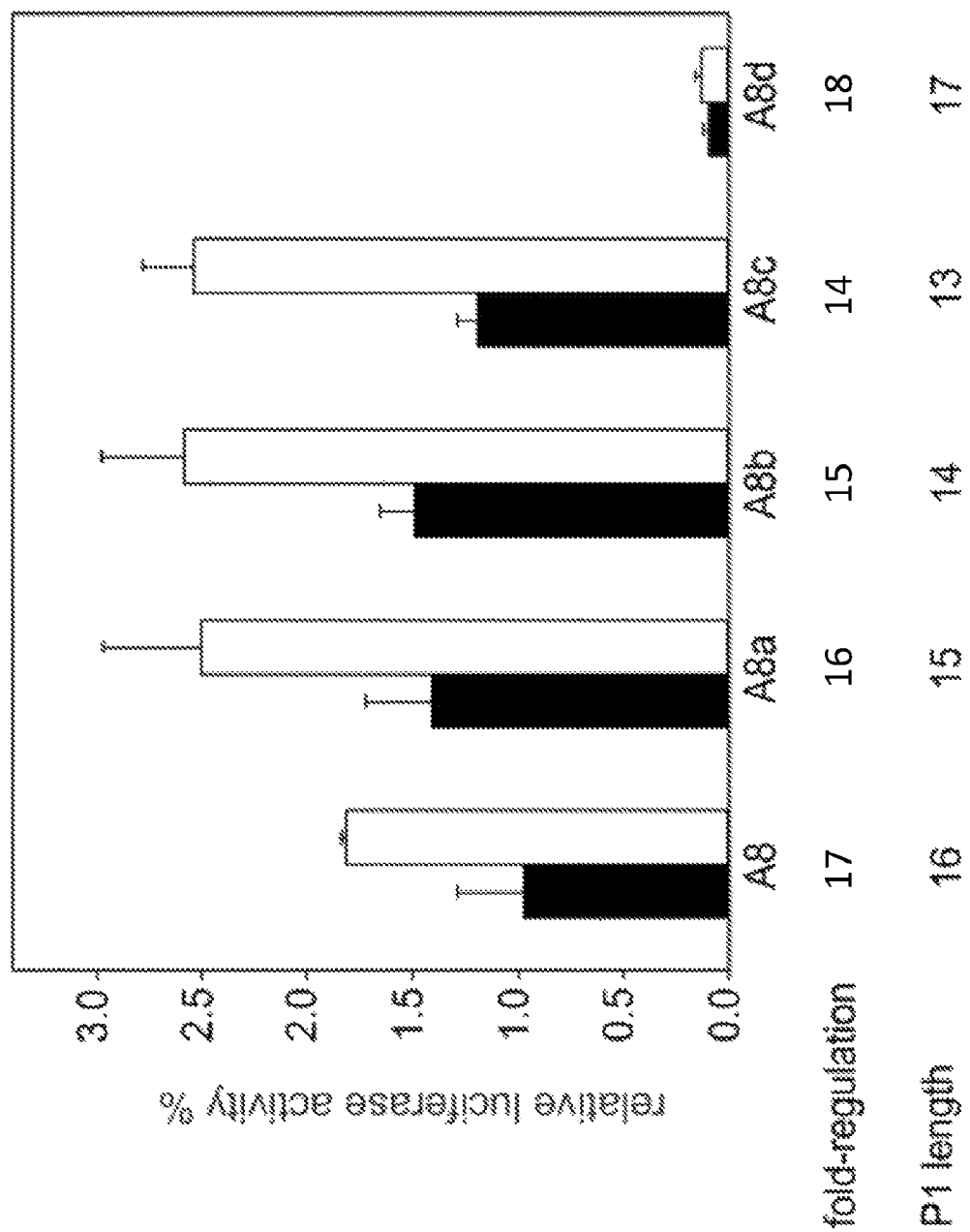
Figure 15A:
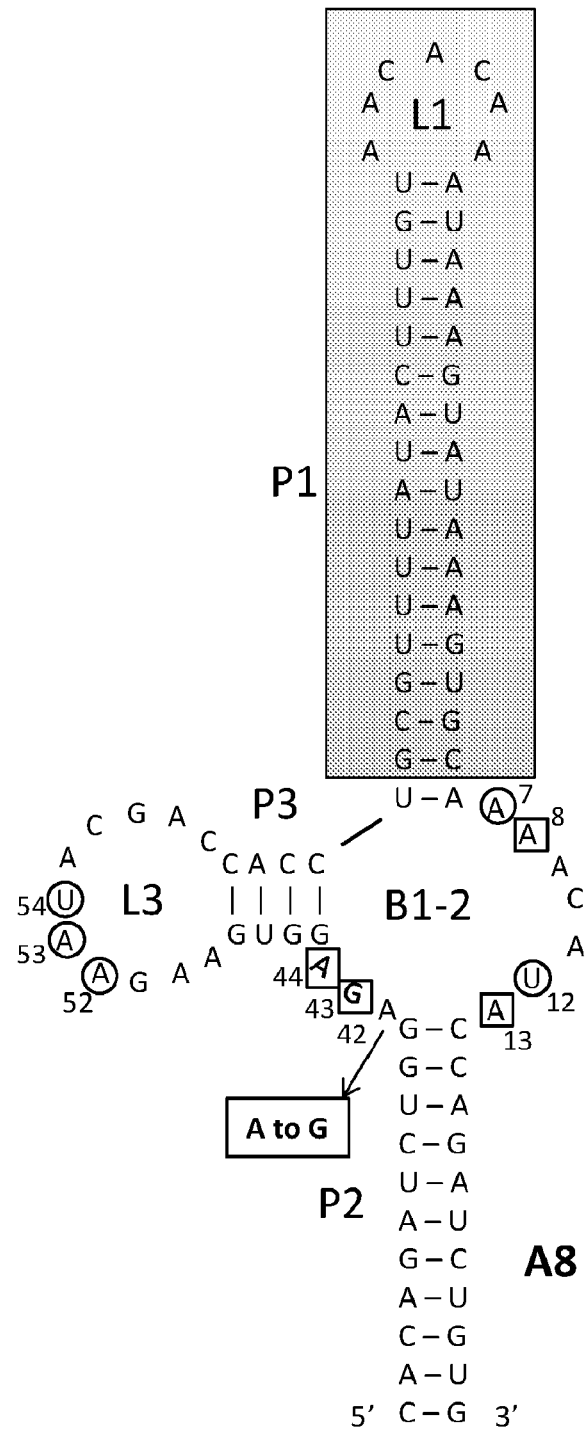
FIGS. 15A-15B show that the mutational studies on position 42 revealed a construct with better regulatory efficiency. Positions marked by square boxes are known to be intolerant to mutations, while open circles indicated positions at which all nucleotide exchanges do not influence tc binding. Position A13 and A42 forms non-canonical base paring, and were chosen for mutational studies. The results indicate that A42G mutation leads to improved regulation efficiency (construct A8-A42G)[SEQ ID NO:15]. (15B) Relative luciferase activity in the absence (closed) and presence (open bars) of 15 μg/ml tc. Regulation efficiency determined as the ratio of relative luciferase activity with and without tc is given by the numbers under the plot.
Figure 15B:
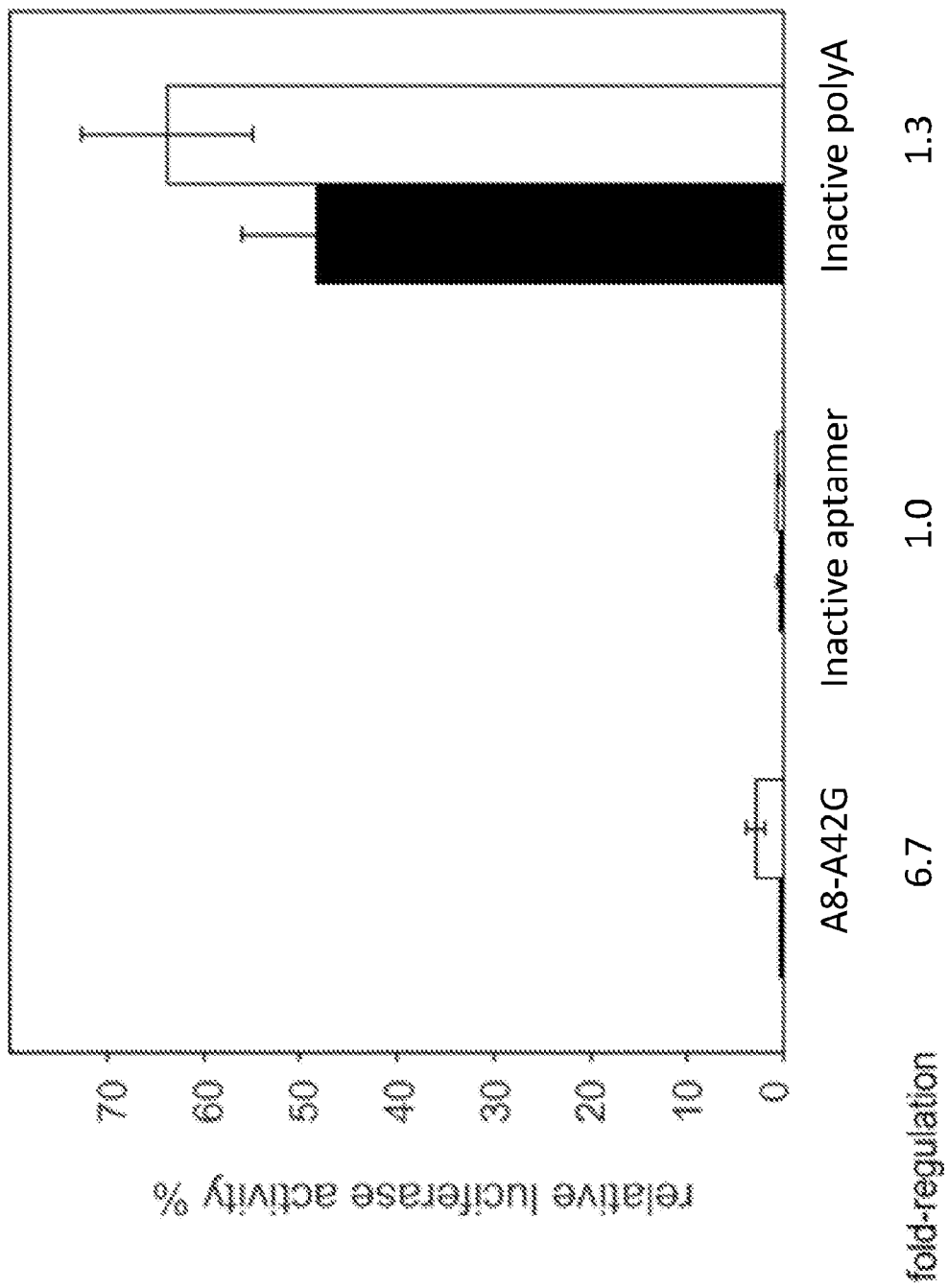
Figure 16:
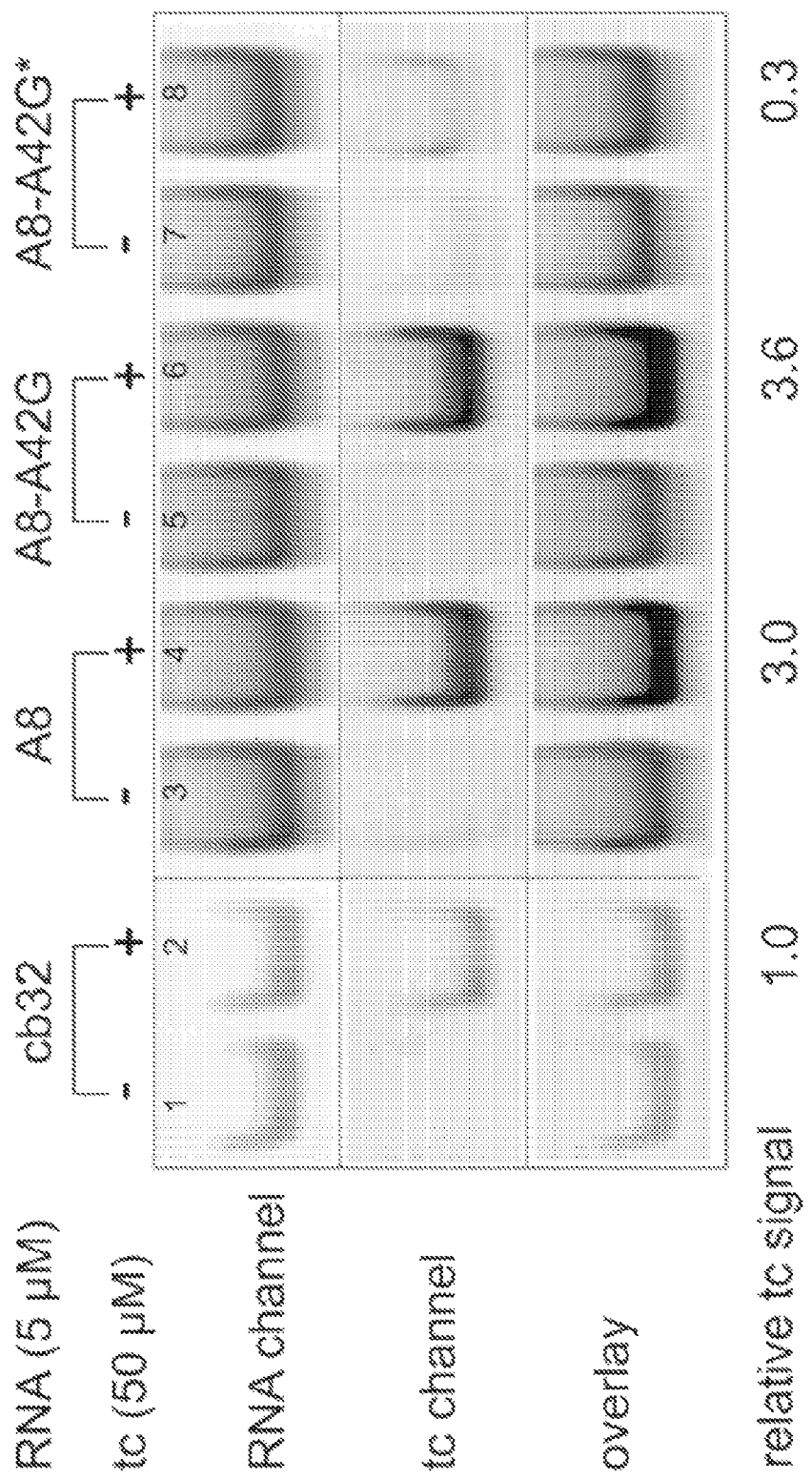
FIG. 16 shows the visualization of tc binding to the aptamer using non-denaturing gel. In vitro transcribed RNA aptamer containing the designed polyA switch (5 uM) was incubated with or without tc (50 uM) and applied to a non-denaturing 10% polyacrylamide gel. Tc was excited by UV at 365 nm and visualized directly by fluorescence emission (middle panel, blue). The gel was then incubated with SYBR gold to stain the RNA (upper panel, red). Co-localization of tc and RNA is demonstrated by the overlay (lower panel). The pixel intensity from tc channel is normalized to that of RNA channel, giving rise to the relative tc signal. Construct A8-A42G appears to have higher tc affinity as compared to A8 or to cb32. Construct A8-A42G*, which has a mutation in the tc binding site within the aptamer, results in very little tc binding.
Figure 17:
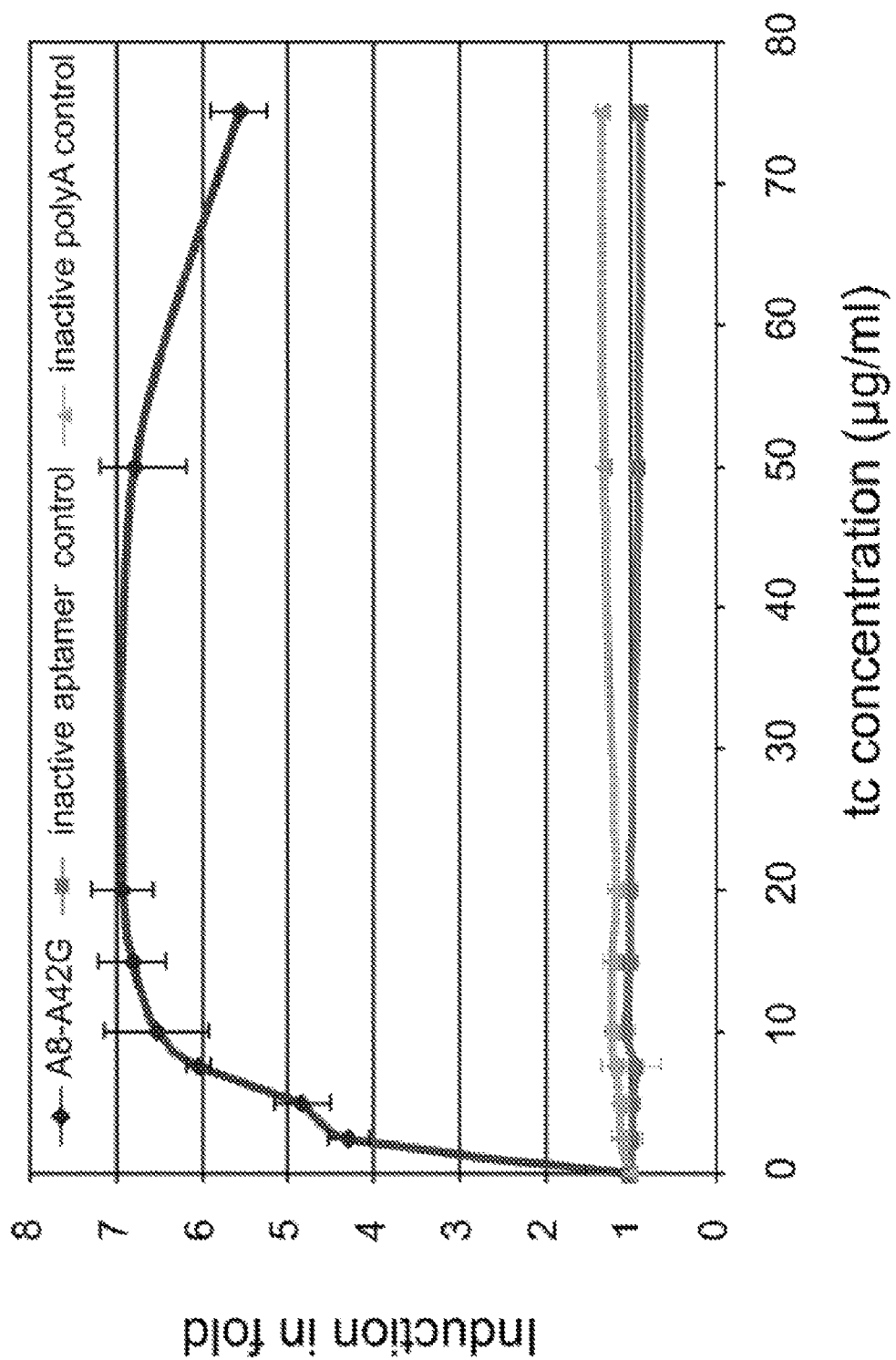
FIG. 17 demonstrates the dose-dependent regulation of A8-A42G. Relative fold induction of the A8-A42G construct (circle), the inactive aptamer control A8-A42G* (square) and the inactive pA control (AAUAAA to CACACA mutation, triangular) are shown. Each data point corresponds to a relative fold induction determined as the ratio of luciferase activity with and without tc.
Figure 18A:
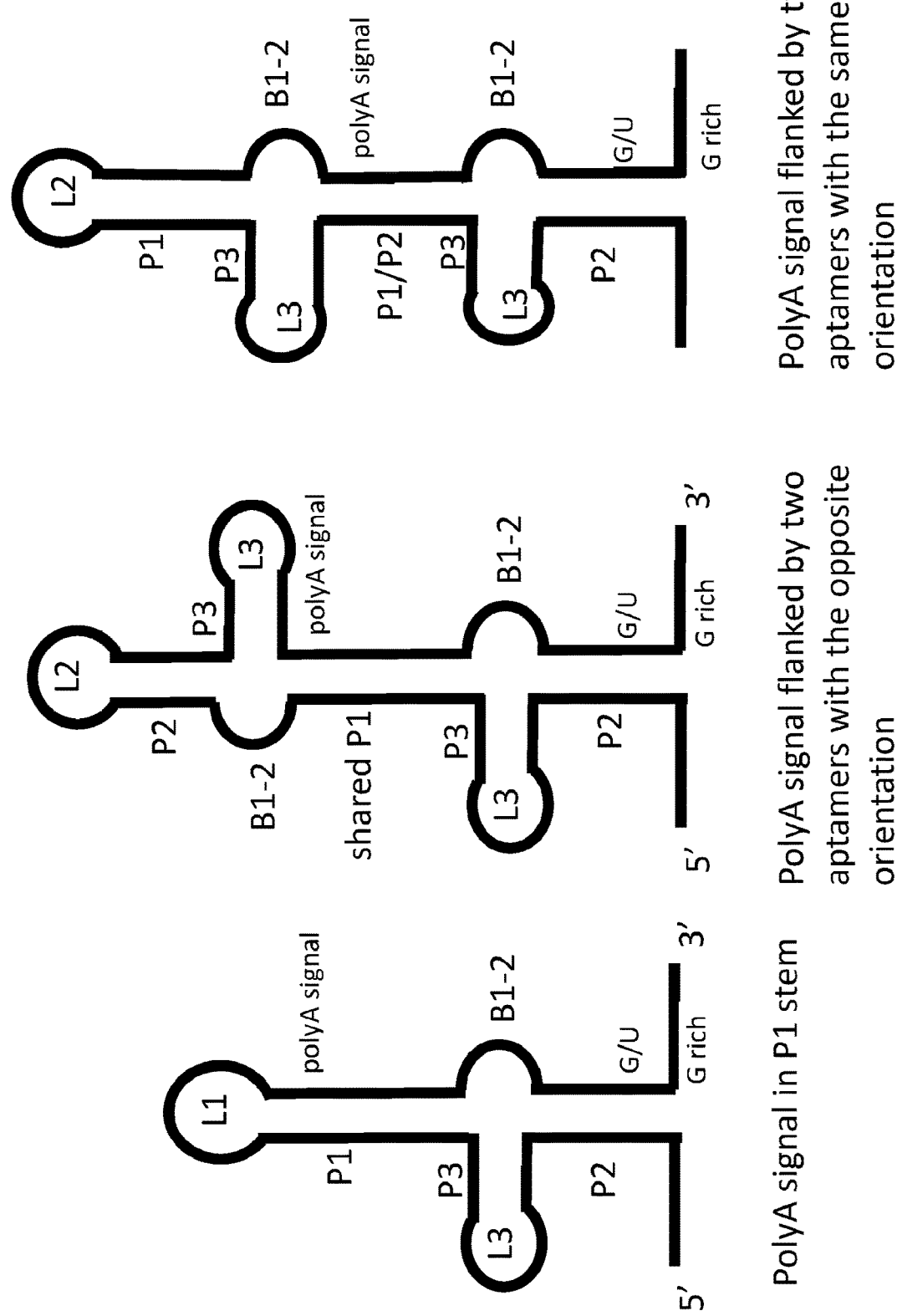
FIGS. 18A, 18B, and 18C illustrate additional PolyA switch positions as well as different aptamer configurations that allow efficient polyA cleavage and regulation.
Figure 18B:
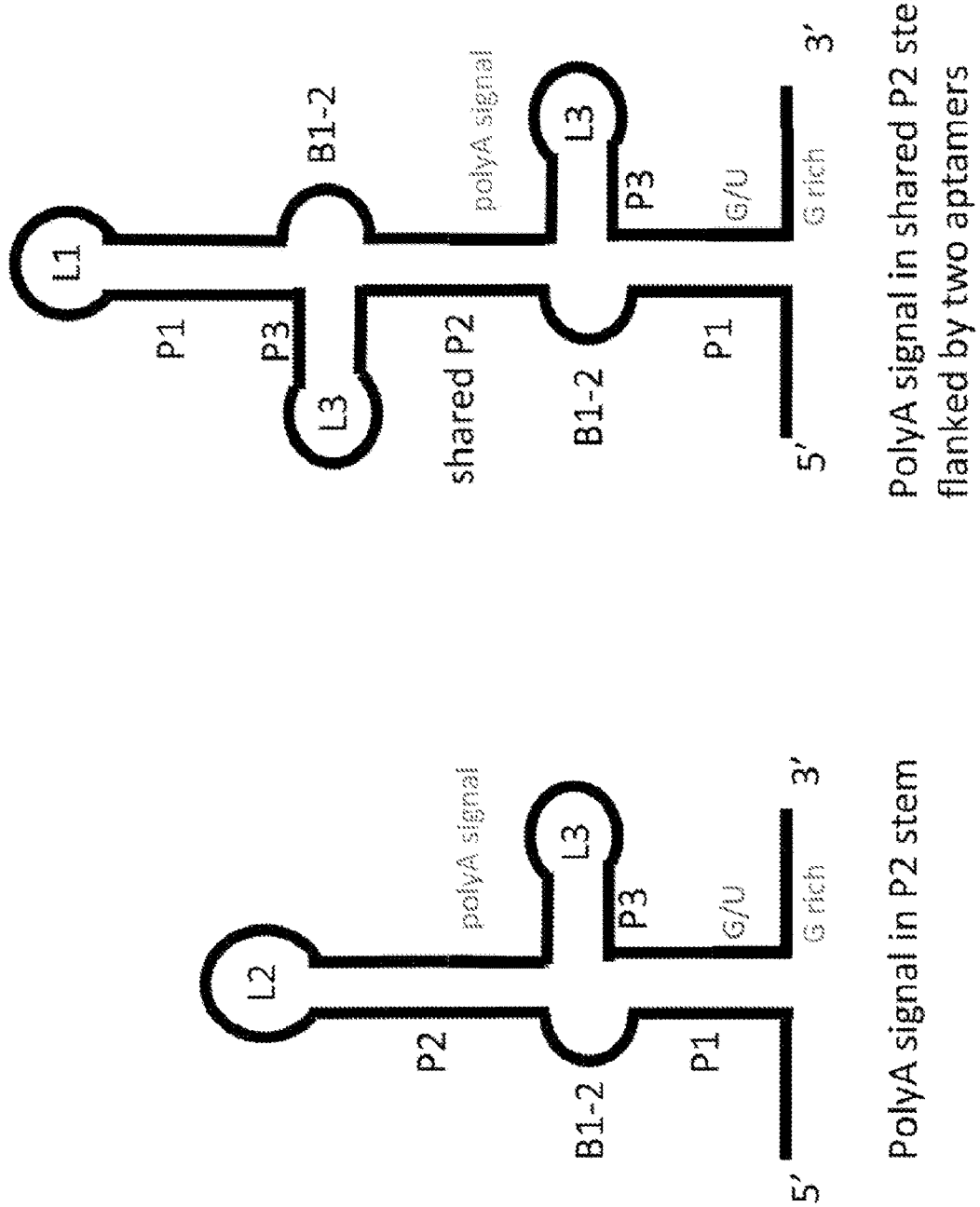
Figure 18C:
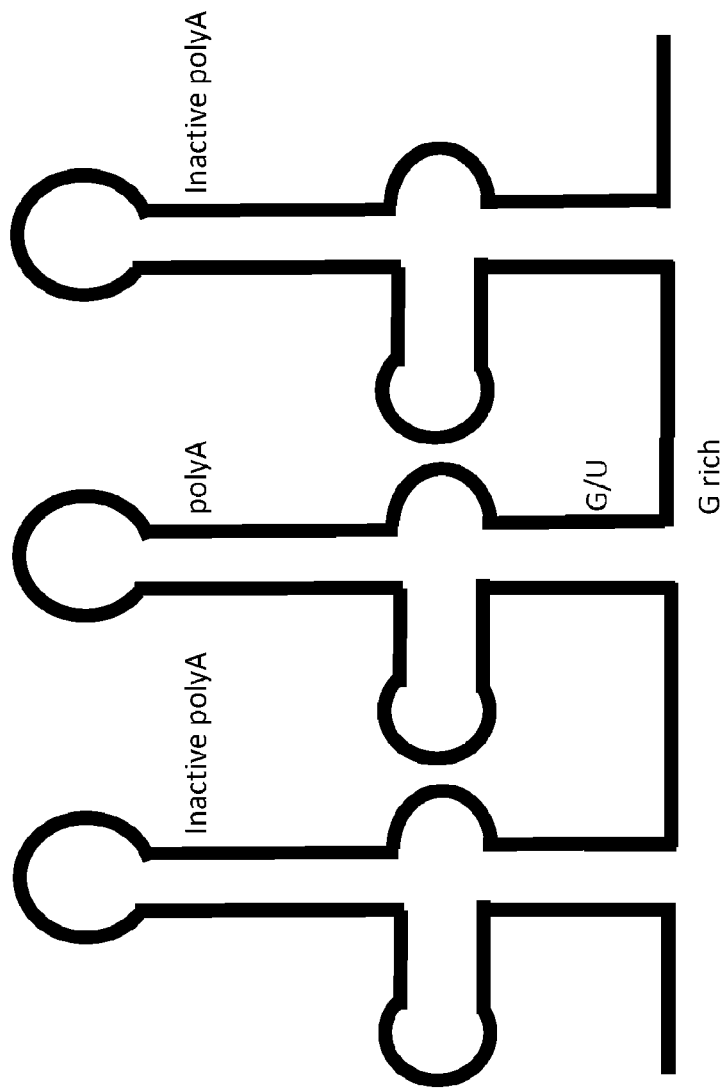

In specific embodiments, modulation of RNA structure near the polyA cleavage site is employed to enhance the activity of the polyA cleavage and/or to enhance ligand binding. In particular embodiments, placement of the polyA signal in or near the aptamer is optimized to allow improved cleavage of the polyA site and/or binding of a ligand to the aptamer (see FIG. 12, for example). The spacing of the polyA site within the aptamer may be optimized and may or may not be located generally centrally within the aptamer. The position of the polyA signal may be such that the flanking sides of the aptamer are able to be juxtaposed near each other to allow ligand binding to the aptamer (see FIG. 6 as merely an example).

In embodiments for a construct comprising the polyA signal, one or more other sequences may be utilized to enhance binding of the ligand and/or to enhance cleavage at the polyA cleavage site. In specific embodiments, a construct comprising the polyA signal also comprises one, two, three, or more G-rich regions downstream of the polyA signal. In specific embodiments, a construct comprising the polyA signal also comprises one, two, three, or more U/UG-rich regions downstream of the polyA signal. In certain embodiments, the one or more G-rich regions are downstream of at least one U/UG-rich region. The length of one or more particular stems or loops in a particular aptamer and/or the position of the polyA signal, a G-rich region, and/or a U/UG-rich region may impact regulation efficiency, in specific embodiments (FIGS. 5, 10, 13-25), and the skilled artisan may employ routine methods to optimize a suitable configuration.

The placement of the construct comprising the polyA switch may occur by any suitable means, but in specific embodiments the construct is present in a cell, tissue, or organism and may be present exogenously on a vector (such as a viral vector (adenoviral, retroviral, adeno-associated, lentiviral, and the like) or plasmid) or it may be present within the genome of a cell. Polynucleotides comprising the polyA switch and the expressible polynucleotide may be provided to a target cell, tissue, or organism as naked nucleic acid, they may be comprised within a suitable carrier (such as a liposome or nanoparticles), or they may be comprised on a vector which itself may have a suitable carrier.

Figure 8B:
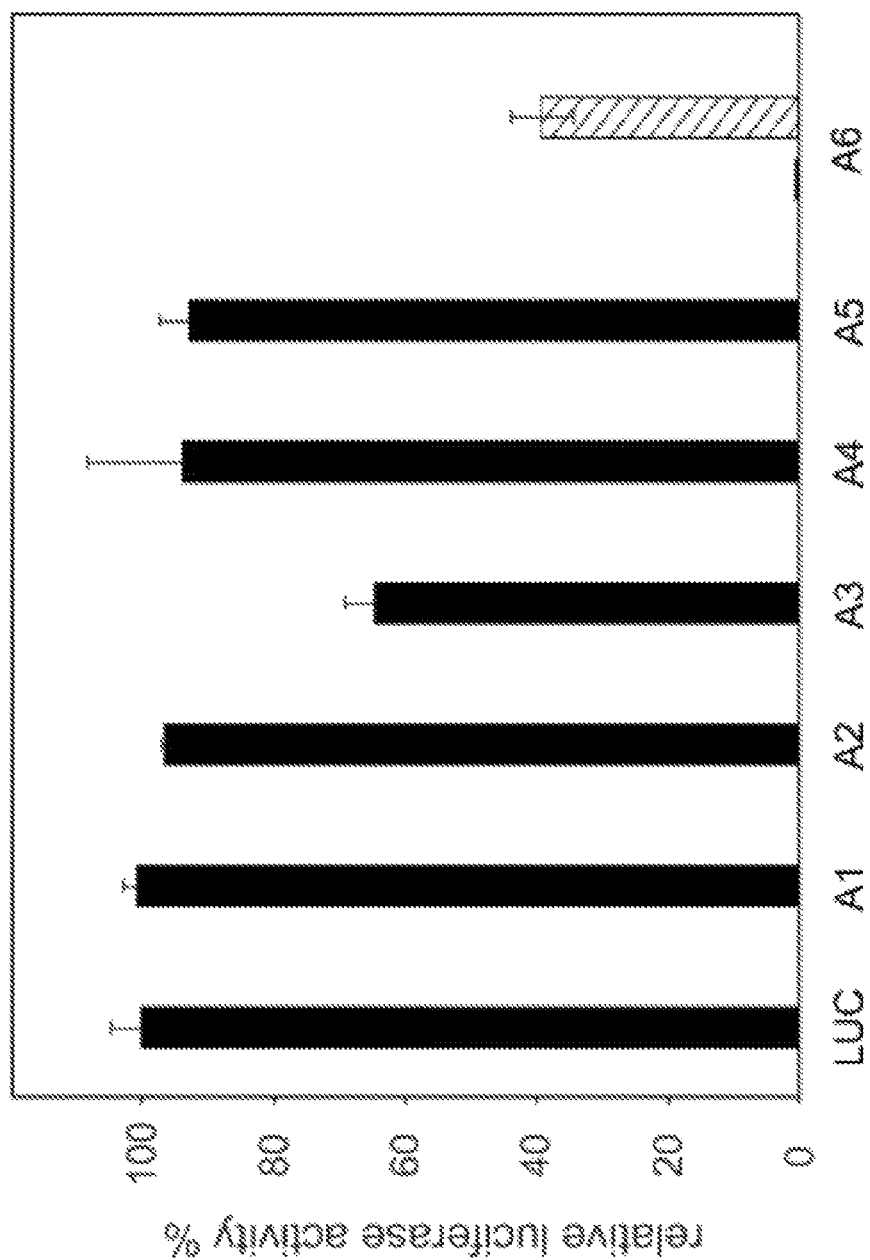
Figure 9A:
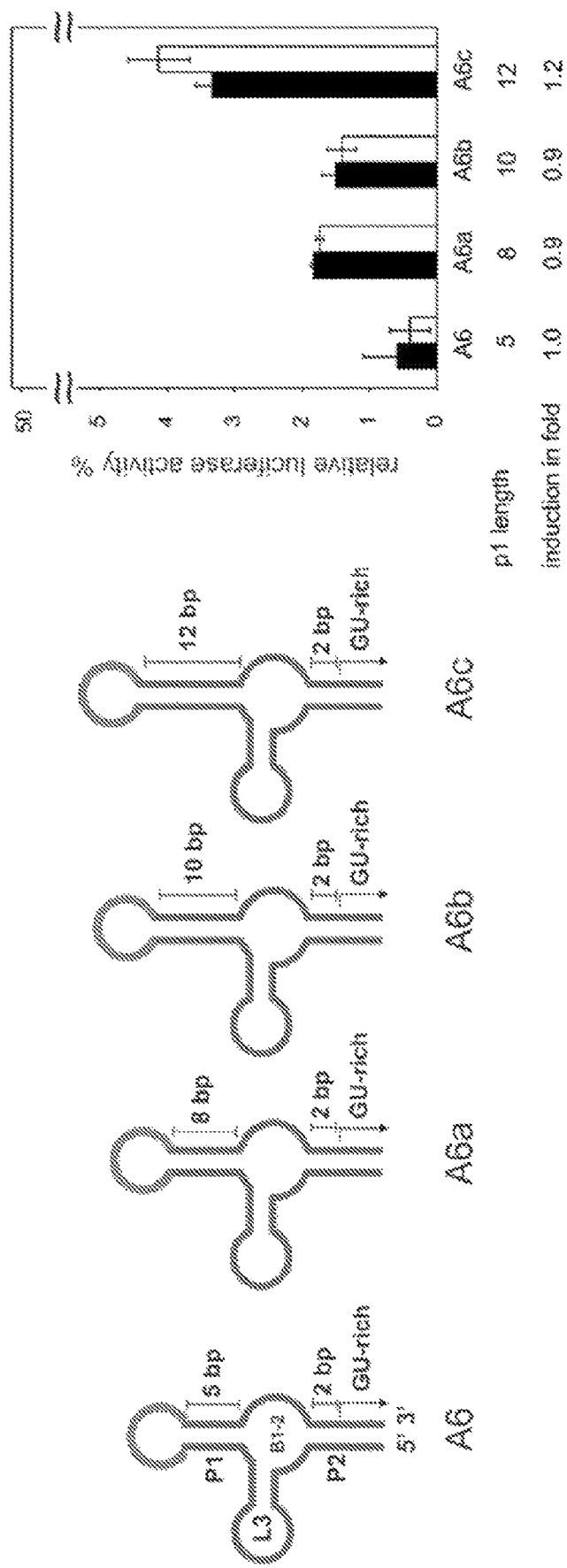

In particular embodiments, an aptamer is designed such that it binds a particular ligand, or it may be obtained from screening of a library of aptamers, or it may be modeled from an existing aptamer, for example. Different regions of the aptamer may be modified to optimize binding of the ligand and/or cleavage at the polyA site. In specific embodiments, the position of the polyA signal is related to the efficiency of polyA cleavage (see, for example, FIG. 8). In one example, aptamer A8 is modulated (see FIGS. 13-15) and the resultant effects on efficacy are considered. Again, as an example, Table 1 shows the results of mutational analysis of the ligand binding site based on the exemplary A8 aptamer.

| position | | |
|---|---|---|
| 42 | 13 | induction in fold |
| A | A | 2.6 |
| C | G | 0.7 |
| G | A | 6.8 |
| G | C | 0.8 |
| G | G | 0.7 |
| U | A | 1.0 |
| U | C | 0.8 |
| U | G | 0.7 |

The skilled artisan is aware of routine methods to generate aptamers for targeting compounds with high affinity[7-12].

In specific embodiments, a system is employed that utilizes two or more separate polyA switches. One polyA construct may be responsive to a first aptamer that binds a first ligand, and another polyA construct may be responsive to a second aptamer that binds a second ligand, in specific embodiments wherein the first and second aptamers are non-identical and wherein the first and second ligands are non-identical. In other cases, the polyA construct having multiple aptamers may be responsive to the same ligands.

Embodiments of Biosensor Systems

The disclosure provides 5' UTR polyA-based RNA switches that offer several key advantages over the existing technologies for detecting intracellular signatures in live cells, employed herein as a biosensor approach. First, it is shown herein that the reporter signal from such a sensor exhibited extremely low leaky expression in live human cells, and upon the detection of a specific ligand protein, the signal was effectively induced above a hundred fold. This signal-to-noise ratio is at least one order of magnitude higher than has been previously achieved in live human cells, giving a dynamic range that would allow new applications in a variety of experimental settings. Second, the polyA sensor enables non-invasive detection/imaging of endogenous proteins in live cells without the need for labels, tags, or stains, addressing a class of measurements that has been difficult to address previously. Lastly, by efficiently linking existing aptamer technology to current imaging reporter systems, the method enables a platform for detecting a broad range of protein ligands by molecular imaging. The polyA sensor thus offers a unique capacity for detecting molecular signatures in vivo with significantly broader applications in molecular detection than is currently possible, and could even be translated into clinic using clinically applicable reporter probe for imaging (i.e., PET, MRI, NIRF).

Such a biosensor provides spatial as well as temporal information regarding the levels of specific ligands in disease, for example, and the input information can be used to regulate cellular behavior for achieving therapeutic goals. For example, an example of a polyA biosensor is one that is engineered to recognize glucose as its ligand, and in response, regulates the expression of an engineered insulin protein to modulate the glucose levels in diabetic patients. Similar polyA biosensors can also function as safety switches. For example, a biosensor can be engineered to detect the presence of a cancer biomarker in stem cells. When a normal stem cell erroneously transforms into a cancer cell, the biosensor would switch on a suicidal gene for self-destruction.

In specific embodiments, examples of ligand molecules for the polyA-based switch when employed in a biosensor system include at least cellular metabolites; nucleic acids (including regulatory nucleic acids, such as miRNAs or RNA interfering molecules (shRNA or siRNA)); small molecules; cellular proteins (for example, proteins associated with a disease state, including cancer proteins, for example) or viral proteins produced by viral infection.

In some embodiments, the expressible polynucleotide encodes a reporter gene product, or a therapeutic gene product. In some embodiments, the reporter gene product may be fused to a therapeutic gene product as a fusion protein. In other embodiments, the expression of the reporter gene product and the therapeutic gene product are translated separately from a single mRNA using an IRES. Examples of reporter genes include luciferase, green fluorescence protein, red fluorescence protein, β-galactosidase, and so forth. Examples of therapeutic genes include insulin, growth hormones, dystrophin, albumin, factor IX, and so forth. In other cases, the system utilizes an expressible polynucleotide that encodes the reporter gene product and a separate expressible polynucleotide that encodes the therapeutic gene product, and their expression may be governed by the same or a different ligand-binding aptamer. The construct(s) for the reporter gene product and the therapeutic gene product may be on the same vector or on different vectors.

In certain embodiments, the polynucleotide comprises 2, 3, 4, 5, or more aptamers operably linked in a linear manner in a 5' to 3' direction. The aptamers may or may not have substantially the same sequence or structure and each may or may not comprise a polyA signal. When multiple polyA signals are present within one aptamer or within multiple aptamers, the polyA signals may or may not be identical. In particular embodiments, a single polynucleotide comprises multiple aptamers but comprises only one G rich region and that G rich region may in some cases be present on any aptamer on the polynucleotide but in specific cases is present on the second aptamer in a 5' to 3' direction of the polynucleotide or is on the 3'-most aptamer of the molecule. The folding of a polynucleotide comprising two or more aptamers may vary depending on a variety of factors, including length of the polynucleotide and sequence thereof, but in specific cases a single polynucleotide is able to act via more than one folding configuration. In specific embodiments, the polynucleotide is configured such that the aptamers do not have any base pairing between aptamers (for example, the left image in FIG. 26), although in other cases there is at least some base pairing between aptamers (including along the majority of sequence of the aptamers), for example the right image in FIG. 26. In some folding configurations, a stem loop of one aptamer is configured opposite the stem loop of another aptamer in the same molecule (see right image of FIG. 26).

In some embodiments, a polynucleotide comprising two or more aptamers are separated linearly in a 5' to 3' direction by a certain sequence. The certain sequence may be random or may be defined, such as a G-rich region. In specific cases, the length linearly in a 5' to 3' direction between two loops is of a particular length. For example, the number of nucleotides between two loops may be 10-25, 10-24, 10-23, 10-22, 10-21, 10-20, 10-19, 10-18, 10-17, 10-16, 10-15, 10-14, 10-13, 10-12, 10-11, 11-25, 11-24, 11-23, 11-22, 11-21, 11-20, 11-19, 11-18, 11-17, 11-16, 11-15, 11-14, 11-13, 11-12, 12-25, 12-24, 12-23, 12-22, 12-21, 12-20, 12-19, 12-18, 12-17, 12-16, 12-15, 12-14, 12-13, 13-25, 13-24, 13-23, 13-22, 13-21, 13-20, 13-19, 13-18, 13-17, 13-16, 13-15, 13-14, 14-25, 14-24, 14-23, 14-22, 14-21, 14-20, 14-19, 14-18, 14-17, 14-16, 14-15, 15-25, 15-24, 15-23, 15-22, 15-21, 15-20, 15-19, 15-18, 15-17, 15-16, 16-25, 16-24, 16-23, 16-22, 16-21, 16-20, 16-19, 16-18, 16-17, 17-25, 17-24, 17-23, 17-22, 17-21, 17-20, 17-19, 17-18, 18-25, 18-24, 18-23, 18-22, 18-21, 18-20, 18-19, 19-25, 19-24, 19-23, 19-22, 19-21, 19-20, 20-25, 20-24, 20-23, 20-22, 20-21, 21-25, 21-24, 21-23, 21-22, 22-25, 22-24, 22-23, 23-25, 23-24, or 24-25 nucleotides. The number of nucleotides between two loops in an aptamer or in a polynucleotide may be 10, 11, 12, 13, 14, 15, 16, 17, 18, 19, 20, 21, 22, 23, 24, or 25. In specific cases, in a configuration of multiple aptamers wherein there is base pairing between at least part of two different aptamers, the distance between one loop and another, and including the stem loop 2 sequence of the aptamer (see FIG. 26) is between 10-25 nucleotides, including 18-20 nucleotides, for example.

Methods of Use of Biosensor Systems

In embodiments of the disclosure, there are methods of utilizing systems of the disclosure for sensing or detecting a particular desired biological state, including, for example, for detecting the presence or absence of one or more compositions in a certain location or environment, including certain cells, tissues, and/or an organism. The biosensor system may provide information in a spatial and/or temporal manner about a particular environment or location. The biosensor system may provide information about a particular disease state or susceptibility or risk thereof. The biosensor system may be used in methods of determining whether or not an individual has a particular disease or is at risk of having a particular disease or whether or not an individual will respond to a therapy for a disease. The biosensor system may provide information whether or not a certain therapy is effective in an individual.

In particular embodiments, the ligand for the biosensor system is endogenous to a cell, tissue, or individual. The ligand may or may not be endogenously expressed at all times and in all tissues. The endogenous ligand may be expressed in a tissue-specific or temporal-specific manner. In certain embodiments, a vector comprising polynucleotides of the system are targeted to a certain tissue or region in an individual wherein the tissue or region is suspected of having or not having a particular endogenous ligand.

In embodiments wherein the biosensor system is utilized, the expression of the expressible polynucleotide may be regulated by one or more entities other than the polyA switch. That is, in some cases there may be one or more transcriptional elements that permit or inhibit expression in certain environments or at certain temporal settings (such as certain states of biological development or disease stages). In cases wherein expression of the polyA switch system is desired to occur in a certain environment, expression of the polynucleotide may be regulated by a tissue-specific promoter. The selection of the tissue-specific promoter may be dictated by the environment in question, and examples of tissue-specific promoters are known in the art and may be accessible, for example, at databases such as TiProD.

In cases wherein it is desirable to determine whether one or more therapies are effective in an individual, the system may be employed in the individual before the therapy is provided, such as to detect the presence or absence of a specific indicative compound for the therapy, and then after the therapy is provided one or more times the system may be employed in the individual to detect the presence or absence of the specific indicative compound. In other embodiments, the system is not employed for monitoring therapy until after the therapy is provided one or more times to the individual, such as to identify the presence or absence of a specific compound that is indicative of the efficacy of the therapy.

In some cases the biosensor system is employed to provide information, but in other embodiments the biosensor system may be utilized for therapeutic purposes (and optionally may provide information as well). For example, the system may be able to recognize a metabolite as a ligand and upon binding of the metabolite ligand to the aptamer permits expression of a gene product that provides therapy for a medical condition to which the metabolite is a marker (or its presence or levels are indicative of the medical condition or susceptibility thereto). In other embodiments, the expressible polynucleotide is not a therapeutic gene product itself but is a suicide gene product that is expressed when there is a ligand present that is indicative of a deleterious medical condition or susceptibility or risk thereof; in specific embodiments, the ligand becomes present in cells that are cancerous or pre-cancerous, for example.

Examples of ligands that may regulate aptamers in biosensor systems of the disclosure include at least cellular metabolites, small RNAs (such as miRNAs), normal and aberrant cellular proteins, foreign proteins expressed by virus and other pathogens, suicidal proteins that induce cell death, and so forth.

Examples of ligands that may regulate aptamers in biosensor systems of the disclosure include at least cellular metabolites, small RNAs (such as miRNAs), cellular proteins, and so forth.

Embodiments of Gene Regulation Systems

The ability to control gene expression has always been useful in order to elucidate the function of a specific gene product, or to manipulate the levels of a specific protein to achieve therapeutic effects. In embodiments of the disclosure, when a polyA switch is embedded in the 5'UTR of the mRNA, the cleavage of polyA signal leads to destruction of the mRNA and therefore a loss of transgene expression. Small drug-like molecules (for example) capable of inhibiting the polyA switch result in preservation of the intact mRNA, and therefore induce gene expression. As described elsewhere herein, transgene expression controlled by such a switch exhibited extremely low leaky expression in live human cells, and upon the administration of a small molecule (tetracycline in this case), the transgene expression was effectively induced above 30-fold. Optimization and generalization of this gene regulation system may be performed to lead to the generation of many tailor-made gene regulation systems, each controlled by a ligand such as an FDA-approved small molecule drug, for example. In contrast to current gene regulation systems based on the control of transcription using transactivators, the polyA based system described herein does not require the expression of any protein transactivator products (that may cause severe host immune response) and is not dependent upon the use of any specialized promoter elements, and therefore represents a 'portable' regulation system that could be 'embedded' into any endogenous gene or engineered vector transcription unit. As such, the system requires only one transcriptional unit (one expression construct), and is promoter flexible so that it can be used to regulate transgenes in a tissue-specific (spatial) and temporal manner. Such gene regulation systems, combining safe small molecules with RNA-based non-immunogenic polyA switches, would be significantly safer to use in clinical applications as well as in biological studies.

In specific embodiments, gene regulation systems utilize small compounds as ligand molecules for polyA-based switches. Examples of small compounds include tetracycline or tetracycline analogs (such as doxycycline, demeclocycline, minocycline, chloro-tetracycline, sancycline, metacycline, or tigecycline, for example) or functional derivatives thereof; aminoglycosides or functional derivatives thereof; rapamycin or functional derivatives (everolimus, temsirolimus, deforolimus, ridaforolimus, for example) thereof; and FDA-approved drugs or functional derivatives thereof. In other embodiments of the gene regulation systems, a ligand other than a small molecule is employed, such as a protein, peptide, nucleic acid, and so forth, and in specific embodiments the ligands of the system are provided in a suitable carrier.

In certain embodiments, a gene regulation system utilizes two or more aptamers to individually respond to different ligands, for example, different tetracycline analogs. That is, if one polyA switch system can be made to respond to a ligand such as tetracycline, then many tailor-made gene regulation systems can be generated by mutating aptamer RNA sequence to respond to different tetracycline analogs (doxycycline, etc.).

In some embodiments, the expressible polynucleotide encodes a reporter gene product, or a therapeutic gene product. In some embodiments, the reporter gene product may be fused to a therapeutic gene product as a fusion protein. In other embodiments, the expression of the reporter gene product and the therapeutic gene product are translated separately from a single mRNA using an IRES. Examples of reporter genes include luciferase, green fluorescence protein, red fluorescence protein, β-galactosidase, and so forth. Examples of therapeutic genes include insulin, growth hormones, dystrophin, albumin, factor IX, and so forth. In other cases, the system utilizes an expressible polynucleotide that encodes the reporter gene product and a separate expressible polynucleotide that encodes the therapeutic gene product, and their expression may be governed by the same or a different ligand-binding aptamer. The construct(s) for the reporter gene product and the therapeutic gene product may be on the same vector or on different vectors.

Methods of Use of Gene Regulation Systems

In specific embodiments, the system of the disclosure may be used for gene regulation applications wherein a particular expressible polynucleotide is desired to be expressed in a particular location and/or at a particular event or time. In certain embodiments the control of the gene expression allows determination of function of a specific gene product, whereas in other embodiments the control of the gene expression provides a therapeutic benefit. In certain cases the expressible polynucleotide of the transgene is not desired to be expressed (such as at certain times and/or locations) and the ligand either may not be provided along with the transgene or its expression may be inhibited until the ligand is desired to be expressed to allow binding to the aptamer of the transgene for its expression (for example, with certain regulatory elements).

In certain embodiments the ligand for the gene regulatory system embodiments is not endogenous to a particular cell, tissue, or organism. In particular embodiments, the ligand in systems for gene regulation is a drug or drug-like molecule (in at least some embodiments, drug-like is defined as small molecule compounds typically with molecular weights below 500 daltons). In particular embodiments the ligand in the gene regulation systems is provided to the individual in one of any suitable manners, such as orally, intramuscularly, by inhalation, and so forth.

In certain embodiments, the polyA switch-based gene regulation systems can be configured as autoregulation systems with negative and positive feedback loops. Regulation of a gene by its own product is known as autoregulation, which can generate unique properties for applications. The polyA switch can be configured to function as an autoregulation system, in specific embodiments. That is, the product of a gene under the control of the polyA switch can positively or negatively regulate its own expression. Negative autoregulation occurs when the gene product represses its own expression. This is known to increase the robustness of the steady-state expression and reduces fluctuations in gene expression levels in cells. (1) One example of negative autoregulation that can be configured with a polyA switch is a biosensor system designed to detect glucose. In this case, the polyA switch is engineered with an aptamer that recognizes glucose as its ligand, and in response to glucose binding, turns on the expression of a transgene coding for insulin protein. The induced insulin expression reduces the glucose levels, which in turn reduces the expression of insulin. In contrast, positive autoregulation occurs when a gene product promotes its own expression. This is known to create a bi-stable state. That is, once the transgene is activated by its ligand, it can be locked into a state of high expression and keeps itself ON, even after the original input ligand has vanished (2-6). One example of positive feedback system that can be configured with polyA switch is a biosensor system designed to detect viral tat protein. In this case, the polyA switch is engineered with an aptamer that recognizes tat as its ligand, and in response to tat binding, turns on the expression of a transgene coding for tat protein. The initial introduction of tat protein induces the expression of more tat proteins. This establishes a positive feedback loop and locks the system into a state of high expression and keeps itself ON.

Kits of the Disclosure

Any of the compositions described herein may be comprised in a kit. In a non-limiting example, any polynucleotides, ligands, or vectors encompassed by the disclosure may be comprised in a kit.

The kits may comprise a suitably aliquoted composition(s) of the present disclosure. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the containers in close confinement for commercial sale. Such containers may include injection or blow-molded plastic containers into which the desired vials are retained, for example.

When the components of the kit are provided in one and/or more liquid solutions, the liquid solution is an aqueous solution, with a sterile aqueous solution being particularly preferred. The compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES

The following examples are included to demonstrate preferred embodiments of the disclosure. It should be appreciated by those of skill in the art that the techniques disclosed in the examples that follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Figure 2:
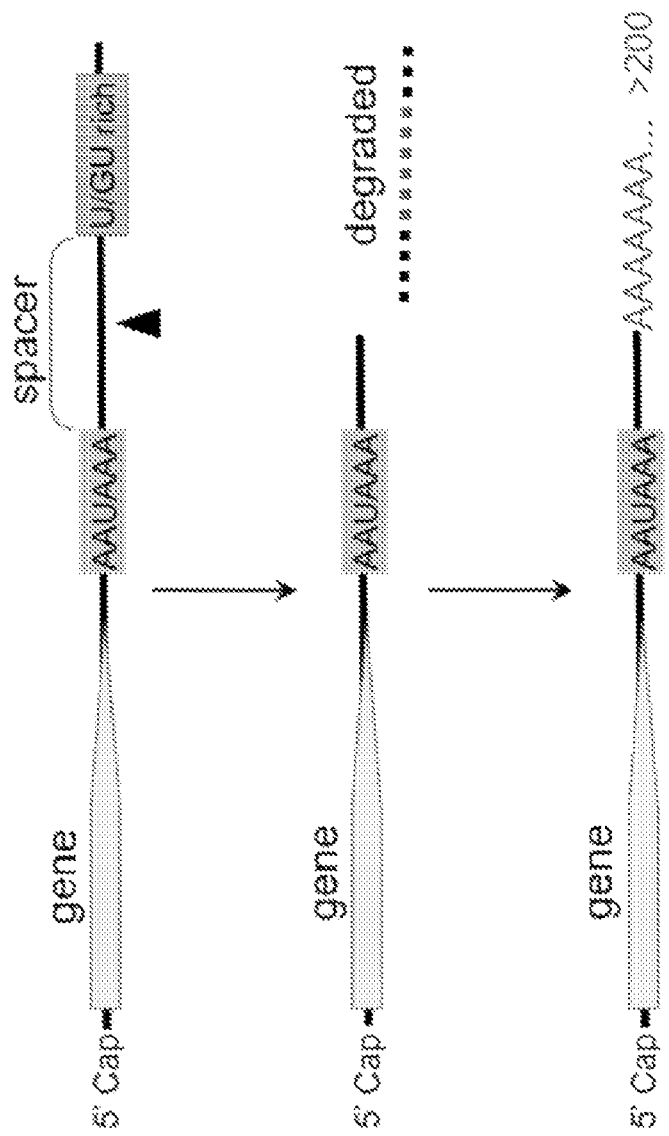
FIG. 2 illustrates that polyadenylation that normally occurs at the 3'UTR involves mRNA cleavage, addition of polyA tail to the 5' fragment, and degradation of the 3' fragment.

Innovation of the Disclosure
Harnessing the Power of polyA Cleavage to Create an Intracellular Sensor System Polyadenylation is an essential mRNA processing mechanism that is universally present in all mammalian cells. With the exception of histone genes, all mammalian protein-coding mRNAs contain a 3' end consisting of around 200-300 adenosine residues[30,31]. Formation of the polyA tail involves two sequential steps: cleavage of the pre-mRNA, and the subsequent addition of polyA tail to the newly cleaved 3' end. This polyadenylation process is directed by sequence elements present on the pre-mRNA, and by the polyadenylation machinery consisting of many multimeric protein factors. Prior to the addition of polyA tail, the pre-mRNA must be cleaved. The site of cleavage lies between the highly conserved AAUAAA signal and a downstream U- or GU-rich motif (FIG. 2). Cleavage occurs preferentially after an 'A' nucleotide[32]. Importantly, the cleaved 3' RNA fragments are quickly degraded due to the missing cap structure.

Figure 1C:
FIG. 1C shows a detailed view of the polyA components engineered within the aptamer.
Figure 3:
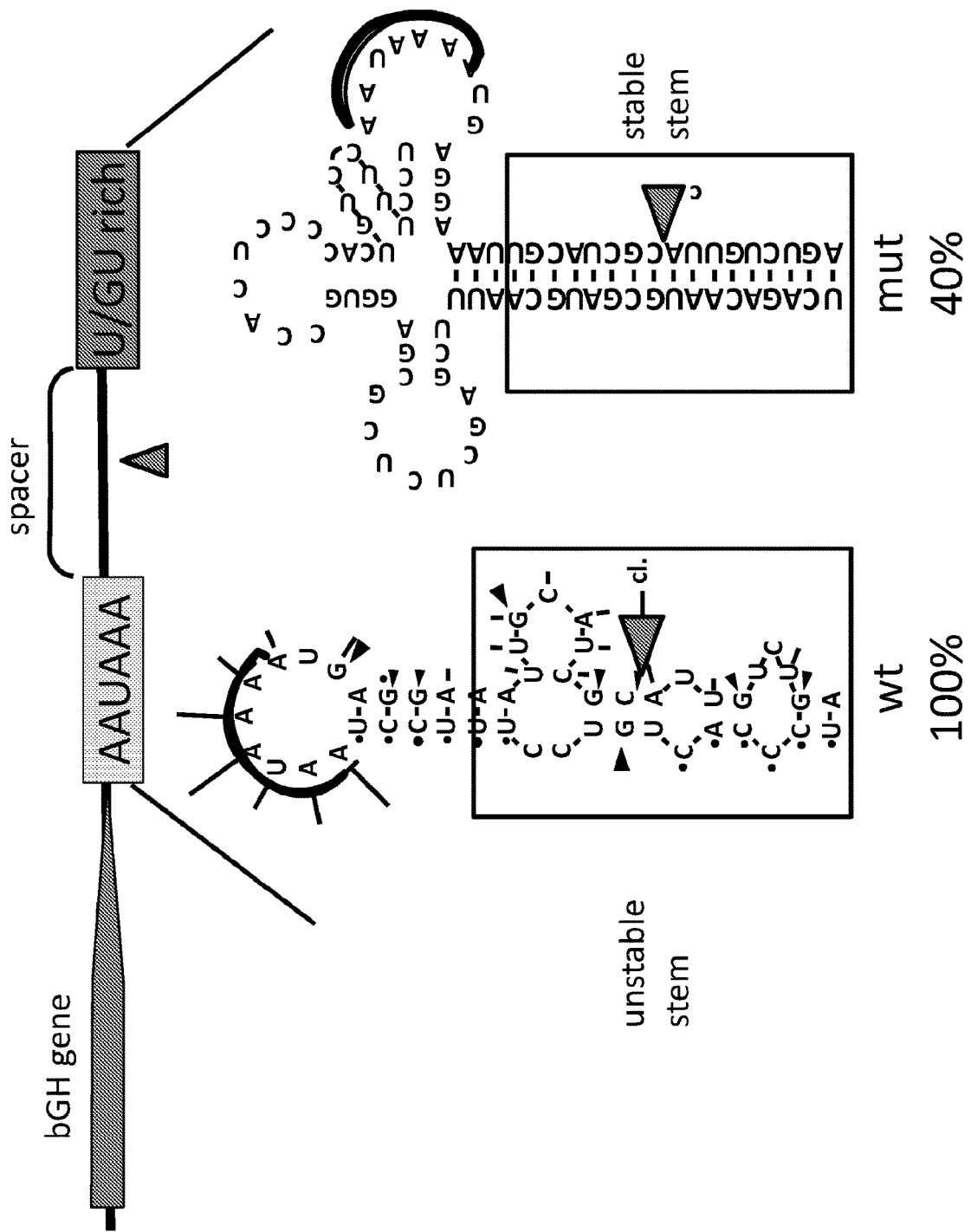
FIG. 3 shows that when the polyA cleavage site (triangle) of bovine growth hormone was hidden in a stable RNA stem, polyadenylation was greatly reduced as measured from 100% to 40%. (Adapted from Gimmi et al., 1989) [SEQ ID NO: 1; SEQ ID NO: 2]

Several reports have indicated that RNA secondary structures within the polyA site can profoundly influence polyadenylation efficiency in mammalian cells[6,33,34]. One study reported that by simply hiding the cleavage site within a stabilized RNA stem, the extent of cleavage/polyadenylation was greatly reduced[6] (FIG. 3). This suggests that cleavage can be efficiently controlled by local RNA structures. In one embodiment, detecting protein binding and controlling reporter gene expression is based on this simple yet effective modulation of RNA structure near the polyA cleavage site. As illustrated in FIG. 1, when a new polyA site is artificially created at 5'UTR, where they are never localized in normal transcriptional units, efficient cleavage of that polyA signal leads to destruction of the mRNA and loss of reporter gene expression due to the quick degradation of cleaved and uncapped 3' mRNA fragment. Unlike the normal polyA signal located posterior to the gene at 3'UTR, the artificially inserted polyA signal at 5'UTR functions as a 'suicide unit' in the mRNA. One can rescue the mRNA from suicide by inserting an aptamer at the cleavage site. Binding of a specific ligand to the aptamer blocks the cleavage, resulting in preservation of the intact mRNA, and therefore expression of reporter signal or transgene product. As described elsewhere herein, such a polyA cleavage-mediated sensor provides both specificity through dynamic sensing of the ligand via aptamer binding, and sensitivity due to ligand-dependent exponential amplification of reporter gene or transgene.

The Advantage of polyA Sensor as Genetically Encodable Imaging Tools

The polyA sensor sequence can be encoded as DNA in the format of plasmid or viral vector for delivery (for example), or genetically engineered into the genome of the cells (such as stem cells or cancer cells) or mice for transplanting and transgenic applications. One key advantage of genetically encoded sensor is the ability to limit their spatial distributions and control their temporal intervals in vivo. Unlike chemical dye probes that can unintentionally stain large area of untargeted tissues, the expression of RNA sensors can be effectively restricted to target cells or tissues by using tissue-specific promoters included in the DNA vectors. In specific embodiments, these additional safety features would significantly minimize the potential side effects resulted from the binding of sensor to its target ligand, as well as reduce background noise in vivo. Furthermore, unlike detection methods that lack signal amplification, a single encoded DNA copy in cells can generate hundreds of identical RNA sensors, which in turn can generate thousands more of reporter proteins, and through further enzymatic reactions by the reporter proteins, this can result in exponential amplification of the signal.

PolyA Sensor could Bridge a Critical Barrier for Monitoring Molecular Signatures In Vivo The polyA sensor provides a much-needed mechanism for monitoring a native protein by linking sensing, amplification, to signal detection/imaging in vivo. As mentioned above, because proteins contain abundant functional groups for chemical interactions, methods for creating aptamers for targeting proteins with high affinity are well-established[7-12].

For example, aptamers have been created to bind specifically to HIV tat protein[35,36], thrombin[37], vascular endothelial growth factor[38], DNA repair protein Ku[39], and tumor regulator osteopontin[40], to name a few. The specificity of aptamers even allows the recognition of different isoforms of the same protein, such as the P50 and P65 isoform of the transcriptional factor NF-kB[41,42], or the unphosphorylated and phosphorylated form of protein kinase ERK2[43]. These examples demonstrate the effectiveness of aptamers in recognizing disease-relevant proteins and their metabolic states.

The field of imaging reporter is also fast evolving. For example, GFP have revolutionized many areas of biology as reporters of gene expression, although their uses for in vivo imaging have been restricted to transparent tissues mainly due to the tissue penetrance limitation of optical imaging. Engineered infrared fluorescent proteins (IFP) with excitation/emission wavelengths capable of penetrating deep tissues and suitable for whole-body imaging has been developed[44]. Moreover, it has been demonstrated that thymidine kinase coupled with radioactive substrate [$^{18}$F]FHBG can be used for in vivo PET imaging in clinical settings[45-47]. More recently, new magnetic resonance imaging (MRI) method was developed to monitor the expression of GFP in vivo, providing a new use of GFP for noninvasive imaging via magnetic resonance[48].

Figure 4:
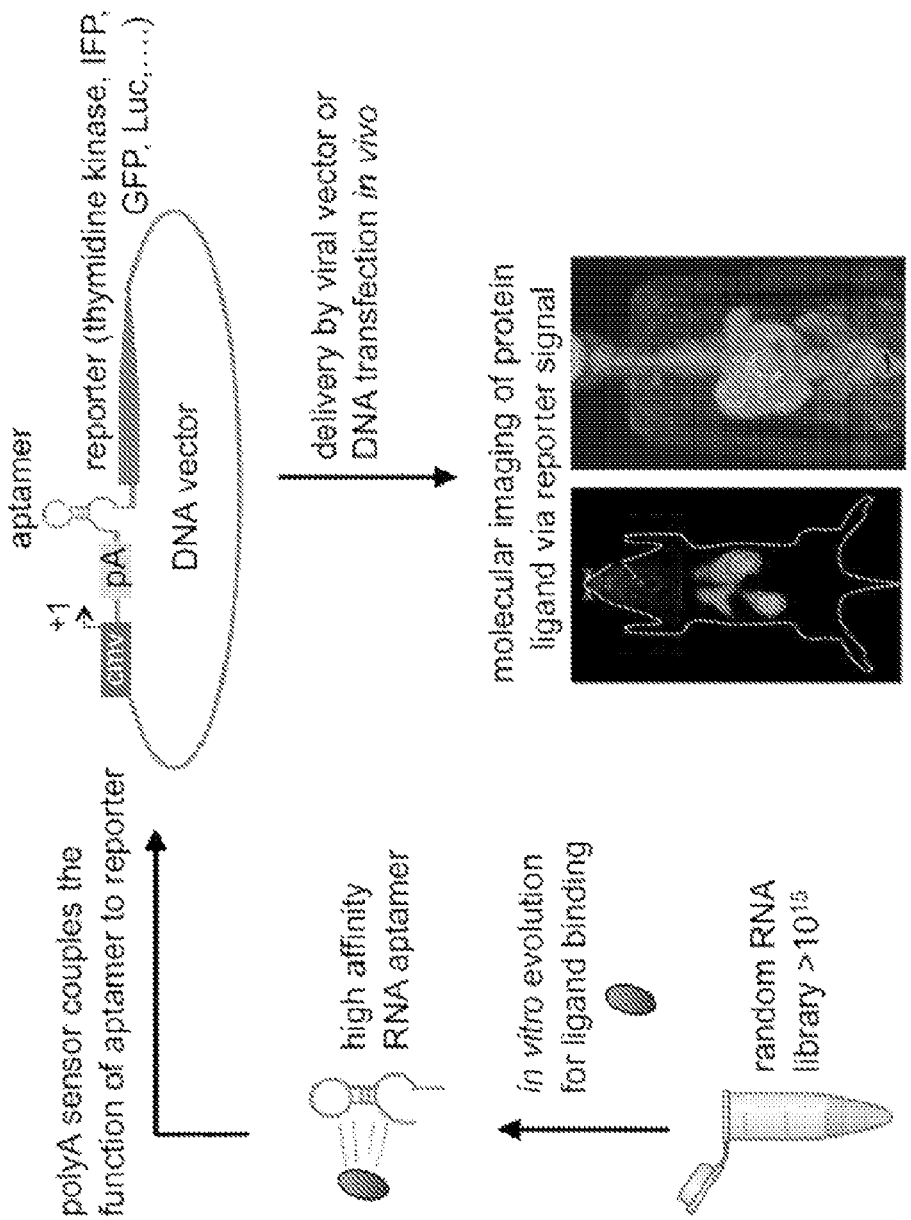
FIG. 4 illustrates that a polyA sensor system enables the utilization of existing aptamer technology and imaging reporters to form a flexible molecular imaging platform. pA: polyA signal. IFP: infrared-fluorescent proteins. Luc: luciferase.
Figure 5B:
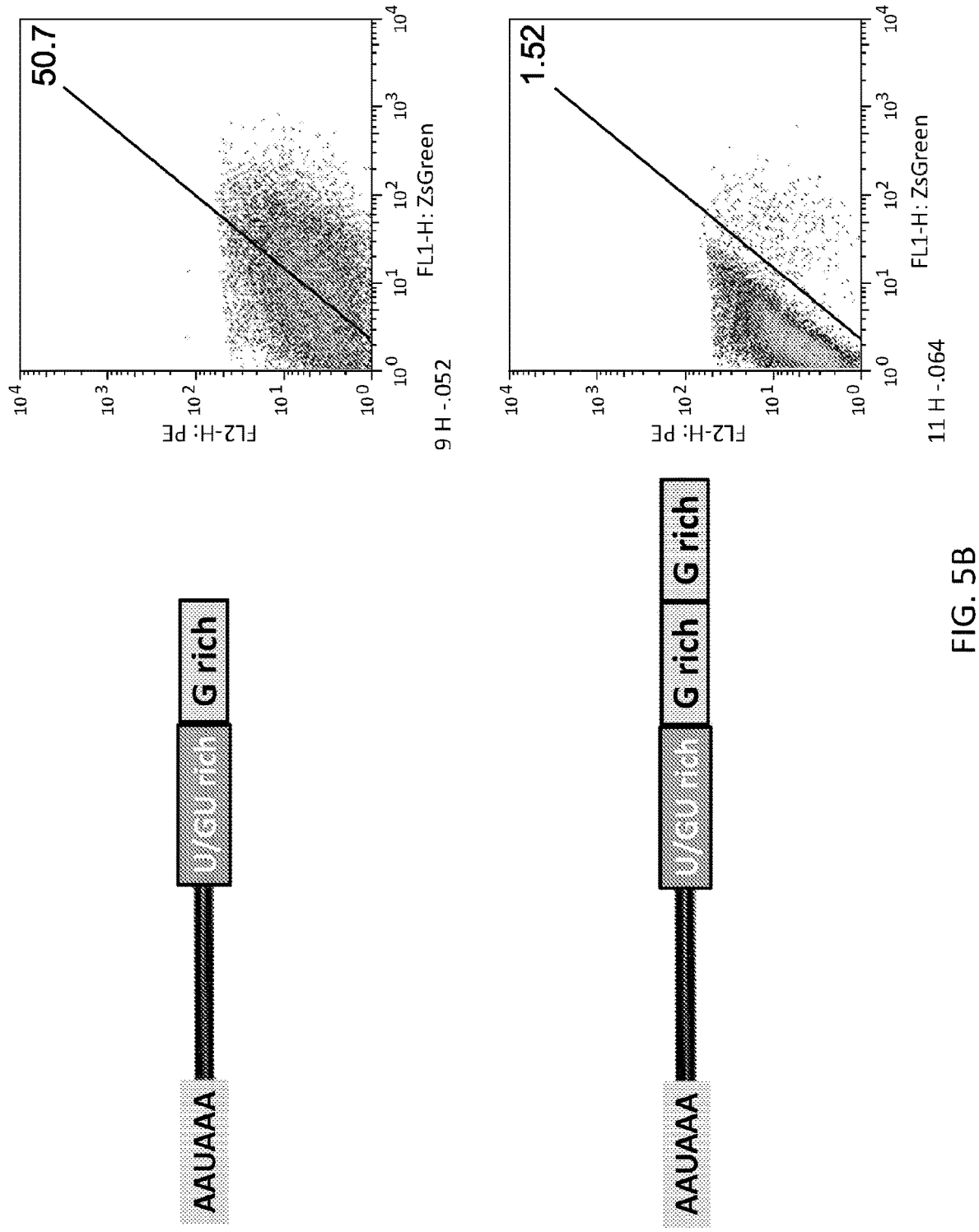
Figure 5C:
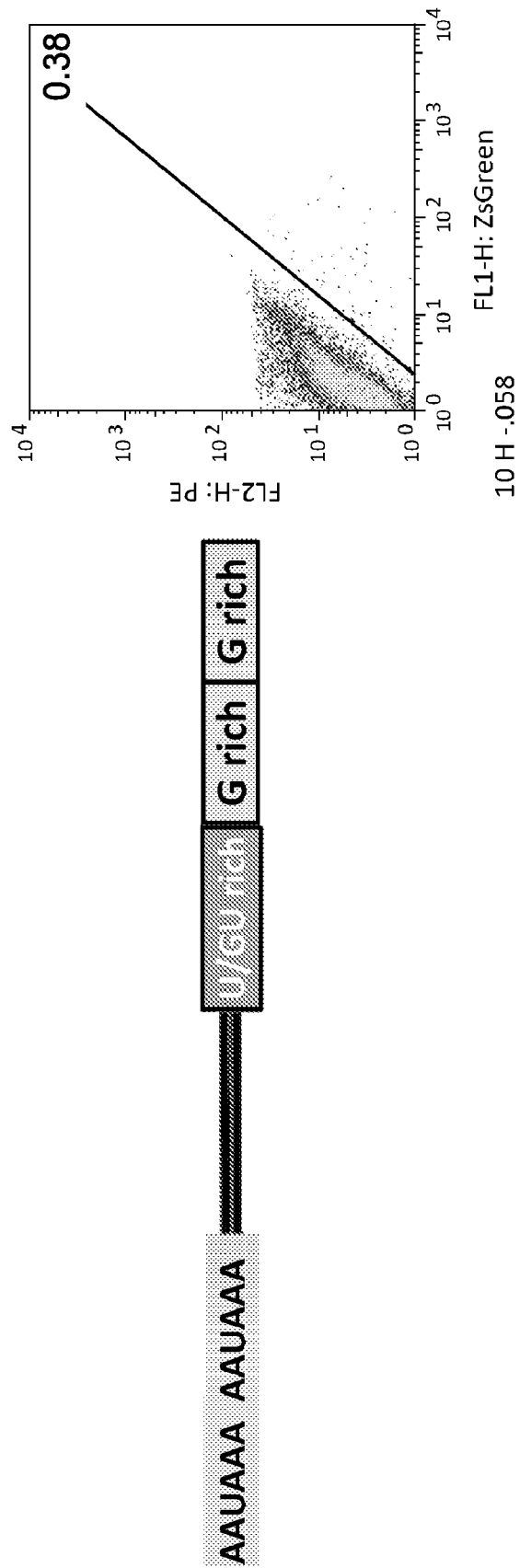

Aptamer-based sensing and reporter-based detection/imaging thus are powerful in their intended functions yet in combination are even more powerful, such as in detecting molecular signatures in vivo. What is missing is a powerful biological amplifier capable of linking these two functionalities, and translates 'aptamer sensing' to 'reporter expression' that can be detected by current imaging modality or other detection methods. A generalized schematic of embodiments that accomplish this is illustrated in FIG. 4. To monitor a specific protein ligand, a high affinity aptamer is first created through in vitro evolution. The polyA switch, which functions as a biological amplifier, links the aptamer to an imaging reporter to form a sensing device. Such a sensing device can be encoded in a DNA vector and delivered to target cells/tissue using appropriate viral or non-viral transfer methods. In the presence of the cellular ligand, aptamer binding generates strong signal through ligand-dependent exponential amplification of reporter gene. Importantly, the flexibility of aptamers allows the possibility of detecting a broad range of native proteins, and the flexibility of reporter choices allows the visualization via different detection modality. The proposed polyA sensor thus enables the utilization of existing technologies to provide a flexible, non-invasive in vivo molecular detection strategy that is dependent upon the presence and concentration of the native molecular signature.

In the last decade, the explosion of gene expression data obtained from high-throughput sequencing and DNA microarray have provided hundreds of proteins and their mutant isoforms that may be used in the future as biomarkers of diseases. Probing molecular signatures in vivo not only aids in diagnosis, but also provides measurements of cell proliferation, alternations in metabolism, and therapeutic response based on the elevation of specific protein biomarkers (for example). In certain embodiments, the polyA sensor addresses this class of measurements that has been difficult to address previously, and provides a significantly broader application in molecular detection than is currently possible.

In particular embodiments, the methods and compositions of the present disclosure provide the ability to control the expression of a transgene with precision but avoid reliance on currently used gene expression reagents such as hybrid transcriptional transactivators and specialized promoters. In specific embodiments, the present methods avoid having to utilize more than one expression construct, avoid potential toxicities because of expression of a hybrid transactivator (including induction of host immune responses directed towards the transactivators that are foreign proteins, avoid difficulties with requirements for a specialized promotor, and avoid having to use the limited number of small inducer molecules available for experimental and therapeutic application (because of the limited number of available systems).

Instead, the present polyA-based system of the disclosure does not require the expression of any protein transactivator products and is not dependent upon the use of any specialized promoter elements. Thus, it provides a 'portable' regulation system that could be 'embedded' into any endogenous gene or engineered vector transcription unit. As such, the system requires only one transcriptional unit (one expression construct), and its promoter is flexible so that it can be used to regulate transgenes in a tissue-specific (spatial) and temporal manner. The universal nature of polyadenylation existing in all mammalian cells allows the system to be widely applicable.

Example 2

Initial Exemplary Studies

The initial studies described in this Example demonstrate the development of polyA sensor systems. Specifically, through the analysis of a number of polyA signals, there is developed a polyA cleavage-mediated sensor that is efficiently cleaved in human cells when embedded in the 5'UTR of a standard expression vector. Importantly, described herein is an aptamer sequence designed to bind a specific ligand as part of the sensor without affecting the polyA cleavage efficiency. Lastly, by co-expressing the ligand protein in live human cells, the sensor readily detected its ligand, leading to the increase of reporter signal more than a hundred fold. The results demonstrate that detection of specific label-free intracellular proteins are readily achieved in live human cells, and the extent of induction as measured by signal-to-noise ratio represents a range that would be useful for many applications.

Identification of polyA Motifs that Function Efficiently at 5' UTR in Human Cells The general strategy for detecting and imaging proteins via modulation of polyA cleavage is critically dependent upon the highly efficient cleavage of the polyA signal at the 5' UTR (FIG. 1). A first step was to test candidate polyA signals and associated upstream and downstream motifs that enable efficient polyA cleavage in cells. For testing polyA cleavage efficiency, a transient transfection assay involving a mammalian expression vector[49] was used with a GFP or luciferase reporter (merely as examples). Candidate polyA signal sequences were cloned at the 5'UTR of the reporter gene or transgene within the expression vector. Control vectors with inactive polyA signal (AAUAAA to CACACA mutations)[50] were also made to provide upper limit of the expression levels to which the efficiency of cleavage by active polyA signals are compared after transfection of human HEK293T cells.

A number of different polyA signals and associated upstream and downstream motifs were utilized for initial analysis. While the majority of these polyA signals tested appeared to function to some extent in human cells, as reflected by their ability to suppress reporter gene expression to different degrees at 5'UTR, one synthetic polyA published by Proudfoot lab[51] was particularly useful under the tested conditions, in specific embodiments. Based on its apparent higher level of cleavage activity, this polyA was utilized for further study purposes. To improve the efficiency of cleavage activity, a series of modifications of the polyA sequence were made and evaluated. Most notably, positioning of a G-rich sequence[52] downstream of the polyA site significantly enhances cleavage, possibly through the transient pausing of transcription caused by the G-rich sequence[53,54]. Increasing the copy number of G-rich region from one to two further enhanced the cleavage. Placing two copies of 'AAUAAA' in tandem also appreciably increased the cleavage (see FIGS. 5A-5C). The resulting polyA configuration containing the combination of '2 AAUAAA+spacer+G/U rich region+2 G-rich region' was used as the general template in subsequent studies.

In particular embodiments changing the length of the spacer between 'AAUAAA' and G/U-rich region from 14 to 25 bases, or replacing the spacer by an aptamer, had little effect on polyA cleavage efficiency, indicating that the length of spacer is flexible within the range tested and could accommodate aptamer sequence of different lengths. Thus, polyA signal can be cleaved efficiently in human cells in the 5'UTR, and some sequence alterations within the spacer are well tolerated.

Figure 6:
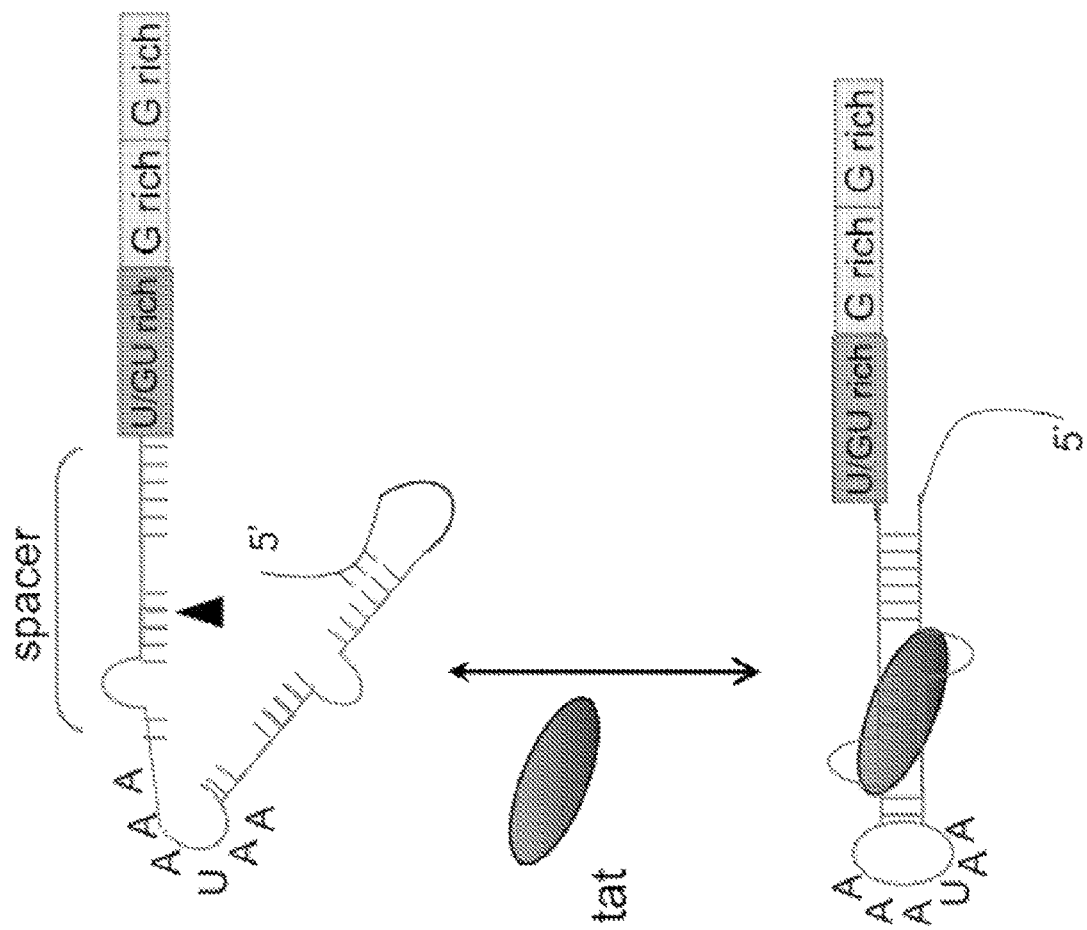
FIG. 6 illustrates a 'clamping' approach. Ligand binding effectively locks the aptamer in a stable double-stranded stem structure, and physically blocks the cleavage site indicated by the triangle.

Efforts of Engineering Aptamer into polyA-Based Sensor for the Detection of Intracellular Ligand in Human Cells Having demonstrated the ability of the polyA signal to cleave at 5' UTR in cells, in specific embodiments a ligand-binding aptamer is engineered as part of the polyA sensor. This enables the sensor to bind specific protein ligand, resulting in the inhibition of cleavage and therefore the induced reporter expression. As a specific embodiment, an aptamer that binds HIV tat protein was utilized. This binding is a simple one-to-one interaction involving no other cofactor, and with a dissociation constant Kd of 0.1 nM[35,36] comparable to the affinity achieved by antibodies. To create an efficient sensor, a 'rational design' approach was utilized using an engineering principle called 'clamping' (FIG. 6). Here, the aptamer is strategically positioned to flank the AAUAAA signal and replaces most of the spacer region. The resulting RNA is designed to switch between two primary conformations: one in which the ligand binds the sensor, and therefore 'clamps' the spacer region; the other in which the sensor is unbound and the spacer exists primarily as a single strand. In the first conformation, ligand binding effectively locks the spacer in a stable double-stranded stem structure, which significantly reduces polyA-mediated cleavage[6,33,34] Furthermore, ligand physically docks on the cleavage site, essentially blocking the access to polyA associated cellular proteins required to initiate the cleavage.

Based on this principle of 'clamping', more than 40 different constructs were designed in which the stability and length of the spacer, and the position of aptamer within the spacer, were adjusted to maximize the ratio of reporter activity between the 'bound' (ligand present, no cleavage) and 'unbound' (ligand absent, cleavage) states. Testing this series of design in human cells revealed that this strategy of 'clamping' resulted in highly sensitive sensors with superb switching behavior. One design showed very low leakage expression in the unbound state and a strong induction of reporter signal in the presence of ligand in cells (see below). The above engineering embodiments create an efficient polyA-based sensor system, as they establish an example of how engineered RNAs can be efficiently harnessed to build a functional sensor/amplifier for the purpose of detecting an intracellular ligand in live cells.

Figure 7A:
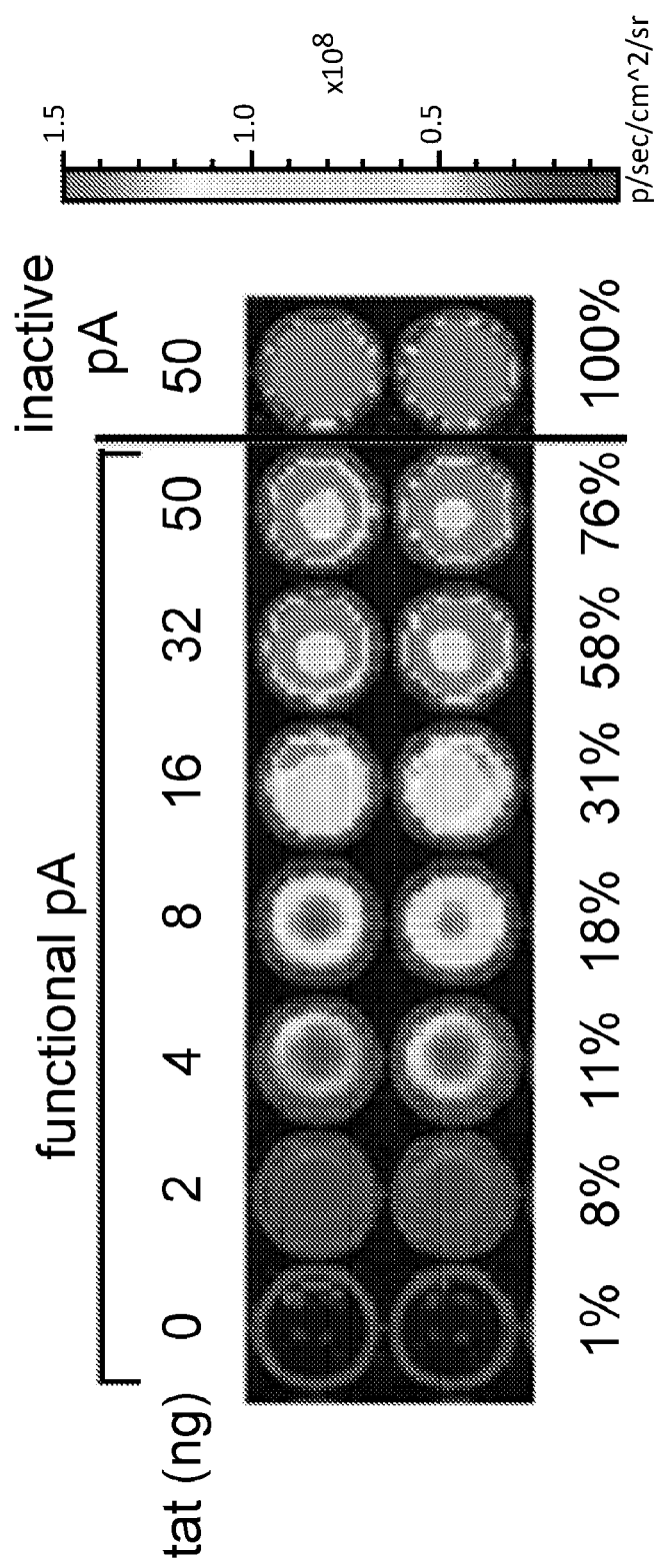
FIGS. 7A-7C show a dose-dependent response of the polyA sensor designed for detecting the viral tat protein.
Figure 7B:
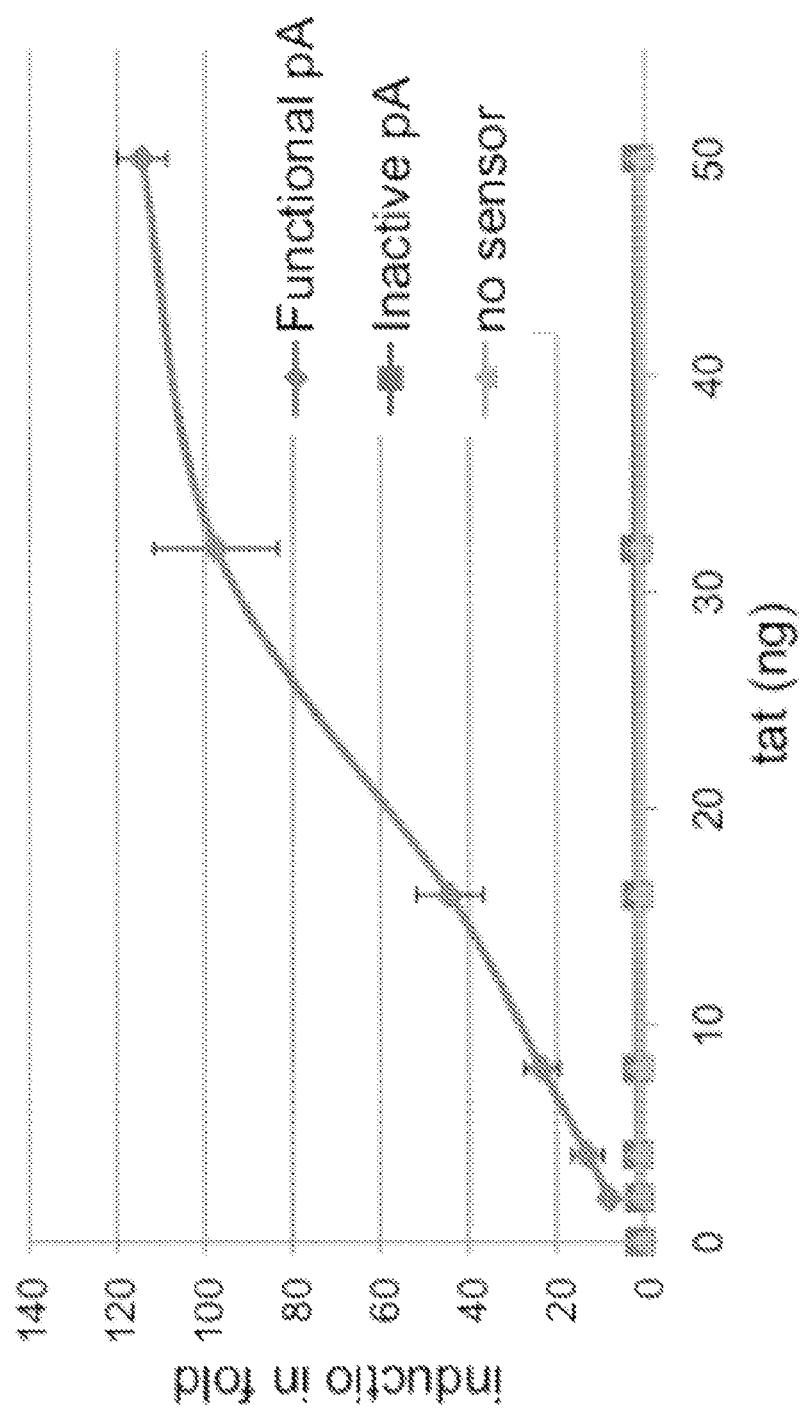

Demonstration of the Function of polyA Sensor in Cells in Response to a Cellular Ligand With the engineered polyA sensor, it was shown that transfection of a ligand expressing vector, together with the sensor vector into 293T cells, led to a dramatic increase in luciferase reporter signal (FIG. 7). In the absence of ligand, the reporter signal from such a sensor exhibited very low leakage expression (FIG. 7a, lower than 1% of the expression level of inactive polyA control). This leakage expression provides a basal level for the calculation of induction in 'fold' as a ratio of reporter signal in the presence vs. absence of ligand. Importantly, the response of the sensor was 'tunable' and reflected the amount of ligand in cells in a dose-dependent manner. Furthermore, the induction reached up to 120-folds (FIG. 7b), or approximately 76% of the theoretical inducible range using the expression level of inactive polyA sensor as the reference (FIG. 7A). This extent of induction is about two orders of magnitude higher than have been previously achieved in live human cells, and is sufficient to form the basis for a sensor platform. In contrast, no significant induction was observed in cells transfected with inactive polyA or parental vector without the embedded polyA sensor (FIG. 7B), indicating that the mechanism responsible for induction is indeed mediated through polyA signal.

Figure 7C:
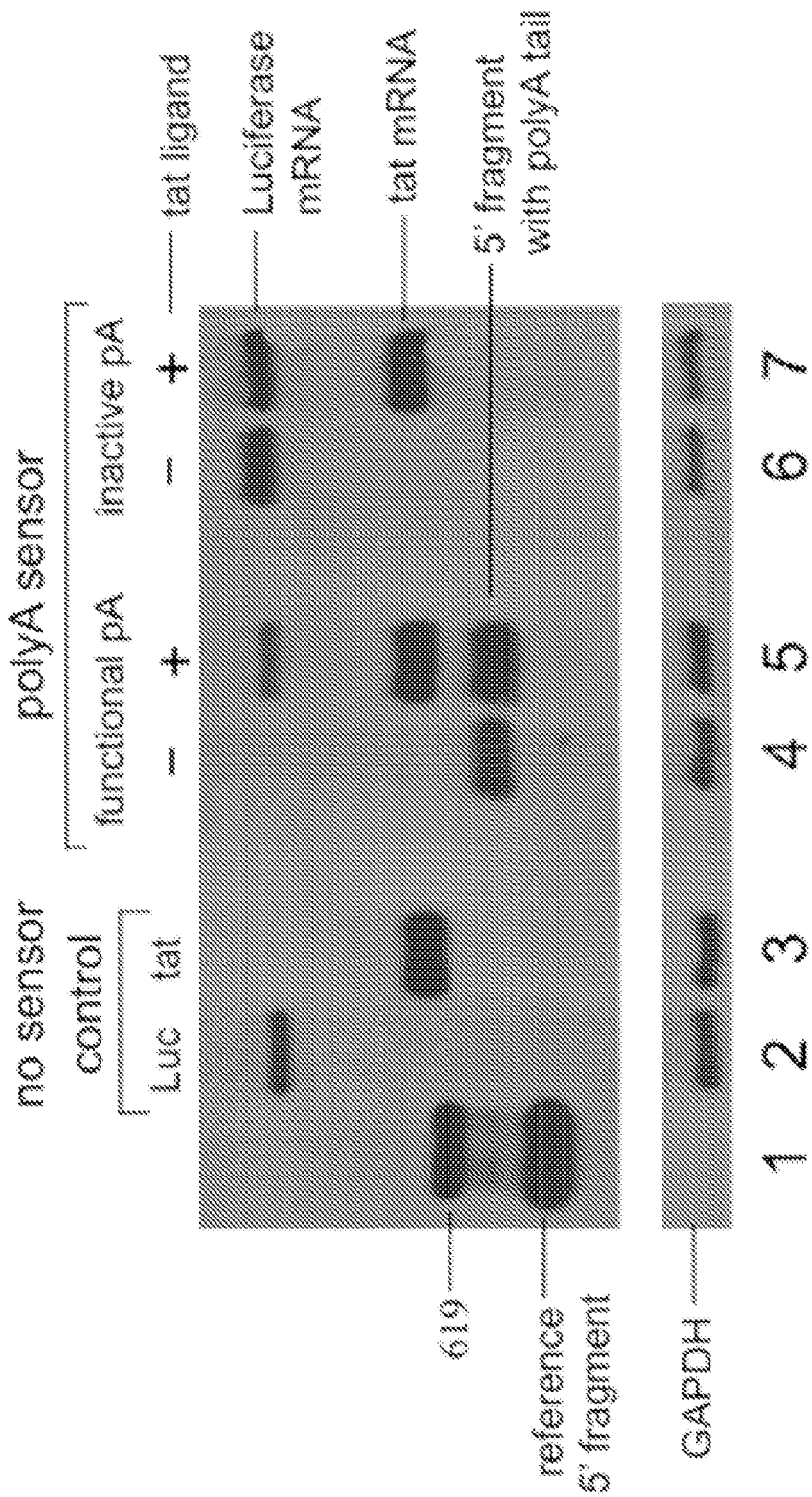

To establish that at the mRNA level, the response is also consistent with the proposed mechanism, a northern analysis was performed of luciferase mRNA in response to ligand binding. As shown in FIG. 7C, in the absence of ligand (lane 4), no luciferase mRNA was observed, suggesting that cleaved mRNAs were rapidly degraded. In contrast, the presence of ligand significantly increased the amount of luciferase mRNA (lane 5). Furthermore, a band slightly higher than the reference cleaved 5' fragment was observed in cells carrying active sensor (lane 4, 5 compared to lane 1), suggesting that the cleaved 5' fragment was polyadenylated. RT-PCR and then cDNA sequencing were used to confirm that a polyA tail was indeed added at the expected cleavage site at the end of the 5' cleaved fragment. Together, the results are in close agreement with the mechanism that ligand binding blocks polyA cleavage and preserved the intact mRNA for induction.

Previous Demonstration of the Utility of RNA-Based Sensor In Vivo

In vivo studies of another RNA sensor based on the self-cleavage of hammerhead ribozyme that functions efficiently in vivo have been performed[4,55]. This ribozyme was used to construct an RNA sensor in which the spontaneous self-cleavage of ribozyme embedded at the 5' UTR leads to destruction of the mRNA and therefore a loss of reporter gene expression. The presence of toyocamycin, a small molecule inhibitor of ribozyme, blocks ribozyme self-cleavage and results in preservation of the intact mRNA, and therefore induced reporter expression. To demonstrate the function of ribozyme-based sensor in vivo, recombinant adeno-associated virus (AAV) was generated encoding the ribozyme-based RNA sensor, and was delivered into the eyes of nude mice as the host tissue. As a control, AAV encoding the inactive ribozyme was delivered the virus to infect hamstring muscle. The molecule toyocamycin was then administrated through a drug pellet embedded under the dorsal skin of the mice. The mice were imaged using the IVIS200 imager to provide a quantitative measure of luciferase expression based on photon detection[56,57]. Representative images of mice, taken before and after toyocamycin treatment showed that the sensor was able to detect the presence of toyocamycin in retina and resulted in induced luciferase reporter expressions up to 180-fold[4]. In contrast, no increase in luciferase expression was observed in muscle carrying the inactive ribozyme. These results demonstrated that RNA sensors encoded in viral vectors and delivered to a target tissue were able to function efficiently in vivo, and the intensity of induced reporter signal was readily detectable by whole-body imaging. While these studies did not make use of aptamer or polyA cleavage as the mechanism, the general experimental setup for in vivo imaging can be modified to demonstrate the utility of polyA sensor in live mice.

The optimized sensor developed for HIV tat is an example that could be used in detecting and imaging HIV infected blood cells or tissues in vivo. Alternatively, this or another sensor can be engineered into a cell line to create a stable 'sensor cell' to titer the number of infectious HIV particles in patient's blood. Recent explosion of biomarker discovery has provided hundreds of additional proteins that may be used similarly as molecular signature of diseases. Probing these molecular signatures in vivo aids not only diagnosis, but also monitoring of a therapeutic response based on the elevation of specific proteins. The technology is useful to detect/image these and other specific cellular proteins, and addresses a class of measurements that has been difficult to achieve previously. The spectrum of molecular signatures that can be detected by polyA sensors could include not just proteins but other biomolecules, and FDA-approved small molecules. Together with future generations of clinically applicable reporters that can be imaged by infrared[44], PET[45-47] or MRI[48], the polyA sensor has broad applications in molecular imaging.

Figure 19:
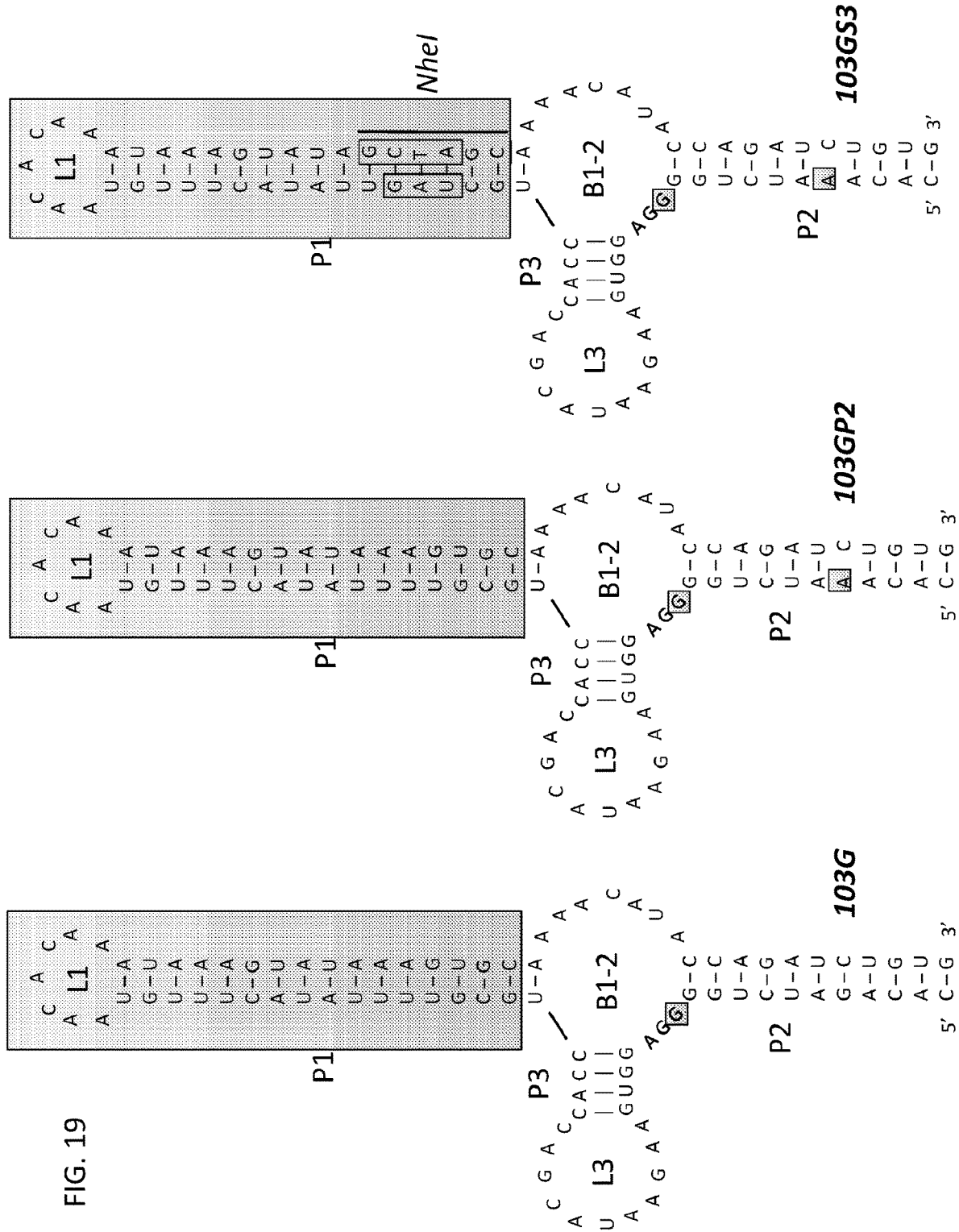
FIG. 19 shows examples of modifications of exemplary aptamers. Aptamer 103G was modified at the noted positions to produce 103GP2 and 103GS3 aptamers [SEQ ID NO: 16; SEQ ID NO: 17; SEQ ID NO: 18]
Figure 22:
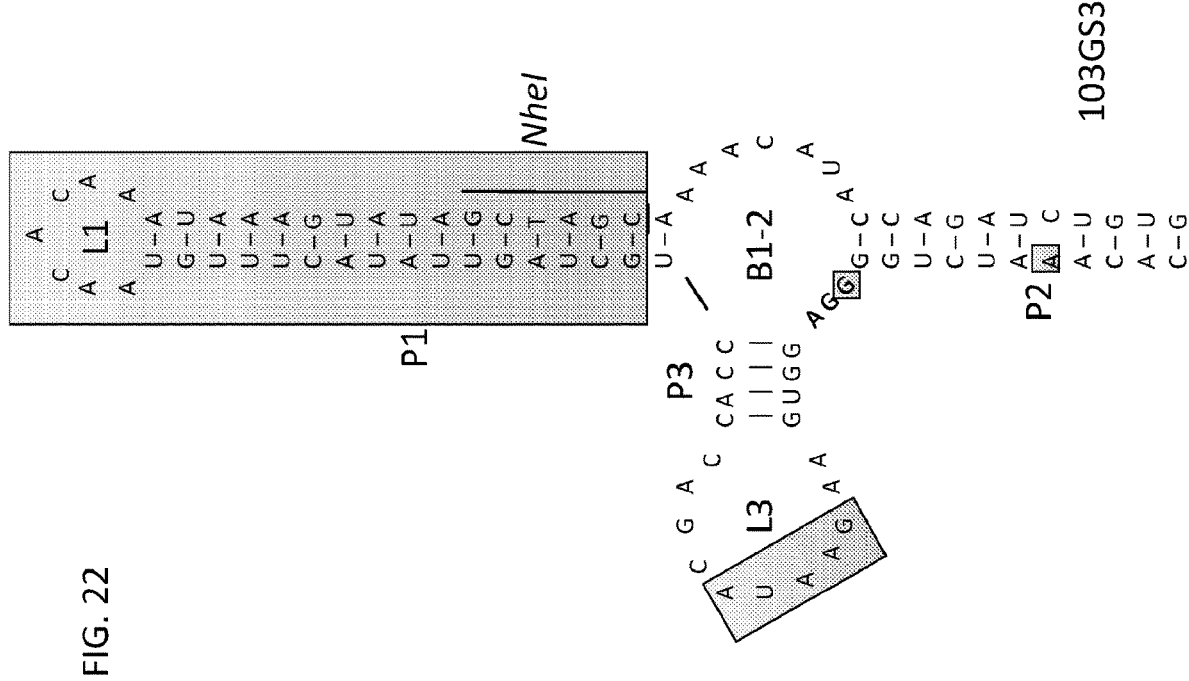
FIG. 22 demonstrates variation in modification of the L3 region of 103GP3 and the corresponding impact on fold induction of gene expression [SEQ ID NO: 20].
Figure 23:
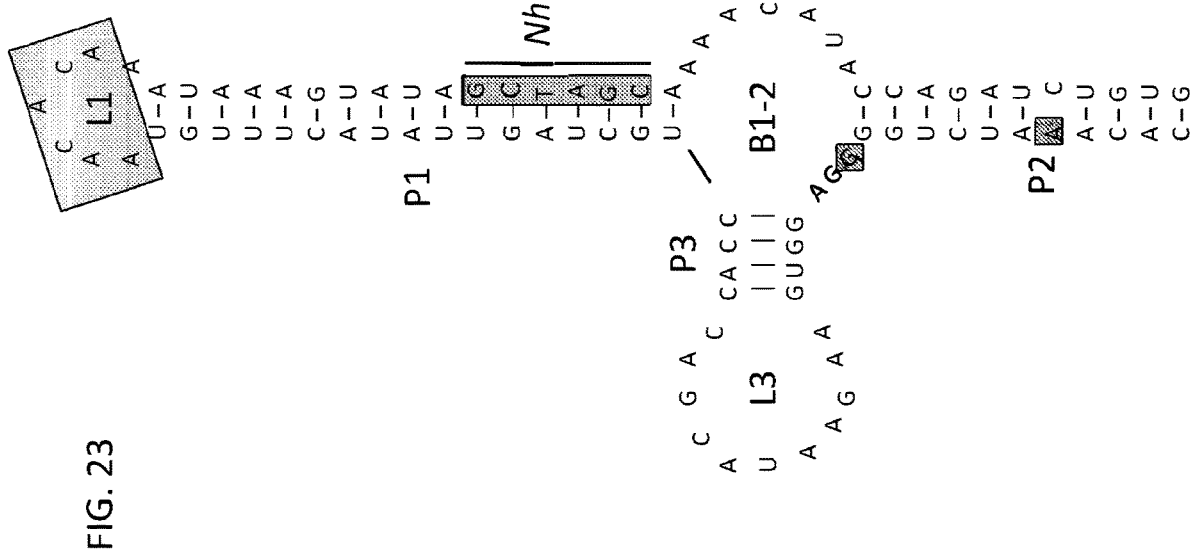
FIG. 23 demonstrates variation in modification of the L1 region of 103GP3 and the corresponding impact on induction of gene expression [SEQ ID NO: 21; SEQ ID NO: 22; SEQ ID NO: 23; SEQ ID NO: 24; SEQ ID NO: 25].
Figure 24:
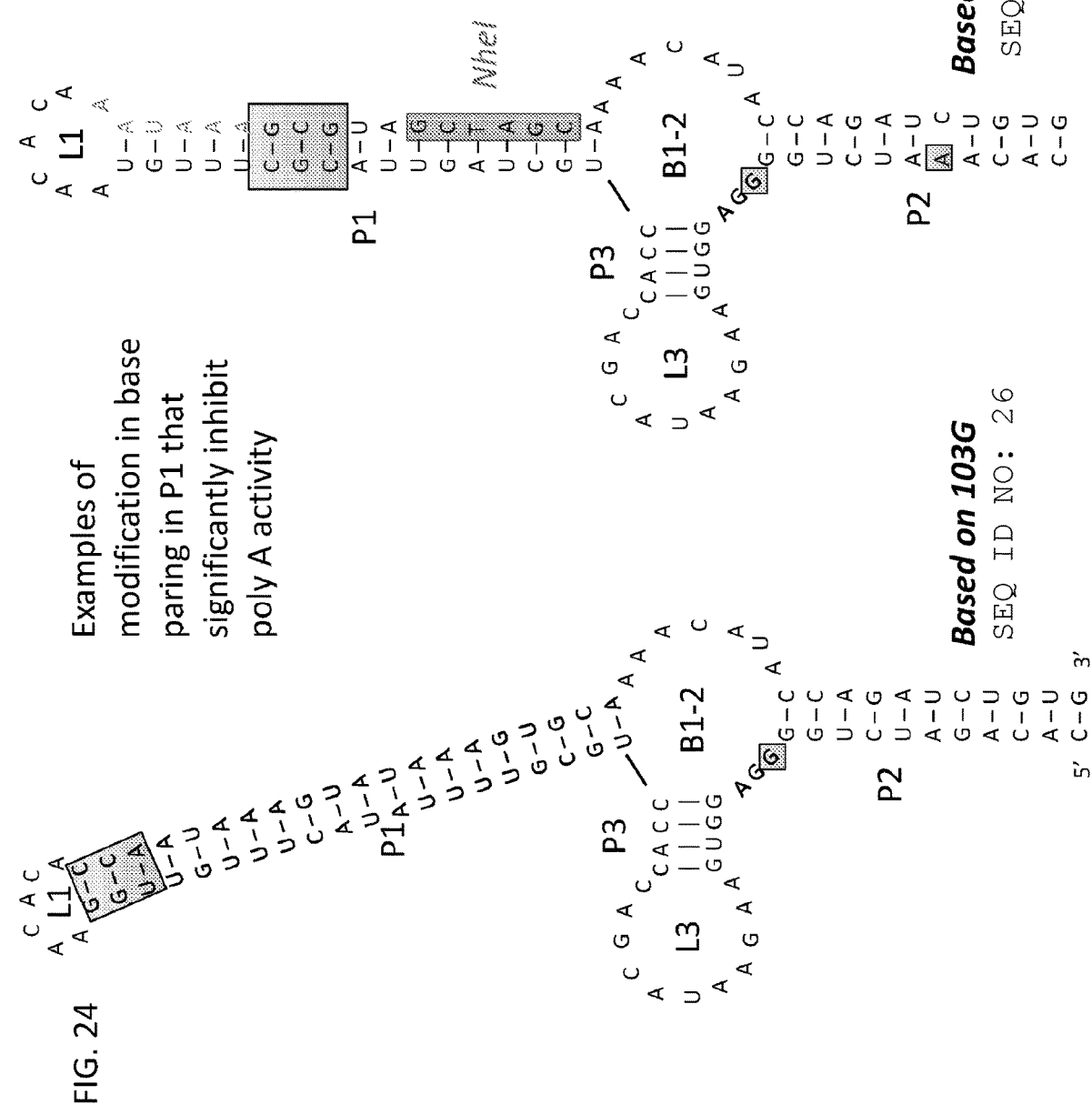
FIG. 24 illustrates examples of modification in base pairing that stabilize P1 and thus lead to significant inhibition of polyA activity. Modified regions are in box [SEQ ID NO: 26; SEQ ID NO: 27].

Demonstration of the Utility of polyA Switch for Gene Regulation Using a FDA-Approved Drug As shown in FIG. 19, the polyA signal can be efficiently engineered within an aptamer that recognizes tetracycline as its ligand. Tetracycline is a FDA-approved drug with long history of clinical uses and safety record. In the absence of tetracycline, the transgene or reporter gene exhibited very low leakage expression (FIG. 20), lower than 0.2% of the expression level of the inactive polyA control. Upon tetracycline administration, the expression of the transgene or reporter gene was turned on up to ~30 folds. The induction by tetracycline is dose-dependent (FIG. 17), allowing precise control of the expression of a transgene by a safe FDA-approved drug.

Example 3

PolyA Aptamer Comprising Multiple Aptamers

In some embodiments of the disclosure, the polyA aptamer molecule comprises 2, 3, 4, 5, or more aptamers, and in particular cases the aptamers are linked linearly along a 5' to 3' direction of a single molecule. There may or may not be non-aptamer sequences between the different aptamers. In specific embodiments, when there are multiple aptamers, one aptamer in relation to another aptamer may have the opposite orientation of the aptamer (that is, the 5' to 3' direction of one aptamer is reversed in a 3' to 5' direction in a second aptamer) (FIGS. 18A (middle image) and 25), although in alternative cases the second aptamer is in the same orientation (FIG. 18A (far right image). In particular cases of a construct comprising one or more aptamers, a G-rich region resides at or near the 3'-most end of the molecule, and an example of a G-rich region is the MAZ region (FIG. 25). Thus, FIG. 25 illustrates a new construct GP2 in which the polyA signal is flanked by 2 aptamers in different orientation. The design is based on one of the configurations described in FIG. 18. When treated with 5 μg/mL Tc, GP2 showed an improved induction of 12.6-fold as compared to the 10-fold induction of 103GP2 described in FIG. 21. Variation in modification of the P2b region of GP2 and the corresponding impact on induction of gene expression are also shown.

Figure 26:
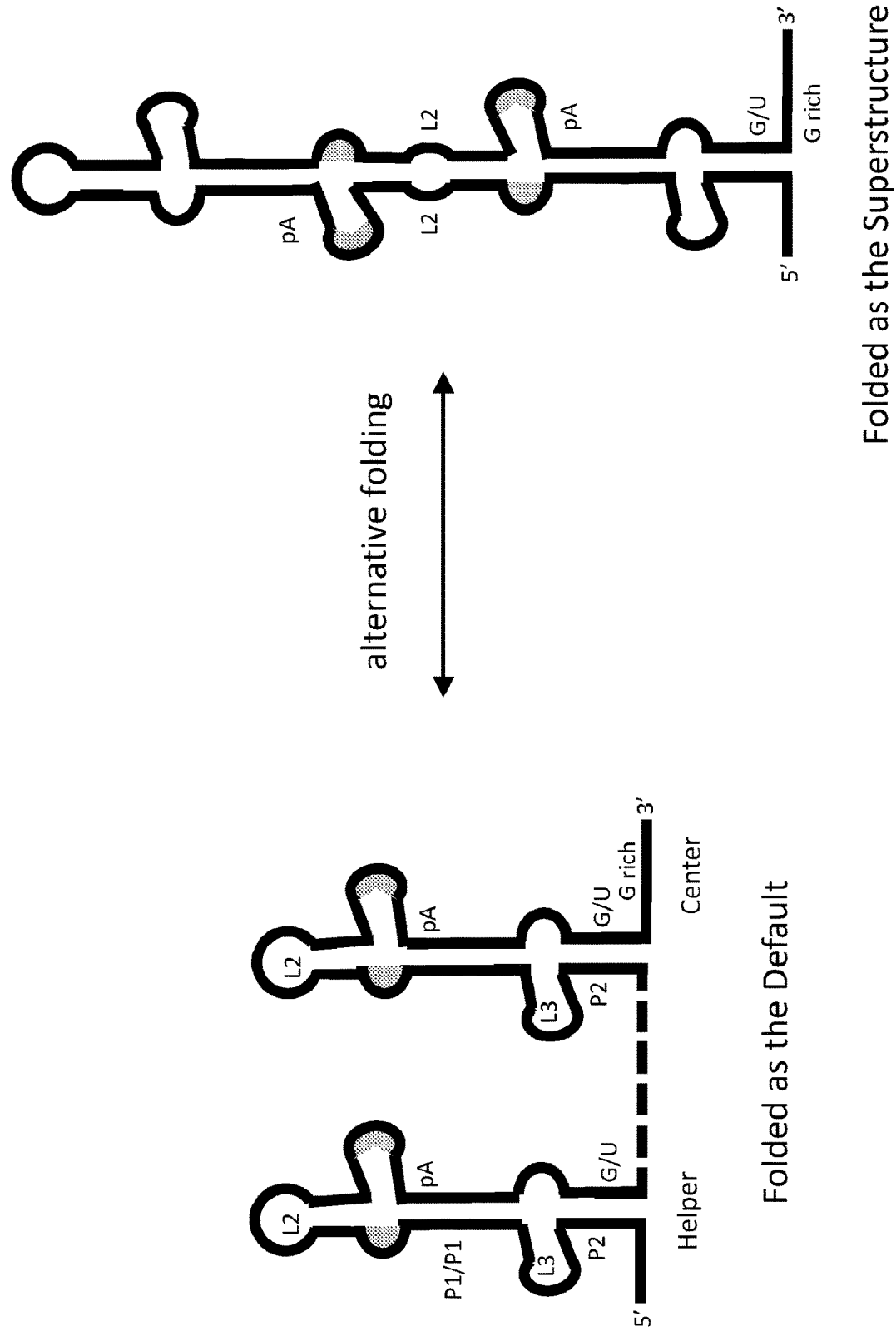
FIG. 26 illustrates an example of a polyA sensor construct, GP2SLGP2, having a configuration with two GP2 aptamers connected back to back that allows alternative folding. The 5' GP2 aptamer is called the Helper, the 3' GP2 aptamer is called the Center. Both contains an active polyA signal but only the Center aptamer contains the G-rich region.

In some embodiments, a polyA aptamer molecule comprises two aptamers linked linearly, although the molecule may have a three-dimensional shape of a variety of shapes. FIG. 26 illustrates a new construct GP2SLGP2 in which two GP2 aptamers are connected back to back. The 5' GP2 aptamer is called the Helper, the 3' GP2 aptamer is called the Center. Both contain an active polyA signal but only the Center aptamer contains the G-rich region. This configuration is designed to allow alternative folding between two different structures: the Default structure and the Superstructure C. When treated with 5 μg/mL Tc, GP2SLGP2 showed a dramatically improved induction of 70-fold as compared to the 12.6-fold induction of GP2. In cases wherein there are multiple aptamers that develop a three-dimensional structure, the sequences of two loops may align (see right image of FIG. 26). In cases wherein multiple aptamers are present on a molecule, only one G-rich region is present on the molecule, in specific embodiments, and the G-rich region may be present on the second aptamer (in a 5' to 3' direction) or is present on the 3'-most aptamer of the molecule, in certain cases.

FIG. 27 shows a particular superstructure molecule akin to the right image of FIG. 26 and comprising the GP2 sequence of the loop P2b listed in FIG. 25. Variation in the length and sequence of the stem/loop-II region (the boxed region) of the Helper GP2 and the Center GP2, and the corresponding impact on induction of gene expression are shown. Sequence variation between different constructs are shown in red. When folded as the Superstructure C structure, the central stem of GP2SLGP2 has an equivalent length of 18 bp, while C12 has an equivalent length of 20 bp. The construct C12 reached an induction of 94-fold at 5 μg/mL Tc, while the construct D11A reached an induction of 84-fold at 5 μg/mL Tc. Both significantly surpassed the 70-fold induction of GP2SLGP2 at 5 μg/mL Tc. In specific embodiments, the sequence of the loop 2 (boxed region in FIG. 27) causes the region to reside as a double stranded region instead of a loop. In a superstructure molecule as shown in FIG. 26 (right image) and FIG. 27, the length of the region between the polyA (pA) "dogbones" and including the boxed L2 region is between 10-25 nucleotides, such as 18-20 nucleotides, for example.

Figure 29:
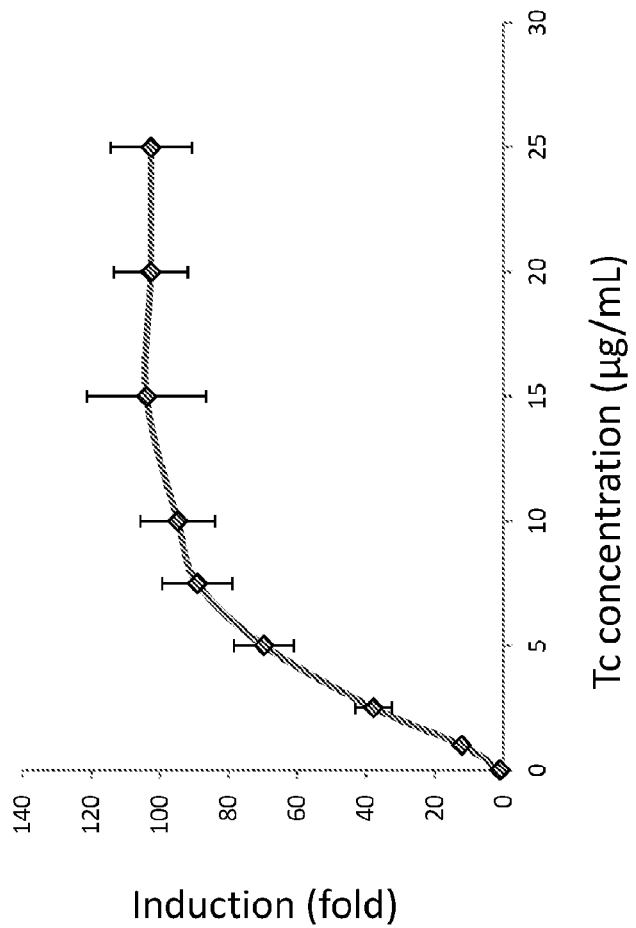
FIG. 29 demonstrates the dose-dependent regulation of GP2SLGP2. Each data point corresponds to a relative fold induction determined as the ratio of luciferase activity with and without tc. Average fold induction with standard deviation are shown. The induction reached 104-fold at 15 μg/mL Tc.
Figure 30:
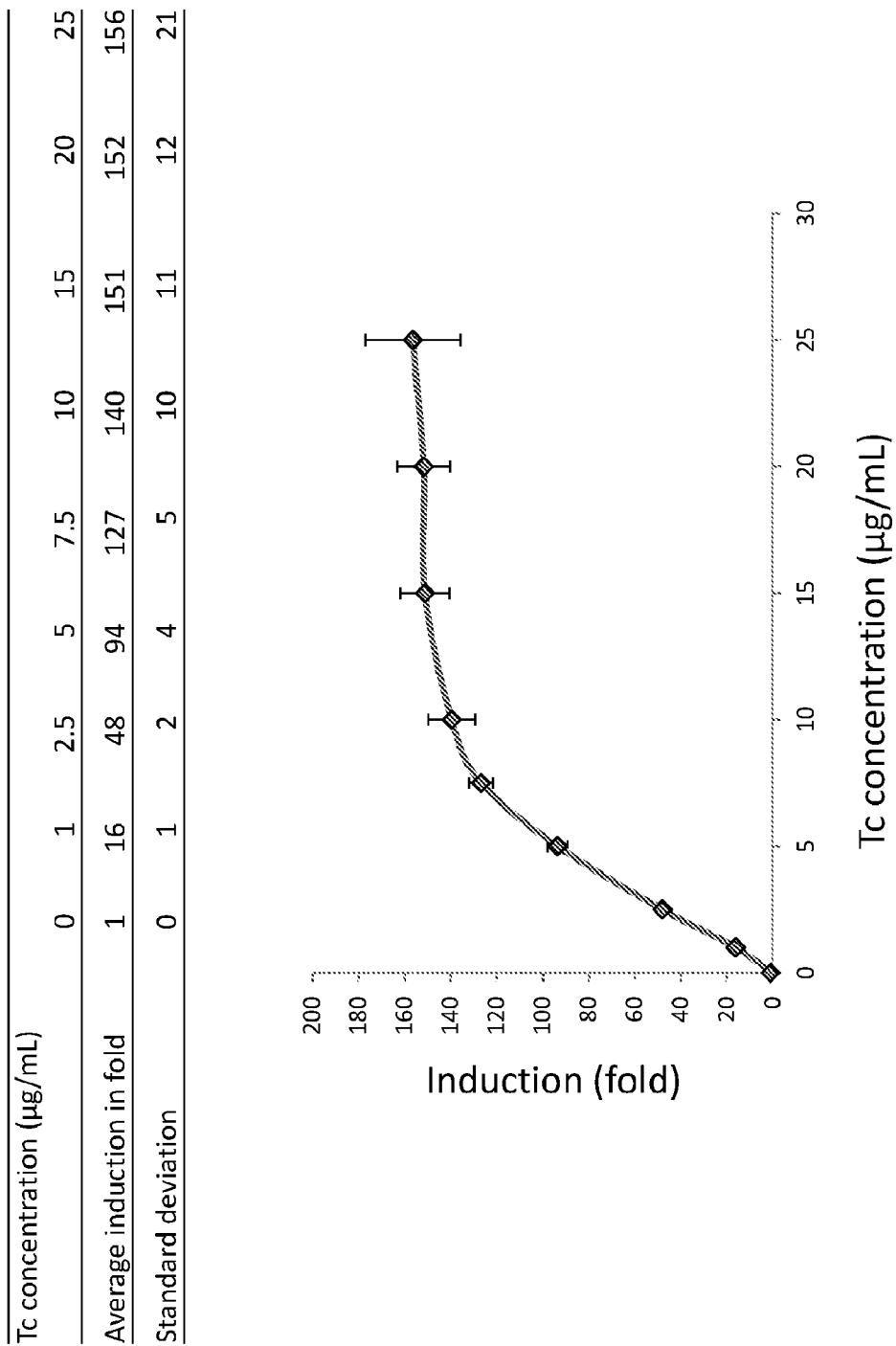
FIG. 30 demonstrates the dose-dependent regulation of C12. Each data point corresponds to a relative fold induction determined as the ratio of luciferase activity with and without Tc. Average fold induction with standard deviation are shown. The induction reached 151-fold at 15 μg/mL Tc.
Figure 31:
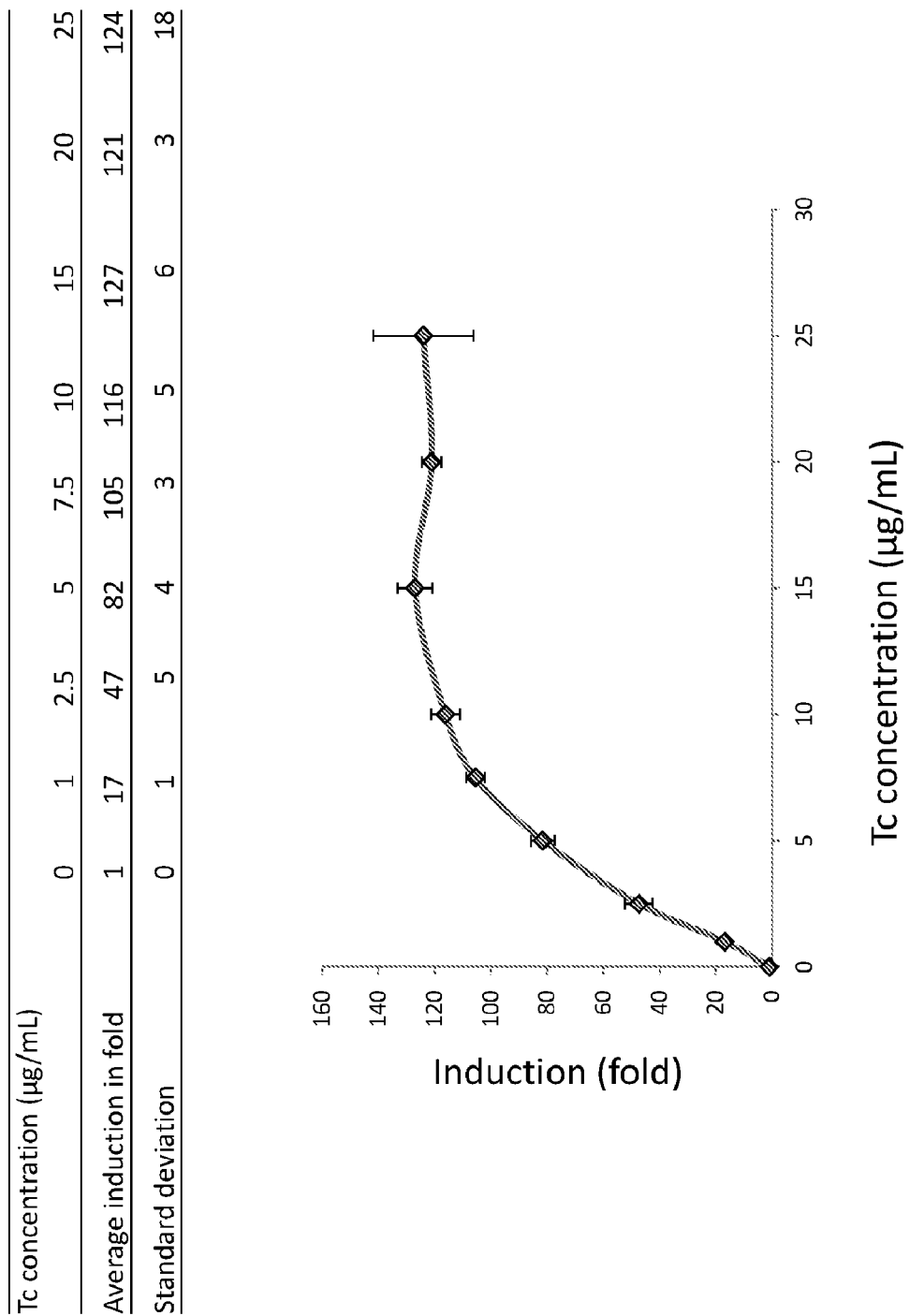
FIG. 31 demonstrates the dose-dependent regulation of D11A. Each data point corresponds to a relative fold induction determined as the ratio of luciferase activity with and without tc. Average fold induction with standard deviation are shown. The induction reached 127-fold at 15 μg/mL Tc.

Merely as examples, FIG. 28 provides the complete sequence of the GP2SLGP2 polyA sensor construct comprising the GP2 stem loop sequence (see FIG. 25), the C12 stem loop sequence (see FIG. 25), and the D11A stem loop sequence (see FIG. 25). To characterize their ability to induce expression, the three molecules were tested in varying concentrations of tetracycline (Tc, as an example of a ligand for the binding pocket). FIG. 29 demonstrates the dose-dependent regulation of GP2SLGP2. Each data point corresponds to a relative fold induction determined as the ratio of luciferase activity with and without Tc. Average fold induction with standard deviation are shown. The induction reached 104-fold at 15 μg/mL Tc. FIG. 30 demonstrates the dose-dependent regulation of the construct comprising the C12 sequence. Each data point corresponds to a relative fold induction determined as the ratio of luciferase activity with and without Tc. Average fold induction with standard deviation are shown. The induction reached 151-fold at 15 μg/mL Tc. FIG. 31 demonstrates the dose-dependent regulation of the construct comprising the D11A sequence. Each data point corresponds to a relative fold induction determined as the ratio of luciferase activity with and without tc. Average fold induction with standard deviation are shown. The induction reached 127-fold at 15 μg/mL Tc.

The scope of the present application is not intended to be limited to the particular embodiments of the process, machine, manufacture, composition of matter, means, methods and steps described in the specification.

REFERENCES

All publications mentioned in this specification are indicative of the level of those skilled in the art to which the invention pertains. All publications herein are incorporated by reference to the same extent as if each individual publication was specifically and individually indicated to be incorporated by reference in their entirety.

1. Gossen, M. & Bujard, H. Tight control of gene expression in mammalian cells by tetracycline-responsive promoters. *Proc Natl Acad Sci USA* 89, 5547-5551 (1992).
2. Rivera, V. M. et al. A humanized system for pharmacologic control of gene expression. *Nat Med* 2, 1028-1032 (1996).
3. Suhr, S. T., Gil, E. B., Senut, M. C. & Gage, F. H. High level transactivation by a modified *Bombyx* ecdysone receptor in mammalian cells without exogenous retinoid X receptor. *Proc Natl Acad Sci USA* 95, 7999-8004 (1998).
4. Yen, L. et al. Exogenous control of mammalian gene expression through modulation of RNA self-cleavage. *Nature* 431, 471-476 (2004).
5. Warnock, D. E., Fahy, E. & Taylor, S. W. Identification of protein associations in organelles, using mass spectrometry-based proteomics. *Mass Spectrom Rev* 23, 259-280 (2004).
6. Gimmi, E. R., Reff, M. E. & Deckman, I. C. Alterations in the pre-mRNA topology of the bovine growth hormone polyadenylation region decrease poly(A) site efficiency. *Nucleic acids research* 17, 6983-6998 (1989).
7. Ciesiolka, J. et al. Affinity selection-amplification from randomized ribooligonucleotide pools. *Methods Enzymol* 267, 315-335 (1996).
8. Ellington, A. D. & Szostak, J. W. In vitro selection of RNA molecules that bind specific ligands. *Nature* 346, 818-822 (1990).
9. Fitzwater, T. & Polisky, B. A SELEX primer. *Methods Enzymol* 267, 275-301 (1996).
10. Lee, J. F., Hesselberth, J. R., Meyers, L. A. & Ellington, A. D. Aptamer database. *Nucleic acids research* 32, D95-100 (2004).
11. Nimjee, S. M., Rusconi, C. P. & Sullenger, B. A. Aptamers: an emerging class of therapeutics. *Annu Rev Med* 56, 555-583 (2005).
12. Tuerk, C. & Gold, L. Systematic evolution of ligands by exponential enrichment: RNA ligands to bacteriophage T4 DNA polymerase. *Science* 249, 505-510 (1990).
13. Becskei, A. & Serrano, L. Engineering stability in gene networks by autoregulation. *Nature* 405, 590-593 (2000).
14. Becskei, A., Seraphin, B. & Serrano, L. Positive feedback in eukaryotic gene networks: cell differentiation by graded to binary response conversion. *The EMBO journal* 20, 2528-2535 (2001).
15. Carrier, T. A. & Keasling, J. D. Investigating autocatalytic gene expression systems through mechanistic modeling. *Journal of theoretical biology* 201, 25-36 (1999).
16. Demongeot, J., Kaufman, M. & Thomas, R. Positive feedback circuits and memory. *Comptes rendus de l'Academie des sciences. Serie III, Sciences de la vie* 323, 69-79 (2000).
17. Ferrell, J. E., Jr. Self-perpetuating states in signal transduction: positive feedback, double-negative feedback and bistability. *Current opinion in cell biology* 14, 140-148 (2002).
18. Isaacs, F. J., Hasty, J., Cantor, C. R. & Collins, J. J. Prediction and measurement of an autoregulatory genetic module. *Proc Natl Acad Sci USA* 100, 7714-7719 (2003).
19. Famulok, M., Hartig, J. S. & Mayer, G. Functional aptamers and aptazymes in biotechnology, diagnostics, and therapy. *Chem Rev* 107, 3715-3743 (2007).
20. Jenison, R. D., Gill, S. C., Pardi, A. & Polisky, B. High-resolution molecular discrimination by RNA. *Science* 263, 1425-1429 (1994).
21. Navani, N. K. & Li, Y. Nucleic acid aptamers and enzymes as sensors. *Curr Opin Chem Biol* 10, 272-281 (2006).
22. Hesselberth, J. R., Robertson, M. P., Knudsen, S. M. & Ellington, A. D. Simultaneous detection of diverse analytes with an aptazyme ligase array. *Anal Biochem* 312, 106-112 (2003).
23. Breaker, R. R. Engineered allosteric ribozymes as biosensor components. *Current opinion in biotechnology* 13, 31-39 (2002).
24. Tang, J. & Breaker, R. R. Rational design of allosteric ribozymes. *Chem Biol* 4, 453-459 (1997).
25. Mandal, M. & Breaker, R. R. Gene regulation by riboswitches. *Nature reviews* 5, 451-463 (2004).
26. Winkler, W. C., Nahvi, A., Roth, A., Collins, J. A. & Breaker, R. R. Control of gene expression by a natural metabolite-responsive ribozyme. *Nature* 428, 281-286 (2004).
27. Winkler, W. C. & Breaker, R. R. Regulation of bacterial gene expression by riboswitches. *Annual review of microbiology* 59, 487-517 (2005).
28. Win, M. N. & Smolke, C. D. A modular and extensible RNA-based gene-regulatory platform for engineering cellular function. *Proc Natl Acad Sci USA* 104, 14283-14288 (2007).
29. Win, M. N. & Smolke, C. D. Higher-order cellular information processing with synthetic RNA devices. *Science* 322, 456-460 (2008).
30. Proudfoot, N. New perspectives on connecting messenger RNA 3' end formation to transcription. *Current opinion in cell biology* 16, 272-278 (2004).
31. Proudfoot, N. J., Furger, A. & Dye, M. J. Integrating mRNA processing with transcription. *Cell* 108, 501-512 (2002).
32. Chen, F., MacDonald, C. C. & Wilusz, J. Cleavage site determinants in the mammalian polyadenylation signal. *Nucleic acids research* 23, 2614-2620 (1995).
33. Klasens, B. I., Thiesen, M., Virtanen, A. & Berkhout, B. The ability of the HIV-1 AAUAAA signal to bind polyadenylation factors is controlled by local RNA structure. *Nucleic acids research* 27, 446-454 (1999).
34. Zarudnaya, M. I., Kolomiets, I. M., Potyahaylo, A. L. & Hovorun, D. M. Downstream elements of mammalian pre-mRNA polyadenylation signals: primary, secondary and higher-order structures. *Nucleic acids research* 31, 1375-1386 (2003).
35. Yamamoto, R., Baba, T. & Kumar, P. K. Molecular beacon aptamer fluoresces in the presence of Tat protein of HIV-1. *Genes Cells* 5, 389-396 (2000).

36. Yamamoto, R. et al. A novel RNA motif that binds efficiently and specifically to the Ttat protein of HIV and inhibits the trans-activation by Tat of transcription in vitro and in vivo. *Genes Cells* 5, 371-388 (2000).
37. Long, S. B., Long, M. B., White, R. R. & Sullenger, B. A. Crystal structure of an RNA aptamer bound to thrombin. *RNA (New York, N.Y* 14, 2504-2512 (2008).
38. Ng, E. W. et al. Pegaptanib, a targeted anti-VEGF aptamer for ocular vascular disease. *Nat Rev Drug Discov* 5, 123-132 (2006).
39. Zhang, L., Yoo, S., Dritschilo, A., Belyaev, I. & Soldatenkov, V. Targeting Ku protein for sensitizing of breast cancer cells to DNA-damage. *Int J Mol Med* 14, 153-159 (2004).
40. Mi, Z. et al. RNA aptamer blockade of osteopontin inhibits growth and metastasis of MDA-MB231 breast cancer cells. *Mol Ther* 17, 153-161 (2009).
41. Cassiday, L. A. & Maher, L. J., 3rd Yeast genetic selections to optimize RNA decoys for transcription factor NF-kappa B. *Proc Natl Acad Sci USA* 100, 3930-3935 (2003).
42. Reiter, N. J., Maher, L. J., 3rd & Butcher, S. E. DNA mimicry by a high-affinity anti-NF-kappaB RNA aptamer. *Nucleic acids research* 36, 1227-1236 (2008).
43. Vaish, N. K. et al. Monitoring post-translational modification of proteins with allosteric ribozymes. *Nature biotechnology* 20, 810-815 (2002).
44. Shu, X. et al. Mammalian expression of infrared fluorescent proteins engineered from a bacterial phytochrome. *Science* 324, 804-807 (2009).
45. Hung, S. C. et al. Mesenchymal stem cell targeting of microscopic tumors and tumor stroma development monitored by noninvasive in vivo positron emission tomography imaging. *Clin Cancer Res* 11, 7749-7756 (2005).
46. Yaghoubi, S. S. & Gambhir, S. S. PET imaging of herpes simplex virus type 1 thymidine kinase (HSV1-tk) or mutant HSV1-sr39tk reporter gene expression in mice and humans using [18F]FHBG. *Nat Protoc* 1, 3069-3075 (2006).
47. Yaghoubi, S. S. et al. Noninvasive detection of therapeutic cytolytic T cells with 18F-FHBG PET in a patient with glioma. *Nat Clin Pract Oncol* 6, 53-58 (2009).
48. Perez-Torres, C. J., Massaad, C. A., Hilsenbeck, S. G., Serrano, F. & Pautler, R. G. In vitro and in vivo magnetic resonance imaging (MRI) detection of GFP through magnetization transfer contrast (MTC). *Neuroimage* 50, 375-382 (2010).
49. Ory, D. S., Neugeboren, B. A. & Mulligan, R. C. A stable human-derived packaging cell line for production of high titer retrovirus/vesicular stomatitis virus G pseudotypes. *Proc Natl Acad Sci USA* 93, 11400-11406 (1996).
50. Sheets, M. D., Ogg, S. C. & Wickens, M. P. Point mutations in AAUAAA and the poly (A) addition site: effects on the accuracy and efficiency of cleavage and polyadenylation in vitro. *Nucleic acids research* 18, 5799-5805 (1990).
51. Levitt, N., Briggs, D., Gil, A. & Proudfoot, N. J. Definition of an efficient synthetic poly(A) site. *Genes & development* 3, 1019-1025 (1989).
52. Ashfield, R. et al. MAZ-dependent termination between closely spaced human complement genes. *The EMBO journal* 13, 5656-5667 (1994).
53. Gromak, N., West, S. & Proudfoot, N. J. Pause sites promote transcriptional termination of mammalian RNA polymerase II. *Molecular and cellular biology* 26, 3986-3996 (2006).
54. Yonaha, M. & Proudfoot, N. J. Specific transcriptional pausing activates polyadenylation in a coupled in vitro system. *Molecular cell* 3, 593-600 (1999).
55. Yen, L., Magnier, M., Weissleder, R., Stockwell, B. R. & Mulligan, R. C. Identification of inhibitors of ribozyme self-cleavage in mammalian cells via high-throughput screening of chemical libraries. *RNA (New York, N.Y* 12, 797-806 (2006).
56. Contag, C. H. et al. Visualizing gene expression in living mammals using a bioluminescent reporter. *Photochem Photobiol* 66, 523-531 (1997).
57. Contag, P. R., Olomu, I. N., Stevenson, D. K. & Contag, C. H. Bioluminescent indicators in living mammals. *Nat Med* 4, 245-247 (1998).

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A system for modulating gene expression, comprising a polyA aptamer polynucleotide that comprises in a 5' to 3' direction:
   a) at least one ligand-binding aptamer comprising at least one polyA cleavage signal therein; and
   b) an expressible polynucleotide that is a reporter gene, wherein:
      (i) the at least one ligand-binding aptamer resides within the 5' untranslated region (UTR) of the expressible polynucleotide;
      (ii) the polyA aptamer polynucleotide comprises at least one U/UG rich region, at least one G rich region, or both of at least one U/UG rich region and at least one G rich region; and
      (iii) in a 5' to 3' direction, the at least one poly A cleavage signal resides upstream of the at least one U/UG rich region and/or the at least one G rich region.

2. The system of claim 1, wherein the system comprises a polynucleotide that expresses a ligand that binds the at least one ligand-binding aptamer.

3. The system of claim 2, wherein the polynucleotide that expresses the ligand is the same polyA aptamer polynucleotide that comprises the aptamer and expressible polynucleotide.

4. The system of claim 2, wherein the polynucleotide that expresses the ligand is a different polynucleotide than the polyA aptamer polynucleotide that comprises the aptamer and expressible polynucleotide.

5. The system of claim 2, wherein the polyA aptamer polynucleotide comprises two, three, or more polyA signals in the 5' UTR of the expressible polynucleotide.

6. The system of claim 1, wherein the ligand-binding aptamer comprises one, two, three, or more U/UG rich regions.

7. The system of claim 1, wherein in a 5' to 3' direction of the polyA aptamer polynucleotide the ligand-binding aptamer resides upstream of one, two, or more U/UG rich regions.

8. The system of claim 2, wherein in a 5' to 3' direction of the polyA aptamer polynucleotide the ligand-binding aptamer resides upstream of one, two, or more G rich regions.

9. The system of claim 1, wherein in a 5' to 3' direction of the polyA aptamer polynucleotide the aptamer comprises two polyA signals and two U/UG rich regions.

10. The system of claim 1, wherein the polyA aptamer polynucleotide comprises 2, 3, 4, 5, or more aptamers.

11. The system of claim 10, wherein a first aptamer and a second aptamer are in the same orientation in a 5' to 3' linear direction.

12. The system of claim 10, wherein a first aptamer and a second aptamer are in a different orientation in a 5' to 3' linear direction.

13. The system of claim 10, wherein the polyA aptamer polynucleotide comprises one G-rich region.

14. The system of claim 13, wherein the G-rich region is in the 3'-most aptamer in a 5' to 3' direction of the polyA aptamer polynucleotide.

15. The system of claim 13, wherein the G-rich region is in the second aptamer in a 5' to 3' direction of the polyA aptamer polynucleotide.

16. The system of claim 1, wherein the at least one ligand-binding aptamer comprises two or more loops and wherein the number of nucleotides between two loops within the at least one ligand-binding aptamer is 10-25 nucleotides.

17. The system of claim 1, wherein the ligand is a polypeptide, peptide, nucleic acid, small molecule, drug, metabolite, or a combination thereof.

18. The system of claim 1, wherein the aptamer is between 14 and 250 nucleotides in length.

19. The system of claim 1, wherein the polyA aptamer polynucleotide is at least part of a vector.

20. The system of claim 1, wherein the expressible polynucleotide encodes the ligand.

21. The system of claim 1, wherein expression of the expressible polynucleotide is regulated by a tissue-specific promoter.

22. A polyA aptamer polynucleotide, wherein said polynucleotide comprises in a 5' to 3' direction:
   a) at least one ligand-binding aptamer that comprises at least one polyA cleavage signal therein; and
   b) an expressible polynucleotide that is a reporter gene, wherein:
      (i) the at least one ligand-binding aptamer resides within the 5' untranslated region (UTR) of the expressible polynucleotide;
      (ii) the polyA aptamer polynucleotide comprises at least one U/UG rich region, at least one G rich region, or both of at least one U/UG rich region and at least one G rich region; and
      (iii) in a 5' to 3' direction, the at least one poly A cleavage signal resides upstream of the at least one U/UG rich region and/or the at least one G rich region.

23. A cell comprising the polynucleotide of claim 22.

24. A cell comprising the system of claim 1.

25. A vector comprising the polynucleotide of claim 22.

26. The system of claim 1, wherein the polyA aptamer polynucleotide comprises in a 5' to 3' direction:
   a) three ligand-binding aptamers, wherein at least one of the ligand-binding aptamers is the at least one ligand-binding aptamer comprising at least one polyA cleavage signal therein;
   b) at least one U/UG rich region and at least one G rich region; and
   c) the expressible polynucleotide,
   wherein the at least one of the ligand-binding aptamers comprising a polyA cleavage signal resides within the 5' untranslated region (UTR) of the expressible polynucleotide.

27. The system of claim 26, wherein the system comprises a polynucleotide that expresses a ligand that binds at least one of the ligand-binding aptamers.

28. The system of claim 26, wherein the polyA aptamer polynucleotide comprises two, three, or more polyA cleavage signals in the 5' UTR of the expressible polynucleotide.

29. The system of claim 26, wherein the ligand-binding aptamer comprises two, three, or more U/UG rich regions.

30. The system of claim 26, wherein in a 5' to 3' direction of the polyA aptamer polynucleotide:
   at least one of the ligand-binding aptamers resides upstream of one, two, or more U/UG rich regions; or
   at least one of the ligand-binding aptamers resides upstream of one, two, or more G rich regions.

31. The system of claim 26, wherein the G-rich region is in the 3'-most ligand-binding aptamer in a 5' to 3' direction of the polyA aptamer polynucleotide.

32. The system of claim 26, wherein the at least one of the three ligand-binding aptamers comprises two or more loops and wherein the number of nucleotides between two loops within said ligand-binding aptamer comprising two or more loops is 10-25 nucleotides.

33. The system of claim 26, wherein a ligand-binding aptamer is between 14 and 250 nucleotides in length.

* * * * *

SEQUENCE LISTING

<160> NUMBER OF SEQ ID NOS: 61

<210> SEQ ID NO 1
<211> LENGTH: 50
<212> TYPE: RNA
<213> ORGANISM: Artificial Sequence
<220> FEATURE:
<223> OTHER INFORMATION: Synthetic Primer

<400> SEQUENCE: 1
ucccacuguc cuuuccuaau aaaaugagga aauugcaucg cauugucuga          50

<210> SEQ ID NO 2

```
<211> LENGTH: 93
<212> TYPE: RNA
<213> ORGANISM: Artificial Sequence
<220> FEATURE:
<223> OTHER INFORMATION: Synthetic Primer

<400> SEQUENCE: 2
ucagacaaug cgaugcaauu ucgagcucuc gcgaggugcc acucccacu guccuuccu    60 aauaaaauga ggaaauugca ucgcauuguc uga                              93

<210> SEQ ID NO 3
<211> LENGTH: 12
<212> TYPE: RNA
<213> ORGANISM: Artificial Sequence
<220> FEATURE:
<223> OTHER INFORMATION: Synthetic Primer

<400> SEQUENCE: 3
aauaaaaaua aa                                                     12

<210> SEQ ID NO 4
<211> LENGTH: 71
<212> TYPE: RNA
<213> ORGANISM: Artificial Sequence
<220> FEATURE:
<223> OTHER INFORMATION: Synthetic Primer

<400> SEQUENCE: 4
gggccuaaaa cauaccagau cgccacccgc gcuuuaaucu ggagagguga agaauacgac  60
caccuaggcu c                                                      71

<210> SEQ ID NO 5
<211> LENGTH: 12
<212> TYPE: RNA
<213> ORGANISM: Artificial Sequence
<220> FEATURE:
<223> OTHER INFORMATION: Synthetic Primer

<400> SEQUENCE: 5
aauaaaaaua aa                                                     12

<210> SEQ ID NO 6
<211> LENGTH: 12
<212> TYPE: RNA
<213> ORGANISM: Artificial Sequence
<220> FEATURE:
<223> OTHER INFORMATION: Synthetic Primer

<400> SEQUENCE: 6
cacacaaaua aa                                                     12

<210> SEQ ID NO 7
<211> LENGTH: 12
<212> TYPE: RNA
<213> ORGANISM: Artificial Sequence
<220> FEATURE:
<223> OTHER INFORMATION: Synthetic Primer

<400> SEQUENCE: 7
aaauaaacac ac                                                     12

<210> SEQ ID NO 8
<211> LENGTH: 92
<212> TYPE: RNA
<213> ORGANISM: Artificial Sequence
```

```
<220> FEATURE:
<223> OTHER INFORMATION: Synthetic Primer

<400> SEQUENCE: 8
cacagaucug gagaggugaa gaauacgacc accugcguuu uauacuuugu aacacaaaua    60
aaguauaaag ugcaaaacau accagaucug ug                                 92

<210> SEQ ID NO 9
<211> LENGTH: 92
<212> TYPE: RNA
<213> ORGANISM: Artificial Sequence
<220> FEATURE:
<223> OTHER INFORMATION: Synthetic Primer

<400> SEQUENCE: 9
cacagaucug gagaggugaa gaauacgacc accugcguua uauacuuugu aacacaaaua    60
aaguauauag ugcaaaacau accagaucug ug                                 92

<210> SEQ ID NO 10
<211> LENGTH: 27
<212> TYPE: DNA
<213> ORGANISM: Artificial Sequence
<220> FEATURE:
<223> OTHER INFORMATION: Synthetic Primer

<400> SEQUENCE: 10
gtgcaaaaca aaaaaaaaaa aaaaaaa                                       27

<210> SEQ ID NO 11
<211> LENGTH: 27
<212> TYPE: DNA
<213> ORGANISM: Artificial Sequence
<220> FEATURE:
<223> OTHER INFORMATION: Synthetic Primer

<400> SEQUENCE: 11
gtgcaaaaca taaaaaaaaa aaaaaaa                                       27

<210> SEQ ID NO 12
<211> LENGTH: 28
<212> TYPE: DNA
<213> ORGANISM: Artificial Sequence
<220> FEATURE:
<223> OTHER INFORMATION: Synthetic Primer

<400> SEQUENCE: 12
gtgcaaaaca taccaaaaaa aaaaaaaa                                      28

<210> SEQ ID NO 13
<211> LENGTH: 92
<212> TYPE: RNA
<213> ORGANISM: Artificial Sequence
<220> FEATURE:
<223> OTHER INFORMATION: Synthetic Primer

<400> SEQUENCE: 13
cacagaucug gagaggugaa gaauacgacc accugcguuu uauacuuugu aacacaaaua    60
aaguauaaag ugcaaaacau accagaucug ug                                 92

<210> SEQ ID NO 14
<211> LENGTH: 11
<212> TYPE: RNA
<213> ORGANISM: Artificial Sequence
<220> FEATURE:
```

```
<223> OTHER INFORMATION: Synthetic Primer

<400> SEQUENCE: 14
aaaacauacc a                                                          11

<210> SEQ ID NO 15
<211> LENGTH: 92
<212> TYPE: RNA
<213> ORGANISM: Artificial Sequence
<220> FEATURE:
<223> OTHER INFORMATION: Synthetic Primer

<400> SEQUENCE: 15
cacagaucug gagaggugaa gaauacgacc accugcguuu uauacuuugu aacacaaaua     60
aaguauaaag ugcaaaacau accagaucug ug                                   92

<210> SEQ ID NO 16
<211> LENGTH: 92
<212> TYPE: RNA
<213> ORGANISM: Artificial Sequence
<220> FEATURE:
<223> OTHER INFORMATION: Synthetic Primer

<400> SEQUENCE: 16
cacagaucug gggaggugaa gaauacgacc accugcguuu uauacuuugu aacacaaaua     60
aaguauaaag ugcaaaacau accagaucug ug                                   92

<210> SEQ ID NO 17
<211> LENGTH: 92
<212> TYPE: RNA
<213> ORGANISM: Artificial Sequence
<220> FEATURE:
<223> OTHER INFORMATION: Synthetic Primer

<400> SEQUENCE: 17
cacaaaucug gggaggugaa gaauacgacc accugcguuu uauacuuugu aacacaaaua     60
aaguauaaag ugcaaaacau accagaucug ug                                   92

<210> SEQ ID NO 18
<211> LENGTH: 92
<212> TYPE: DNA
<213> ORGANISM: Artificial Sequence
<220> FEATURE:
<223> OTHER INFORMATION: Synthetic Primer

<400> SEQUENCE: 18
cacaaaucug gggaggugaa gaauacgacc accugcuagu uauacuuugu aacacaaaua     60
aaguauagct agcaaaacau accagaucug ug                                   92

<210> SEQ ID NO 19
<211> LENGTH: 92
<212> TYPE: RNA
<213> ORGANISM: Artificial Sequence
<220> FEATURE:
<223> OTHER INFORMATION: Synthetic Primer

<400> SEQUENCE: 19
cacaaaucug gggaggugaa gaauacgacc accugcguuu uauacuuugu aacacaaaua     60
aaguauaaag ugcaaaacau accagaucug ug                                   92

<210> SEQ ID NO 20
<211> LENGTH: 92
```

```
<212> TYPE: DNA
<213> ORGANISM: Artificial Sequence
<220> FEATURE:
<223> OTHER INFORMATION: Synthetic Primer

<400> SEQUENCE: 20
cacaaaucug gggaggugaa gaauacgacc accugcuagu uauacuuugu aacacaaaua    60
aaguauagct agcaaaacau accagaucug ug                                 92

<210> SEQ ID NO 21
<211> LENGTH: 92
<212> TYPE: DNA
<213> ORGANISM: Artificial Sequence
<220> FEATURE:
<223> OTHER INFORMATION: Synthetic Primer

<400> SEQUENCE: 21
cacaaaucug gggaggugaa gaauacgacc accugcuagu uauacuuugu aacacaaaua    60
aaguauagct agcaaaacau accagaucug ug                                 92

<210> SEQ ID NO 22
<211> LENGTH: 12
<212> TYPE: RNA
<213> ORGANISM: Artificial Sequence
<220> FEATURE:
<223> OTHER INFORMATION: Synthetic Primer

<400> SEQUENCE: 22 ccaaccccg ca                                                        12

<210> SEQ ID NO 23
<211> LENGTH: 11
<212> TYPE: RNA
<213> ORGANISM: Artificial Sequence
<220> FEATURE:
<223> OTHER INFORMATION: Synthetic Primer

<400> SEQUENCE: 23
uuugcuuaga a                                                        11

<210> SEQ ID NO 24
<211> LENGTH: 12
<212> TYPE: RNA
<213> ORGANISM: Artificial Sequence
<220> FEATURE:
<223> OTHER INFORMATION: Synthetic Primer

<400> SEQUENCE: 24 ccgucuccc ca                                                        12

<210> SEQ ID NO 25
<211> LENGTH: 12
<212> TYPE: RNA
<213> ORGANISM: Artificial Sequence
<220> FEATURE:
<223> OTHER INFORMATION: Synthetic Primer

<400> SEQUENCE: 25
ggggccucga ga                                                       12

<210> SEQ ID NO 26
<211> LENGTH: 97
<212> TYPE: RNA
<213> ORGANISM: Artificial Sequence
<220> FEATURE:
```

```
<223> OTHER INFORMATION: Synthetic Primer

<400> SEQUENCE: 26
cacagaucug gggaggugaa gaauacgacc accugcguuu uauacuuugu uggaacacac    60
caauaaagua uaaagugcaa aacauaccag aucugug                            97

<210> SEQ ID NO 27
<211> LENGTH: 92
<212> TYPE: DNA
<213> ORGANISM: Artificial Sequence
<220> FEATURE:
<223> OTHER INFORMATION: Synthetic Primer

<400> SEQUENCE: 27
cacaaaucug gggaggugaa gaauacgacc accugcuagu uacgcuuugu aacacaaaua    60
aagcguagct agcaaaacau accagaucug ug                                 92

<210> SEQ ID NO 28
<211> LENGTH: 136
<212> TYPE: RNA
<213> ORGANISM: Artificial Sequence
<220> FEATURE:
<223> OTHER INFORMATION: Synthetic Primer

<400> SEQUENCE: 28
cacaaaucug gggaggugaa gaauacgacc accugcguuu uauacuuugu uaaaacauac    60
cagaucgaaa gaucugggga ggugaagaau acgaccaccu aauaaaguau aaagugcaaa   120
acauaccaga ucugug                                                  136

<210> SEQ ID NO 29
<211> LENGTH: 10
<212> TYPE: RNA
<213> ORGANISM: Artificial Sequence
<220> FEATURE:
<223> OTHER INFORMATION: Synthetic Primer

<400> SEQUENCE: 29
aucgaaagau                                                          10

<210> SEQ ID NO 30
<211> LENGTH: 10
<212> TYPE: RNA
<213> ORGANISM: Artificial Sequence
<220> FEATURE:
<223> OTHER INFORMATION: Synthetic Primer

<400> SEQUENCE: 30
auugaaagau                                                          10

<210> SEQ ID NO 31
<211> LENGTH: 21
<212> TYPE: DNA
<213> ORGANISM: Artificial Sequence
<220> FEATURE:
<223> OTHER INFORMATION: Synthetic Peptide

<400> SEQUENCE: 31
accagatcga aagatctggg g                                             21

<210> SEQ ID NO 32
<211> LENGTH: 21
<212> TYPE: DNA
<213> ORGANISM: Artificial Sequence
```

```
<220> FEATURE:
<223> OTHER INFORMATION: Synthetic Peptide

<400> SEQUENCE: 32
accagatcga tcgatctggg g                                              21

<210> SEQ ID NO 33
<211> LENGTH: 19
<212> TYPE: DNA
<213> ORGANISM: Artificial Sequence
<220> FEATURE:
<223> OTHER INFORMATION: Synthetic Peptide

<400> SEQUENCE: 33
accagatcgc gatctggggg                                                19

<210> SEQ ID NO 34
<211> LENGTH: 17
<212> TYPE: DNA
<213> ORGANISM: Artificial Sequence
<220> FEATURE:
<223> OTHER INFORMATION: Synthetic Primer

<400> SEQUENCE: 34
accagatcga tctgggg                                                   17

<210> SEQ ID NO 35
<211> LENGTH: 22
<212> TYPE: DNA
<213> ORGANISM: Artificial Sequence
<220> FEATURE:
<223> OTHER INFORMATION: Synthetic Primer

<400> SEQUENCE: 35
accagatcga ttcgatctgg gg                                             22

<210> SEQ ID NO 36
<211> LENGTH: 15
<212> TYPE: DNA
<213> ORGANISM: Artificial Sequence
<220> FEATURE:
<223> OTHER INFORMATION: Synthetic Primer

<400> SEQUENCE: 36
accagatatc tgggg                                                     15

<210> SEQ ID NO 37
<211> LENGTH: 23
<212> TYPE: DNA
<213> ORGANISM: Artificial Sequence
<220> FEATURE:
<223> OTHER INFORMATION: Synthetic Primer

<400> SEQUENCE: 37
accagatcga attcgatctg ggg                                            23

<210> SEQ ID NO 38
<211> LENGTH: 24
<212> TYPE: DNA
<213> ORGANISM: Artificial Sequence
<220> FEATURE:
<223> OTHER INFORMATION: Synthetic Primer

<400> SEQUENCE: 38
accagatcga atttcgatct gggg                                           24
```

```
<210> SEQ ID NO 39
<211> LENGTH: 25
<212> TYPE: DNA
<213> ORGANISM: Artificial Sequence
<220> FEATURE:
<223> OTHER INFORMATION: Synthetic Primer

<400> SEQUENCE: 39
accagatcga atattcgatc tgggg                                              25

<210> SEQ ID NO 40
<211> LENGTH: 26
<212> TYPE: DNA
<213> ORGANISM: Artificial Sequence
<220> FEATURE:
<223> OTHER INFORMATION: Synthetic Primer

<400> SEQUENCE: 40
accagatcga atcattcgat ctgggg                                             26

<210> SEQ ID NO 41
<211> LENGTH: 27
<212> TYPE: DNA
<213> ORGANISM: Artificial Sequence
<220> FEATURE:
<223> OTHER INFORMATION: Synthetic Primer

<400> SEQUENCE: 41
accagatcga atcgattcga tctgggg                                            27

<210> SEQ ID NO 42
<211> LENGTH: 27
<212> TYPE: DNA
<213> ORGANISM: Artificial Sequence
<220> FEATURE:
<223> OTHER INFORMATION: Synthetic Primer

<400> SEQUENCE: 42
accagattac ccttgggtga tctgggg                                            27

<210> SEQ ID NO 43
<211> LENGTH: 28
<212> TYPE: DNA
<213> ORGANISM: Artificial Sequence
<220> FEATURE:
<223> OTHER INFORMATION: Synthetic Primer

<400> SEQUENCE: 43
accagatcga atctgattcg atctgggg                                           28

<210> SEQ ID NO 44
<211> LENGTH: 41
<212> TYPE: DNA
<213> ORGANISM: Artificial Sequence
<220> FEATURE:
<223> OTHER INFORMATION: Synthetic Primer

<400> SEQUENCE: 44
accatcctaa gcctaaggca aacgctatgg tatggatggg g                            41

<210> SEQ ID NO 45
<211> LENGTH: 21
<212> TYPE: DNA
<213> ORGANISM: Artificial Sequence
<220> FEATURE:
<223> OTHER INFORMATION: Synthetic Primer
```

```
<400> SEQUENCE: 45
accagatcga aagatctggg g                                              21

<210> SEQ ID NO 46
<211> LENGTH: 21
<212> TYPE: DNA
<213> ORGANISM: Artificial Sequence
<220> FEATURE:
<223> OTHER INFORMATION: Synthetic Primer

<400> SEQUENCE: 46
accagatcga tcgatctggg g                                              21

<210> SEQ ID NO 47
<211> LENGTH: 19
<212> TYPE: DNA
<213> ORGANISM: Artificial Sequence
<220> FEATURE:
<223> OTHER INFORMATION: Synthetic Primer

<400> SEQUENCE: 47
accagatcgc gatctgggg                                                 19

<210> SEQ ID NO 48
<211> LENGTH: 17
<212> TYPE: DNA
<213> ORGANISM: Artificial Sequence
<220> FEATURE:
<223> OTHER INFORMATION: Synthetic Primer

<400> SEQUENCE: 48
accagatcga tctgggg                                                   17

<210> SEQ ID NO 49
<211> LENGTH: 22
<212> TYPE: DNA
<213> ORGANISM: Artificial Sequence
<220> FEATURE:
<223> OTHER INFORMATION: Synthetic Primer

<400> SEQUENCE: 49
accagatcga atcgatctgg gg                                             22

<210> SEQ ID NO 50
<211> LENGTH: 15
<212> TYPE: DNA
<213> ORGANISM: Artificial Sequence
<220> FEATURE:
<223> OTHER INFORMATION: Synthetic Primer

<400> SEQUENCE: 50
accagatatc tgggg                                                     15

<210> SEQ ID NO 51
<211> LENGTH: 23
<212> TYPE: DNA
<213> ORGANISM: Artificial Sequence
<220> FEATURE:
<223> OTHER INFORMATION: Synthetic Primer

<400> SEQUENCE: 51
accagatcga attcgatctg ggg                                            23

<210> SEQ ID NO 52
```

```
<211> LENGTH: 24
<212> TYPE: DNA
<213> ORGANISM: Artificial Sequence
<220> FEATURE:
<223> OTHER INFORMATION: Synthetic Primer

<400> SEQUENCE: 52
accagatcga aattcgatct gggg                                              24

<210> SEQ ID NO 53
<211> LENGTH: 25
<212> TYPE: DNA
<213> ORGANISM: Artificial Sequence
<220> FEATURE:
<223> OTHER INFORMATION: Synthetic Primer

<400> SEQUENCE: 53
accagatcga atattcgatc tgggg                                             25

<210> SEQ ID NO 54
<211> LENGTH: 26
<212> TYPE: DNA
<213> ORGANISM: Artificial Sequence
<220> FEATURE:
<223> OTHER INFORMATION: Synthetic Primer

<400> SEQUENCE: 54
accagatcga atgattcgat ctgggg                                            26

<210> SEQ ID NO 55
<211> LENGTH: 27
<212> TYPE: DNA
<213> ORGANISM: Artificial Sequence
<220> FEATURE:
<223> OTHER INFORMATION: Synthetic Primer

<400> SEQUENCE: 55
accagatcga atcgattcga tctgggg                                           27

<210> SEQ ID NO 56
<211> LENGTH: 27
<212> TYPE: DNA
<213> ORGANISM: Artificial Sequence
<220> FEATURE:
<223> OTHER INFORMATION: Synthetic Primer

<400> SEQUENCE: 56
accagattac ccgagggtga tctgggg                                           27

<210> SEQ ID NO 57
<211> LENGTH: 28
<212> TYPE: DNA
<213> ORGANISM: Artificial Sequence
<220> FEATURE:
<223> OTHER INFORMATION: Synthetic Primer

<400> SEQUENCE: 57
accagatcga atcagattcg atctgggg                                          28

<210> SEQ ID NO 58
<211> LENGTH: 21
<212> TYPE: DNA
<213> ORGANISM: Artificial Sequence
<220> FEATURE:
<223> OTHER INFORMATION: Synthetic Primer

<400> SEQUENCE: 58
```

```
accagatcga aagatctggg g                                               21
```

<210> SEQ ID NO 59
<211> LENGTH: 370
<212> TYPE: DNA
<213> ORGANISM: Artificial Sequence
<220> FEATURE:
<223> OTHER INFORMATION: Synthetic Primerr

<400> SEQUENCE: 59

```
gctagccaca cacacaaatc tggggaggtg aagaatacga ccacctgcgt tttatacttt     60
gttaaaacat accagatcga aagatctggg gaggtgaaga atacgaccac ctaataaagt    120
ataaagtgca aaacatacca gatctgtgtg ttggttttt  gtgtggaatt ccacacacac    180
aaatctgggg aggtgaagaa tacgaccacc tgcgttttat actttgttaa aacataccag    240
atcgaaagat ctggggaggt gaagaatacg accacctaat aaagtataaa gtgcaaaaca    300
taccagatct gtgtgttggt tttttgtgtg aacgggggag gggaggaaa  ggggagggg     360
gagcggccgc                                                           370
```

<210> SEQ ID NO 60
<211> LENGTH: 374
<212> TYPE: DNA
<213> ORGANISM: Artificial Sequence
<220> FEATURE:
<223> OTHER INFORMATION: Synthetic Primer

<400> SEQUENCE: 60

```
ctgcagcaca cacacaaatc tggggaggtg aagaatacga ccacctgcgt tttatacttt     60
gttaaaacat accagatcga attcgatctg gggaggtgaa gaatacgacc acctaataaa    120
gtataaagtg caaaacatac cagatctgtg tgttggtttt ttgtgtggct agccacacac    180
acaaatctgg ggaggtgaag aatacgacca cctgcgtttt atactttgtt aaaacatacc    240
agatcgaatt cgatctgggg aggtgaagaa tacgaccacc taataaagta taaagtgcaa    300
aacataccag atctgtgtgt tggttttttg tgtgaacggg ggaggggag  gaaaggggga    360
gggggagcgg ccgc                                                      374
```

<210> SEQ ID NO 61
<211> LENGTH: 396
<212> TYPE: DNA
<213> ORGANISM: Artificial Sequence
<220> FEATURE:
<223> OTHER INFORMATION: Synthetic Primer

<400> SEQUENCE: 61

```
gctagcgaat tgcacacaca caaatctggg gaggtgaaga atacgaccac ctgcgtttta     60
tactttgtta aaacatacca tcctaagcct aaggcaaacg ctatggtatg gatggggagg    120
tgaagaatac gaccacctaa taagtataaa gtgcaaaac  ataccagatc tgtgtgttgg    180
ttttttgtgt ggaattccac acacacaaat ctggggaggt gaagaatacg accacctgcg    240
ttttatactt tgttaaaaca taccagatcg aaagatctgg ggaggtgaag aatacgacca    300
cctaataaag tataaagtgc aaaacatacc agatcgtgtg ttggttttt  tgtgtgaacg    360
gggagggggg aggaaagggg gagggggagc ggccgc                              396
```